(12) United States Patent
Kosaka et al.

(10) Patent No.: US 9,740,117 B2
(45) Date of Patent: Aug. 22, 2017

(54) ELECTROPHOTOGRAPHIC PHOTOSENSITIVE MEMBER, PROCESS CARTRIDGE, ELECTROPHOTOGRAPHIC APPARATUS, AND CONDENSED POLYCYCLIC AROMATIC COMPOUND

(71) Applicant: CANON KABUSHIKI KAISHA, Tokyo (JP)

(72) Inventors: Nobuo Kosaka, Gotemba (JP); Koichi Nakata, Kashiwa (JP); Shinji Takagi, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 48 days.

(21) Appl. No.: 14/653,610

(22) PCT Filed: Mar. 6, 2014

(86) PCT No.: PCT/JP2014/056587
§ 371 (c)(1),
(2) Date: Jun. 18, 2015

(87) PCT Pub. No.: WO2014/136987
PCT Pub. Date: Sep. 12, 2014

(65) Prior Publication Data
US 2016/0011529 A1  Jan. 14, 2016

(30) Foreign Application Priority Data

Mar. 7, 2013 (JP) .................. 2013-045712
Mar. 3, 2014 (JP) .................. 2014-040676

(51) Int. Cl.
| | |
|---|---|
| *G03G 5/07* | (2006.01) |
| *G03G 5/147* | (2006.01) |
| *G03G 5/06* | (2006.01) |
| *C08F 2/50* | (2006.01) |
| *C07C 39/04* | (2006.01) |
| *C07C 39/17* | (2006.01) |
| *C07C 69/533* | (2006.01) |
| *C07C 69/602* | (2006.01) |
| *C07D 303/28* | (2006.01) |
| *C07D 305/06* | (2006.01) |
| *C07D 307/91* | (2006.01) |
| *C07D 309/12* | (2006.01) |
| *C08F 220/30* | (2006.01) |
| *C08F 222/10* | (2006.01) |

(52) U.S. Cl.
CPC .......... *G03G 5/0648* (2013.01); *C07C 39/04* (2013.01); *C07C 39/17* (2013.01); *C07C 69/533* (2013.01); *C07C 69/602* (2013.01); *C07D 303/28* (2013.01); *C07D 305/06* (2013.01); *C07D 307/91* (2013.01); *C07D 309/12* (2013.01); *C08F 2/50* (2013.01); *G03G 5/0609* (2013.01); *G03G 5/0629* (2013.01); *G03G 5/071* (2013.01); *G03G 5/073* (2013.01); *G03G 5/075* (2013.01); *G03G 5/14734* (2013.01); *G03G 5/14743* (2013.01); *G03G 5/14786* (2013.01); *C07C 2103/18* (2013.01); *C07C 2103/40* (2013.01); *C08F 220/30* (2013.01); *C08F 222/1006* (2013.01); *C08F 2222/102* (2013.01)

(58) Field of Classification Search
CPC .......... G03G 5/14713; G03G 5/14704; G03G 5/147; G03G 5/14786; G03G 5/14734; G03G 5/14743; G03G 5/071; G03G 5/075; G03G 5/076; G03G 5/07
USPC .................. 430/59, 6, 66, 67, 72, 58.05
See application file for complete search history.

(56) References Cited

U.S. PATENT DOCUMENTS

| | | | |
|---|---|---|---|
| 4,075,012 A * | 2/1978 | Turner | C08F 20/30 430/58.25 |
| 5,430,526 A * | 7/1995 | Ohkubo | G03G 15/0233 399/159 |
| 6,884,559 B2 | 4/2005 | Yokota | |

(Continued)

FOREIGN PATENT DOCUMENTS

| | | |
|---|---|---|
| CN | 102617768 A | 8/2012 |
| JP | 2003-295485 A | 10/2003 |

(Continued)

OTHER PUBLICATIONS

Diamond, A.S., ed., Handbook of Imaging Materials, Marcel Dekker, Inc., NY (1991), pp. 395-396.*

(Continued)

*Primary Examiner* — Janis L Dote
(74) *Attorney, Agent, or Firm* — Fitzpatrick Cella Harper and Scinto

(57) ABSTRACT

Provided are an electrophotographic photosensitive member which satisfies wear resistance and electrical characteristics, and in which image deletion is satisfactorily suppressed, and a process cartridge and an electrophotographic apparatus each including the electrophotographic photosensitive member. The electrophotographic photosensitive member comprises a surface layer which includes a polymerized product of a hole transporting substance having a reactive functional group, in which a structure other than the reactive functional group of the hole transporting substance is one of: a structure consisting of a carbon atom and a hydrogen atom; and a structure consisting of a carbon atom, a hydrogen atom and an oxygen atom, and the structure other than the reactive functional group of the hole transporting substance comprises a specific conjugate structure.

14 Claims, 2 Drawing Sheets

(56) References Cited

U.S. PATENT DOCUMENTS

| | | |
|---|---|---|
| 7,012,123 B2 | 3/2006 | Ishizawa et al. |
| 8,669,030 B2 | 3/2014 | Fujiwara et al. |
| 9,316,931 B2 * | 4/2016 | Takagi .................. G03G 15/75 |
| 2006/0078809 A1 | 4/2006 | Nagai et al. |
| 2007/0212626 A1 | 9/2007 | Toshine et al. |
| 2011/0092612 A1 | 4/2011 | Miki et al. |
| 2014/0255836 A1 | 9/2014 | Nakata et al. |
| 2014/0255837 A1 | 9/2014 | Nakata et al. |

FOREIGN PATENT DOCUMENTS

| | | | |
|---|---|---|---|
| JP | 2004-2610 A | | 1/2004 |
| JP | 2007-11005 A | | 1/2007 |
| JP | 2007-272191 A | | 10/2007 |
| JP | 2007-272192 A | | 10/2007 |
| JP | 2007-279678 A | | 10/2007 |
| JP | 2008-70761 A | | 3/2008 |
| JP | 2008-170977 A | | 7/2008 |
| JP | 2008-203697 A | | 9/2008 |
| JP | 2010-150425 A | * | 7/2010 |
| JP | 2011-105643 A | * | 6/2011 |
| WO | 2006/121187 A1 | | 11/2006 |
| WO | 2013/011893 A1 | | 1/2013 |

OTHER PUBLICATIONS

Japanese Patent Office J-Plat-Pat machine-assisted English-language translation of Japanese Patent 2011-105643 A (pub. Jun. 2011).*
Japanese Patent Office J-Plat-Pat machine-assisted English-language translation of Japanese Patent 2010-150425 A (pub. Jul. 2010).*
Grant, R. et al., ed., Grant & Hackh's Chemical Dictionary, fifth edition, McGraw-Hill Book Company, NY (1987), p. 271.*
PCT International Search Report and Written Opinion of the International Searching Authority, International Application No. JP2014/056587, Mailing Date Apr. 15, 2014.
Lu, et al., "New ratiometric optical oxygen and pH dual sensors with three emission colors for measuring photosynthetic activity in Cyanobacteria", J. Mater. Chem., vol. 48, 2011, pp. 19293-192301.
International Preliminary Report on Patentability, International Application No. PCT/JP2014/056587, Mailing Date Sep. 17, 2015.
U.S. Appl. No. 14/832,421, filed Aug. 21, 2015. Inventor: Koichi Nakata, et al.

* cited by examiner

ELECTROPHOTOGRAPHIC PHOTOSENSITIVE MEMBER, PROCESS CARTRIDGE, ELECTROPHOTOGRAPHIC APPARATUS, AND CONDENSED POLYCYCLIC AROMATIC COMPOUND

TECHNICAL FIELD

The present invention relates to an electrophotographic photosensitive member, and a process cartridge and an electrophotographic apparatus each including the electrophotographic photosensitive member. The present invention also relates to a novel condensed polycyclic aromatic compound.

BACKGROUND ART

The surface layer of an electrophotographic photosensitive member is required to have wear resistance and chemical stability because stress caused by a series of electrophotographic processes including charging, exposure, development, transfer, and cleaning is repeatedly applied to the surface layer.

A method for improving the wear resistance is, for example, a method involving incorporating a curable resin into the surface layer of the electrophotographic photosensitive member. However, when a surface layer having high wear resistance is provided, the surface layer hardly wears, and hence the surface of the surface layer is hardly refreshed and chemical deterioration is liable to accumulate on the surface. The chemical deterioration is a phenomenon in which a hole transporting substance (hole transporting compound) causes a chemical change owing to the stress caused by the series of electrophotographic processes. The chemical change of the hole transporting substance may be a cause for the occurrence of a phenomenon in which an electrophotographic image output under a high-temperature and high-humidity environment becomes blurred (hereinafter sometimes referred to as "image deletion"). Therefore, the suppression of the image deletion requires the suppression of the chemical change of the hole transporting substance.

A technology involving incorporating an additive into the surface layer together with the hole transporting substance is available as a method for improving the chemical stability of the hole transporting substance. Patent Literature 1 discloses a technology for alleviating the image deletion through the addition of a specific fluorine atom-containing monomer having a polymerizable functional group to the surface layer. Patent Literatures 2 to 4 each disclose a technology for alleviating the image deletion through the addition of a specific amine compound to the surface layer. Patent Literature 5 discloses a technology for alleviating the image deletion through the addition of a specific siloxane compound having a specific polymerizable functional group to the surface layer.

CITATION LIST

Patent Literature

PTL 1: Japanese Patent Application Laid-Open No. 2007-11005
PTL 2: Japanese Patent Application Laid-Open No. 2007-272191
PTL 3: Japanese Patent Application Laid-Open No. 2007-272192
PTL 4: Japanese Patent Application Laid-Open No. 2007-279678
PTL 5: Japanese Patent Application Laid-Open No. 2008-70761

SUMMARY OF INVENTION

Technical Problem

The technologies each involving using an additive of Patent Literatures 1 to 5 are technologies for alleviating the exposure of the hole transporting substance to the stress and are not technologies for improving the chemical stability of the hole transporting substance. In recent years, an improvement in durability of the electrophotographic photosensitive member has been significantly progressed and hence a demand for additional alleviation of the image deletion has been growing. The alleviation of the image deletion requires not only the alleviation of the exposure to the stress but also an improvement in chemical stability of the hole transporting substance itself.

In view of the foregoing, the present invention is directed to providing an electrophotographic photosensitive member which satisfies wear resistance and electrical characteristics, and in which image deletion is satisfactorily suppressed, and a process cartridge and an electrophotographic apparatus each including the electrophotographic photosensitive member. Further, the present invention is directed to providing a condensed polycyclic aromatic compound having high chemical stability.

Solution to Problem

According to one aspect of the present invention, there is provided an electrophotographic photosensitive member comprising: a support; and a photosensitive layer formed on the support, in which a surface layer of the electrophotographic photosensitive member comprises a polymerized product of a hole transporting substance having a reactive functional group, in which, a structure other than the reactive functional group of the hole transporting substance is one of: a structure consisting of a carbon atom and a hydrogen atom; and a structure consisting of a carbon atom, a hydrogen atom and an oxygen atom, the structure other than the reactive functional group of the hole transporting substance comprises a structure which comprises a conjugate structure comprising 24 or more $sp^2$ carbon atoms, and in which, the conjugate structure comprises a condensed polycyclic structure comprising 12 or more $sp^2$ carbon atoms.

According to another aspect of the present invention, there is provided a process cartridge detachably mountable to a main body of an electrophotographic apparatus, in which the process cartridge integrally supports: the above-described electrophotographic photosensitive member; and at least one device selected from the group consisting of a charging device, a developing device, a transferring device, and a cleaning device.

According to further aspect of the present invention, there is provided an electrophotographic apparatus comprising: the above-described electrophotographic photosensitive member; a charging device; an exposing device; a developing device; and a transferring device.

According to still another aspect of the present invention, there is provided a condensed polycyclic aromatic compound comprising one of an acryloyloxy group and a methacryloyloxy group, in which a structure other than the one of the acryloyloxy group and the methacryloyloxy group of the condensed polycyclic aromatic compound is one of: a structure consisting of a carbon atom and a hydrogen atom; and a structure consisting of a carbon atom, a hydrogen atom, and an oxygen atom, the structure other than the one of the acryloyloxy group and the methacryloyloxy group of the condensed polycyclic aromatic compound comprises a structure which comprises a conjugate structure comprising 24 or more $sp^2$ carbon atoms, and in which, the conjugate structure comprises a condensed polycyclic structure comprising 12 or more $sp^2$ carbon atoms.

Advantageous Effects of Invention

As described above, according to the present invention, there is provided the electrophotographic photosensitive member which has good wear resistance and electrical characteristics, and in which image deletion is satisfactorily suppressed, and the process cartridge and the electrophotographic apparatus each including the above-described electrophotographic photosensitive member. Further, according to the present invention, provided is the condensed polycyclic aromatic compound having high chemical stability.

DESCRIPTION OF EMBODIMENTS

Figure 1:
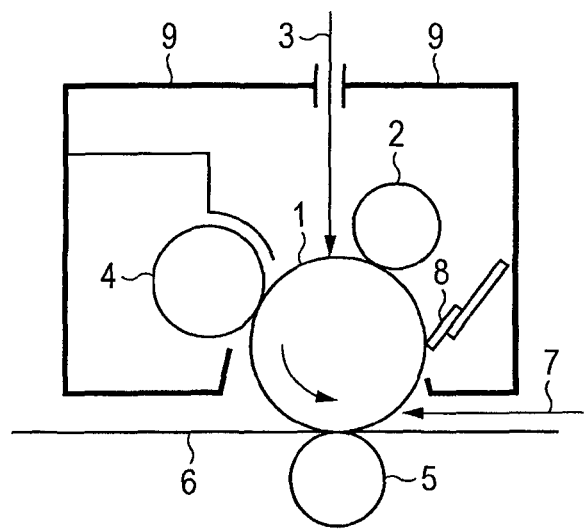
FIG. 1 is a schematic view illustrating an example of a process cartridge including an electrophotographic photosensitive member.

The present invention has features in that: a surface layer contains a polymerized product of a hole transporting substance having a reactive functional group; and the structure other than the reactive functional group of the hole transporting substance is a structure consisting of a carbon atom and a hydrogen atom, or a structure consisting of a carbon atom, a hydrogen atom, and an oxygen atom. In addition to the features, the present invention has features in that the structure other than the reactive functional group of the hole transporting substance is a structure which includes a conjugate structure containing 24 or more $sp^2$ carbon atoms, the conjugate structure includes a condensed polycyclic structure containing 12 or more $sp^2$ carbon atoms. Hereinafter, the hole transporting substance having the reactive functional group, the substance having those features, is sometimes referred to as hole transporting substance of the present invention.

The inventors of the present invention have considered that one cause for the image deletion is that the amine structure of the hole transporting substance to be incorporated into the surface layer of an ordinary electrophotographic photosensitive member causes a chemical change. In view of the foregoing, the inventors of the present invention have searched for a hole transporting substance for the electrophotographic photosensitive member independent of an amine structure, and have reached the present invention.

An amine compound such as an arylamine compound has been used as the hole transporting substance to be used in an electrophotographic photosensitive member in order that hole transportability may be secured. The term "hole transportability" as used in the present invention means that the substance has a hole transporting performance, and a measure of the hole transporting performance can be known by evaluating the electrophotographic photosensitive member for its electrical characteristics such as a residual potential and sensitivity.

The hole transportability of the arylamine compound may be expressed by the electron-donating property of its amine structure due to the interaction of an aryl group around its nitrogen atom or a group formed of a group of carbon atoms each having an $sp^2$ electron orbital (hereinafter sometimes referred to as "$sp^2$ carbon atoms"). Meanwhile, its arylamine moiety may be in a state susceptible to a chemical reaction or the like because the exchange of holes is vigorously performed through a repeated electrophotographic process. In particular, the moiety may tend to be susceptible to a change such as oxidation caused by: discharge energy in a charging step; or the action of ozone or an oxidizing substance produced by a discharge phenomenon. The chemical change of the arylamine moiety is assumed to be caused as a result of the foregoing.

As a result of their extensive studies, the inventors of the present invention have found that the use of the polymerized product of the hole transporting substance of the present invention in the surface layer satisfies wear resistance and electrical characteristics, and has a suppressing effect on the image deletion. A possible reason for the foregoing is that the susceptibility of the hole transporting substance of the present invention to a chemical change is reduced as compared with that of the arylamine compound because the hole transporting substance of the present invention does not have an arylamine structure, specifically, does not have a nitrogen atom.

The structure other than the reactive functional group of the hole transporting substance of the present invention includes a structure which includes a conjugate structure containing 24 or more $sp^2$ carbon atoms, and the conjugate structure includes a condensed polycyclic structure containing 12 or more $sp^2$ carbon atoms from the viewpoint of the hole transporting performance. A conjugate structure having 28 or more $sp^2$ carbon atoms is preferred. The term "conjugate structure" means a structure in which $sp^2$ carbon atoms are continuously bonded. The conjugate structure has the following property: the structure promotes the delocalization of electrons in molecules to facilitate the exchange of charges between the molecules. The term "condensed polycyclic structure" as used in the present invention means a structure in which two or more cyclic structures like a benzene ring are adjacent to each other (condensed polycyclic aromatic structures).

The number of the $sp^2$ carbon atoms is preferably 120 or less, more preferably 60 or less from the viewpoints of, for example, a film forming ability, compatibility with a peripheral material, and film strength.

The number of the $sp^2$ carbon atoms forming one condensed polycyclic structure is preferably 14 or more, more preferably 16 or more in order that an additionally good hole transporting performance may be expressed.

The number of the sp² carbon atoms forming each condensed polycyclic structure is preferably 20 or less, more preferably 18 or less from the viewpoints of the film forming ability and the compatibility with the peripheral material.

With regard to a ring structure forming each condensed polycyclic structure, it is suitable that a conjugate structure spreads in a planar manner. Therefore, the condensed polycyclic structure is preferably formed of a five-membered ring or a six-membered ring in order that a planar structure may be formed. The number of the ring structures forming the condensed polycyclic structure, which is 2 or more, is preferably 3 or more in order that the hole transporting performance may be made additionally suitable.

In addition, with regard to the number of the ring structures forming each condensed polycyclic structure, the condensed polycyclic structure is preferably formed of 6 or less rings and is more preferably formed of 5 or less rings from the viewpoints of film formability and the flexibility of the molecule. That is, a condensed polycyclic structure formed of 3 or 4 rings is most preferred.

The hole transporting substance of the present invention has at least one unit (one) of the condensed polycyclic structure as a partial structure. The hole transporting substance preferably has two or more units of the condensed polycyclic structures and more preferably has three or more units of the condensed polycyclic structures from the viewpoint of expressing an additionally good hole transporting performance. In addition, the number of the units of the condensed polycyclic structures in one molecule of the hole transporting substance is preferably 10 or less, more preferably 4 or less.

When the hole transporting substance has two or more of those condensed polycyclic structures, the substance preferably has a structure in which the condensed polycyclic structures are bonded to each other through a single bond (the condensed polycyclic structures are directly bonded to each other) from the viewpoint of stability against a chemical change.

In addition, from the viewpoints of having a high hole transporting performance and a high suppressing effect on the image deletion, the condensed polycyclic structure is preferably fluorene, anthracene, phenanthrene, fluoranthene, or pyrene, more preferably fluorene, anthracene, or pyrene. Any such condensed polycyclic structure may have a substituent.

It should be noted that an sp² carbon atom in the reactive functional group is not included in the number of the sp² carbon atoms of the hole transporting substance of the present invention. For example, an sp² carbon atom in the double bond or carbonyl group of an acryloyloxy group or methacryloyloxy group as an example of the reactive functional group is not included. An sp² carbon atom in a reactive phenol group is also not included.

The reactive functional group means a functional group capable of bonding molecules each having the reactive functional group through a covalent bond when a reaction occurs between the molecules. Examples thereof include the following reactive functional groups.

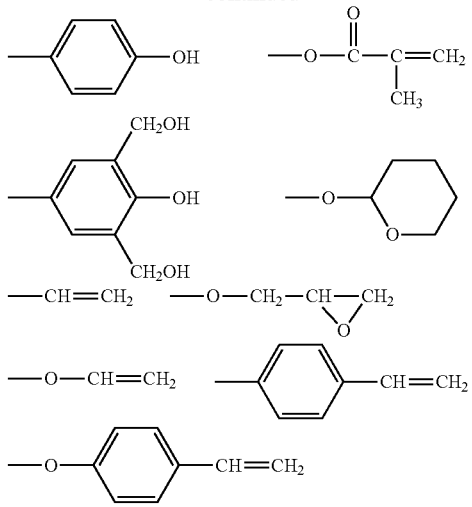

The reactive functional group is preferably an acryloyloxy group or a methacryloyloxy group from the viewpoint of the wear resistance of the surface layer.

In addition, different reactive functional groups may exist in one molecule of the hole transporting substance, or reactive functional groups may be different between molecules thereof.

A method for applying energy such as UV light, an electron beam, or heat, or a method for causing an auxiliary agent such as a polymerization initiator and a compound such as an acid, an alkali, or a complex to coexist can be employed as a method for subjecting the reactive functional group to a polymerization reaction.

The hole transporting substance of the present invention is preferably such that a compound obtained by substituting the reactive functional group of the hole transporting substance with a hydrogen atom is a compound represented by the following formula (1).

The molecular structure of the hole transporting substance of the present invention can be roughly classified into the structure of the reactive functional group and the structure other than the reactive functional group. The structure of the reactive functional group is, for example, the structure of the reactive functional group exemplified in the foregoing. The structure other than the reactive functional group means a structure obtained by subtracting the structure of the reactive functional group from the molecular structure of the hole transporting substance. Here, when the structure of the reactive functional group is simply subtracted from the molecular structure of the hole transporting substance, a covalent bond remains in a linking portion between the reactive functional group and the structure other than the reactive functional group. A structure obtained by bonding a hydrogen atom to the remaining covalent bond means the compound obtained by substituting the reactive functional group with the hydrogen atom.

(1)

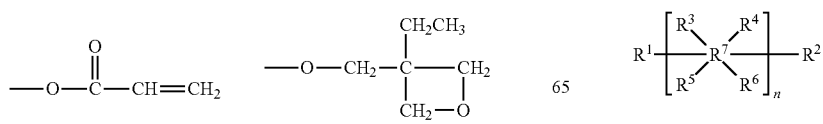

Groups represented by $R^1$ to $R^6$ of the formula (1) each independently represent a hydrogen atom, a substituted or unsubstituted alkyl group, a substituted or unsubstituted alkoxy group, a substituted or unsubstituted aralkyl group, or a substituted or unsubstituted aryl group. $R^7$ represents a group derived from a substituted or unsubstituted arene by loss of 6 hydrogen atoms. n represents an integer of 1 to 10, and when n represents 2 to 10, partial structures each represented by the following formula (2) in the formula (1) may be identical to or different from each other.

Examples of the alkyl group include a methyl group, an ethyl group, an n-propyl group, an isopropyl group, an n-butyl group, an isobutyl group, a sec-butyl group, a tert-butyl group, an n-pentyl group, an isopentyl group, a neopentyl group, a tert-pentyl group, a cyclopentyl group, an n-hexyl group, a 1-methylpentyl group, a 4-methyl-2-pentyl group, a 3,3-dimethylbutyl group, a 2-ethylbutyl group, a cyclohexyl group, a 1-methylhexyl group, a cyclohexylmethyl group, a 4-tert-butylcyclohexyl group, an n-heptyl group, a cycloheptyl group, an n-octyl group, a cyclooctyl group, a tert-octyl group, a 1-methylheptyl group, a 2-ethylhexyl group, a 2-propylpentyl group, an n-nonyl group, a 2,2-dimethylheptyl group, a 2,6-dimethyl-4-heptyl group, a 3,5,5-trimethylhexyl group, an n-decyl group, an n-undecyl group, a 1-methyldecyl group, an n-dodecyl group, an n-tridecyl group, a 1-hexylheptyl group, an n-tetradecyl group, an n-pentadecyl group, an n-hexadecyl group, an n-heptadecyl group, an n-octadecyl group, and an n-eicosyl group.

Examples of the alkoxy group include a methoxy group, an ethoxy group, an n-propoxy group, an isopropoxy group, an n-butoxy group, an isobutoxy group, a sec-butoxy group, and a tert-butoxy group.

Examples of the aralkyl group include a benzyl group, a phenethyl group, an α-methylbenzyl group, an α,α-dimethylbenzyl group, a 1-naphthylmethyl group, a 2-naphthylmethyl group, an anthracenylmethyl group, a phenanthrenylmethyl group, a pyrenylmethyl group, a furfuryl group, a 2-methylbenzyl group, a 3-methylbenzyl group, a 4-methylbenzyl group, a 4-ethylbenzyl group, a 4-isopropylbenzyl group, a 4-tert-butylbenzyl group, a 4-n-hexylbenzyl group, a 4-n-nonylbenzyl group, a 3,4-dimethylbenzyl group, a 3-methoxybenzyl group, a 4-methoxybenzyl group, a 4-ethoxybenzyl group, a 4-n-butyloxybenzyl group, a 4-n-hexyloxybenzyl group, and a 4-n-nonyloxybenzyl group.

Examples of the aryl group include: a phenyl group, a biphenylyl group, a naphthyl group, a fluorenyl group, an anthracenyl group, a phenanthrenyl group, a fluoranthenyl group, a pyrenyl group, a triphenylenyl group; a monovalent group derived from tetracene; a monovalent group derived from chrysene; a monovalent group derived from pentacene; a monovalent group derived from acenaphthene; an acenaphthylenyl group; a monovalent group derived from perylene; a monovalent group derived from corannulene; and a monovalent group derived from coronene. Further, the aryl group may be a compound with structure in which those condensed polycyclic structures each having a conjugate structure are linked to each other directly or through a conjugated double bond group.

$R^7$ of the formula (1) represents a group obtained by removing 6 hydrogen atoms from a substituted or unsubstituted arene. An arene with structure in which multiple rings typified by a benzene structure further linked can be applied as the structure of the arene in $R^7$. Of such arene structures, a condensed polycyclic structure having a conjugate structure and having a planar structure is suitable as described above. The following structure is preferred as the arene structure: a benzene structure, a naphthalene structure, a fluorene structure, an anthracene structure, a phenanthrene structure, a fluoranthene structure, a pyrene structure, a triphenylene structure, a tetracene structure, a chrysene structure, a pentacene structure, an acenaphthene structure, an acenaphthylene structure, a perylene structure, a corannulene structure, a coronene structure, or the like. Further, the arene structure may be a structure in which these arenes are linked to each other directly or through a conjugated double bond group. Of those structures, the following structures are particularly suitable: a fluorene structure, an anthracene structure, a phenanthrene structure, a fluoranthene structure, and a pyrene structure.

n of the formula (1) represents an integer of 1 to 10. A conjugate system preferably spreads and n is preferably as large as possible from the viewpoint of the hole transportability. Specifically, n falls within the range of preferably 1 or more and 6 or less, more preferably 1 or more and 4 or less. With regard to a suitable value for a molecular weight, a compound having a molecular weight of 300 or more and 3,000 or less is preferred. When the molecular weight falls within the range, conjugation in a molecule spreads and hence a hole transporting performance improves.

In addition, when n represents 2 or more, a structure in which $R^7$ are linked to each other is established. In this case, the arene structures of $R^7$ may be directly bonded to each other or may be bonded through a carbon atom. It is preferred that the arene structures be directly bonded to each other.

It is preferred that at least one of $R^1$ to $R^7$ described above represent the condensed polycyclic structure, and it is more preferred that two or more thereof each represent the condensed polycyclic structure.

When n represents 2 to 10, the partial structures each represented by the following formula (2) in the formula (1) may be identical to or different from each other.

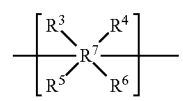

(2)

A substituent which $R^1$ to $R^7$ may each have is a linear or branched alkyl group, aralkyl group, alkoxy group, or hydroxyalkyl group. A substituent obtained by multiply combining those substituents is also permitted, and any such substituent can be introduced to an arbitrary substitution position at which substitution can occur.

A condensed polycyclic aromatic compound having high chemical stability is, for example, the following compound: a condensed polycyclic aromatic compound having an acryloyloxy group or a methacryloyloxy group. Further, the structure other than the acryloyloxy group or methacryloyloxy group of the condensed polycyclic aromatic compound is a structure consisting of a carbon atom and a hydrogen atom, or a structure consisting of a carbon atom, a hydrogen atom, and an oxygen atom. In addition, the condensed polycyclic aromatic compound has features in that the structure other than the acryloyloxy group or methacryloyloxy group of the condensed polycyclic aromatic compound is a structure which includes a conjugate structure containing 24 or more $sp^2$ carbon atoms, and the conjugate structure includes a condensed polycyclic structure containing 12 or more $sp^2$ carbon atoms.

An sp³ carbon atom may be caused to exist at a moderate ratio in the hole transporting substance of the present invention by appropriately selecting the substituent.

Compound examples of the hole transporting substance of the present invention are shown below; provided that the present invention is not limited thereto. The reactive functional groups of the following Exemplified Compounds No. 1 to No. 182 may each be substituted with any one of the reactive functional groups described above. Similarly, the substituents thereof may each be substituted with any one of the substituents described above.

No. 1
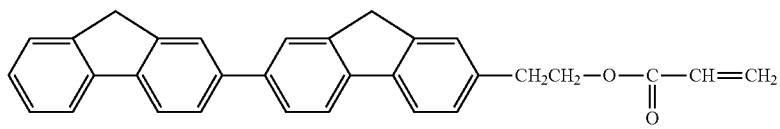

No. 2
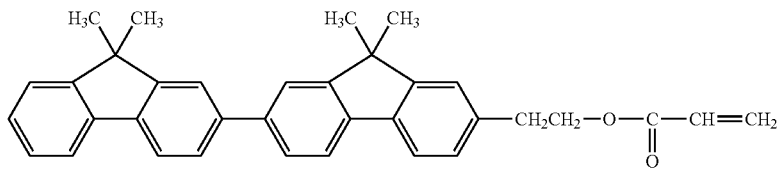

No. 3
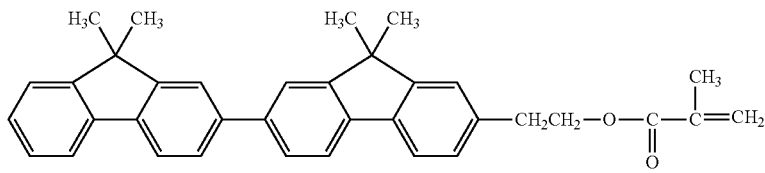

No. 4
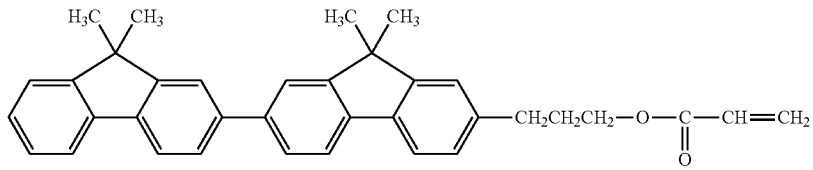

No. 5
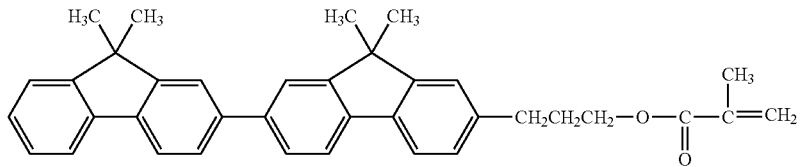

No. 6
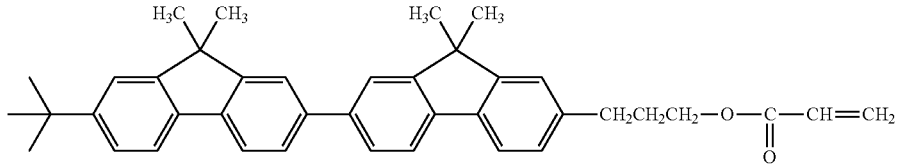

No. 7
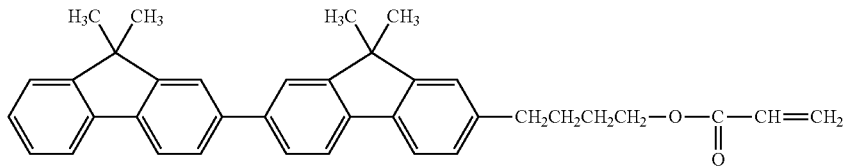

No. 8
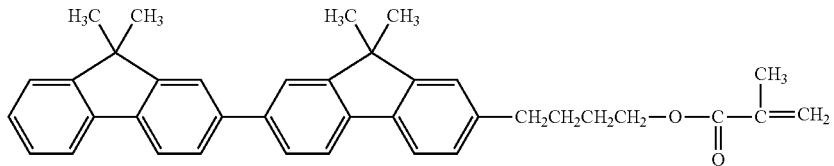

-continued
No. 9
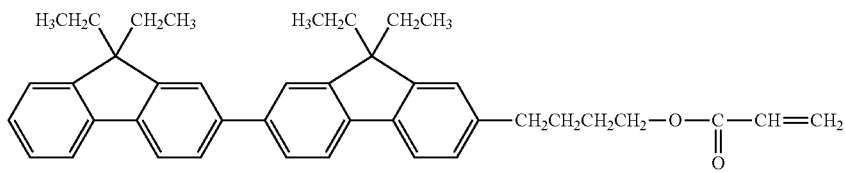
No. 10
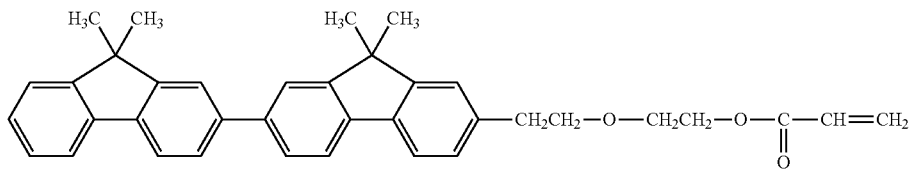
No. 11
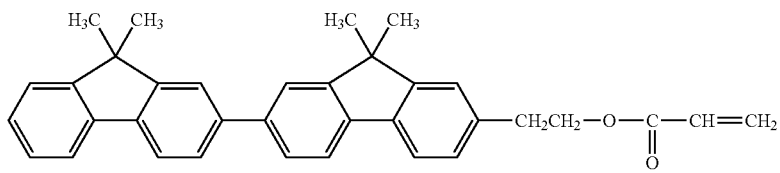
No. 12
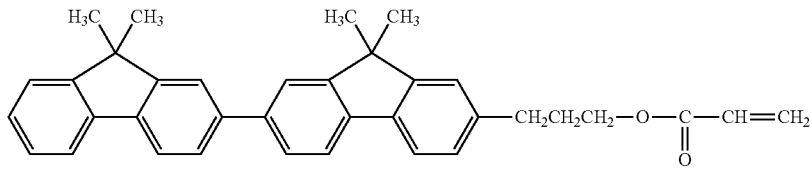
No. 13
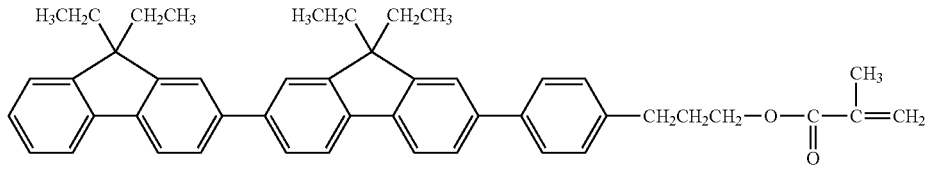
No. 14
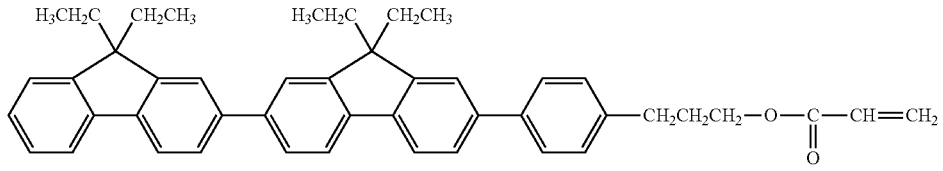
No. 15
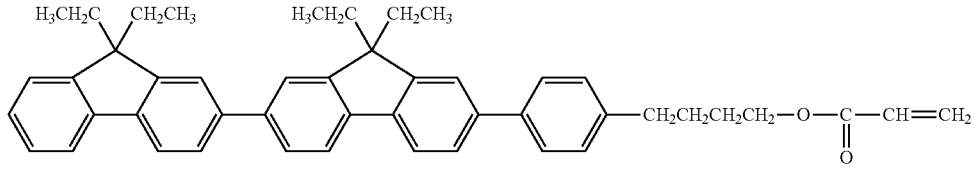
No. 16
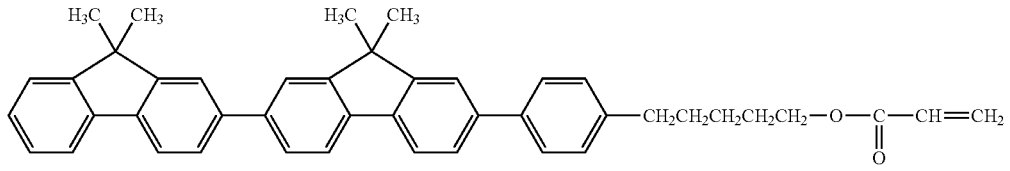
No. 17
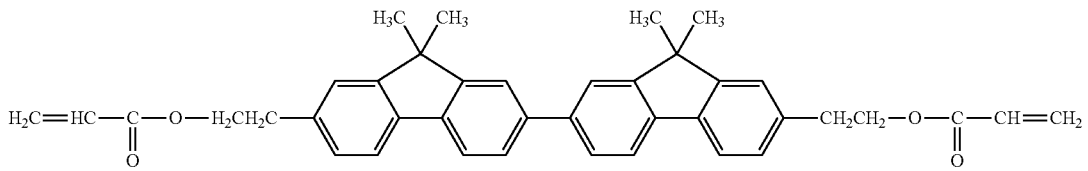

-continued
No. 18
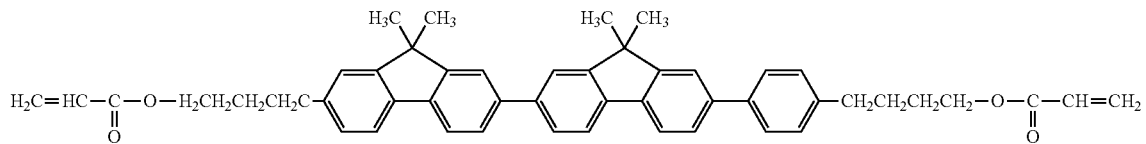
No. 19
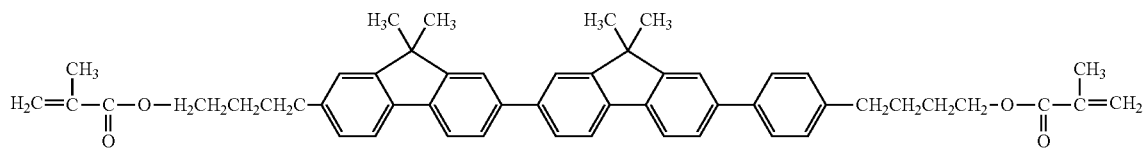
No. 20
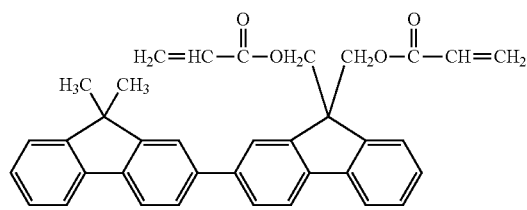
No. 21
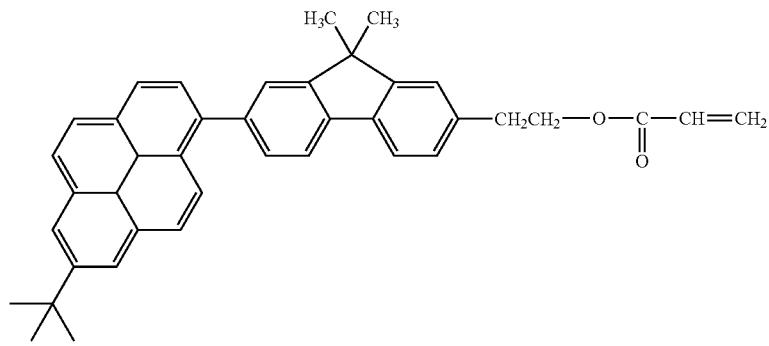
No. 22
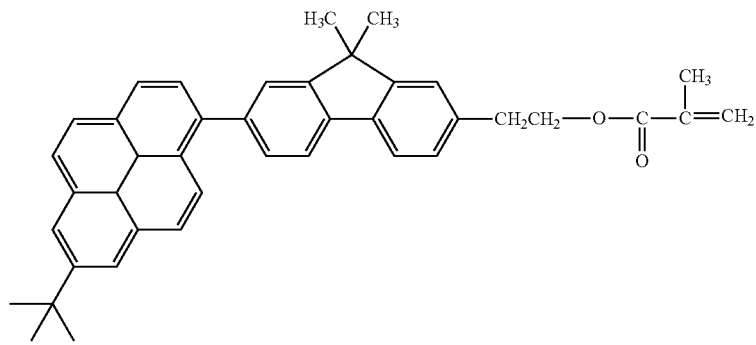
No. 23
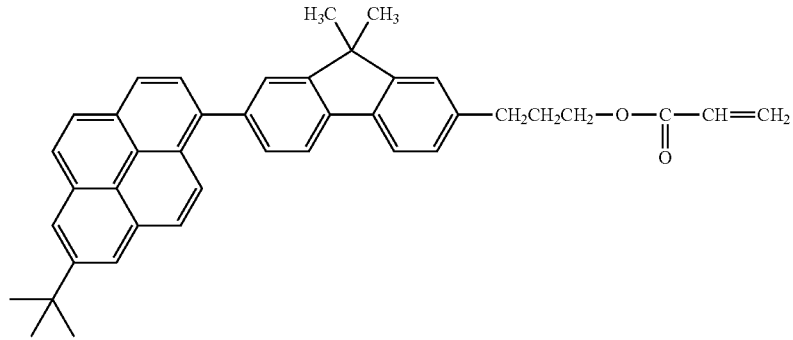

No. 24
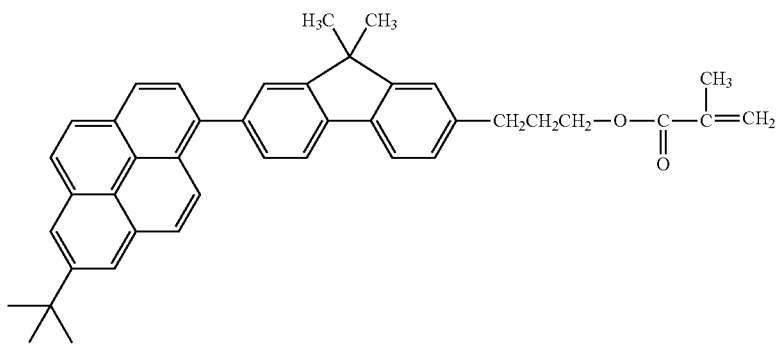
No. 25
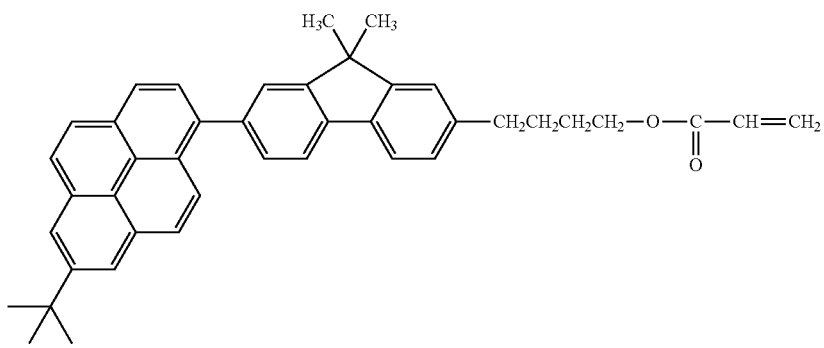
No. 26
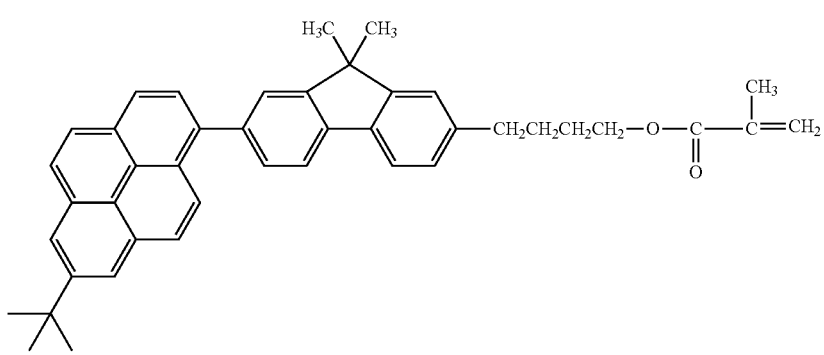
No. 27
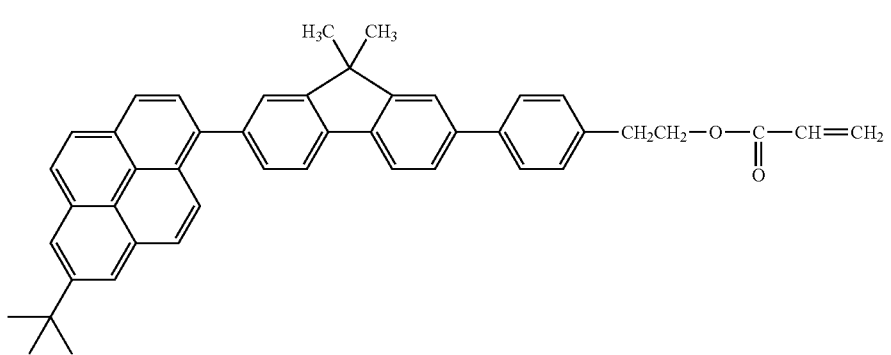

-continued
No. 28
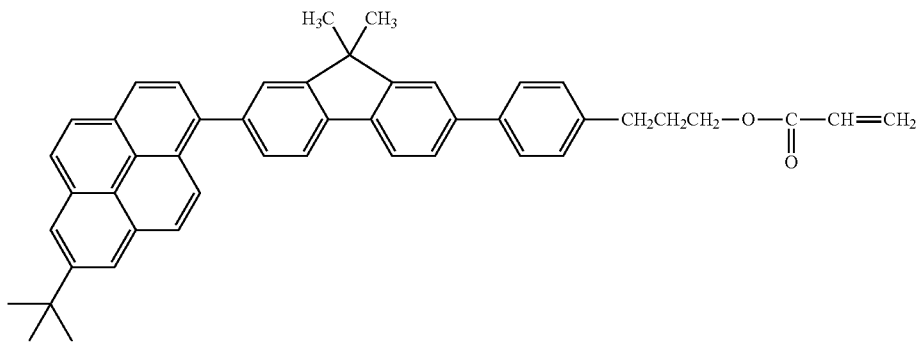
No. 29
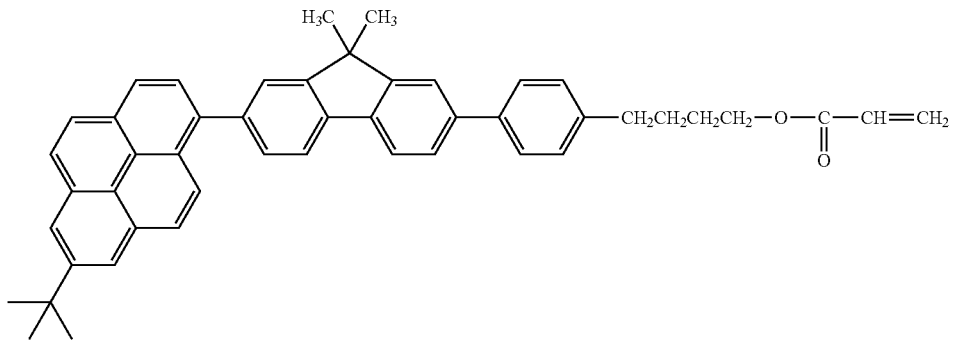
No. 30
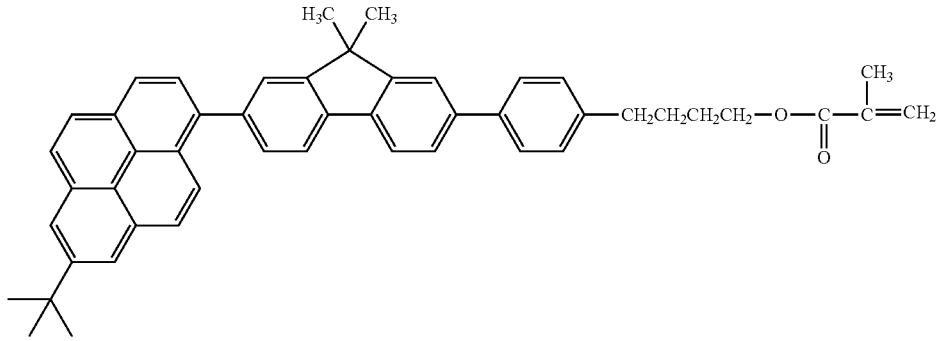
No. 31
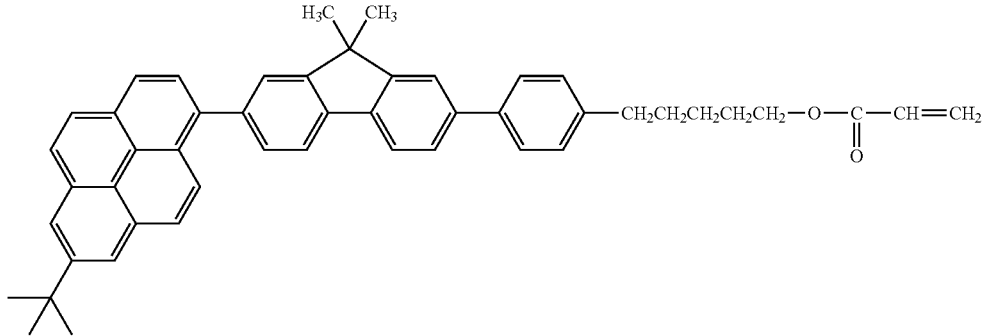
No. 32
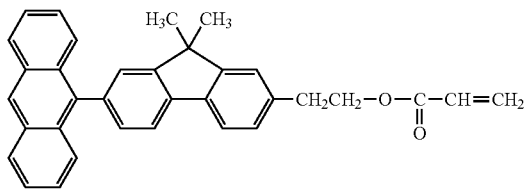
No. 33
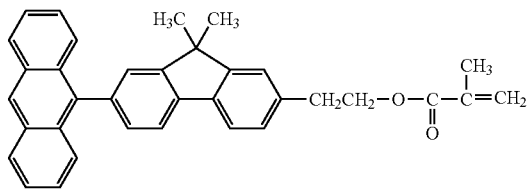

-continued
No. 34
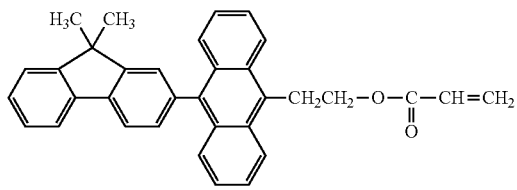
No. 35
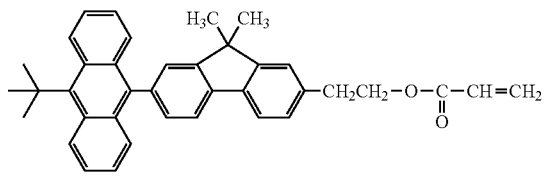
No. 36
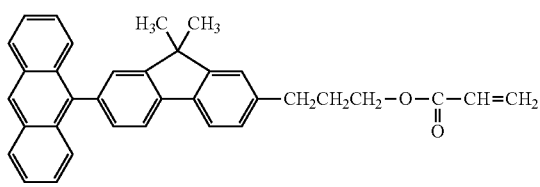
No. 37
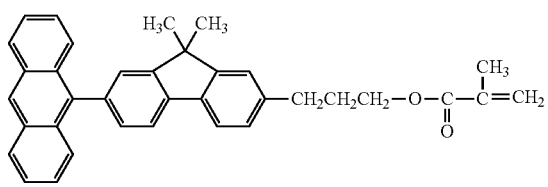
No. 38
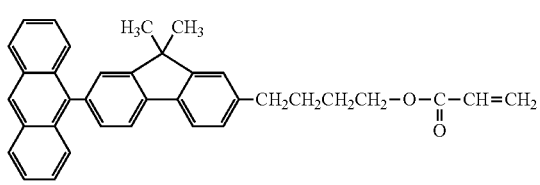
No. 39
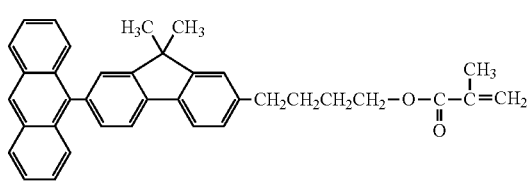
No. 40
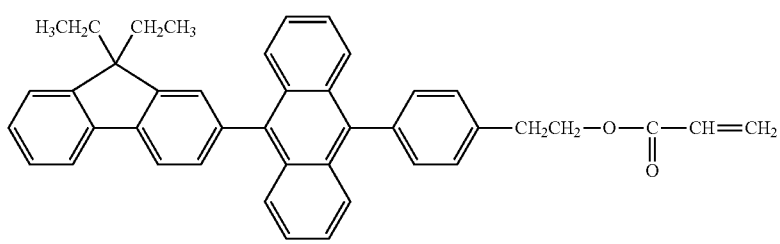
No. 41
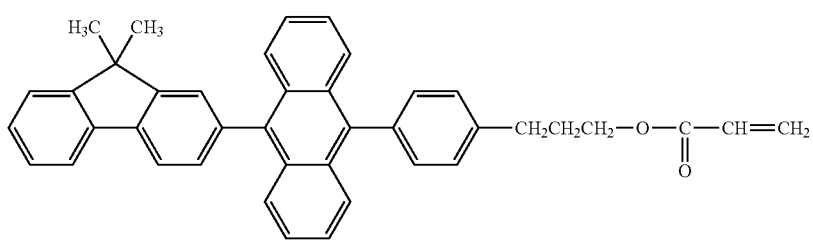
No. 42
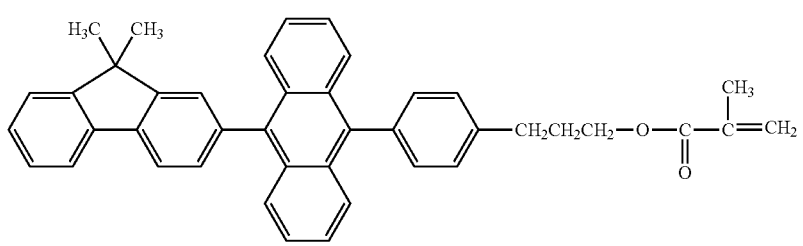
No. 43
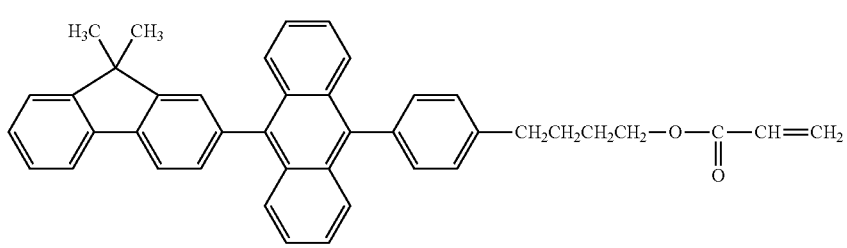

-continued
No. 44
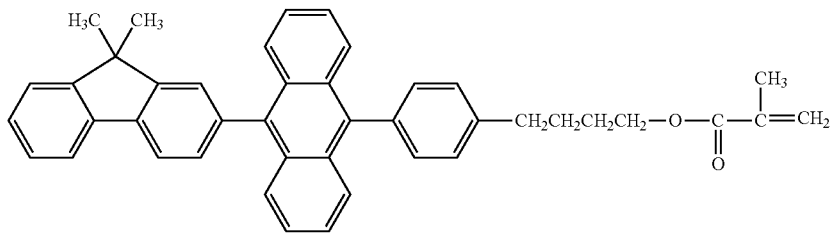
No. 45
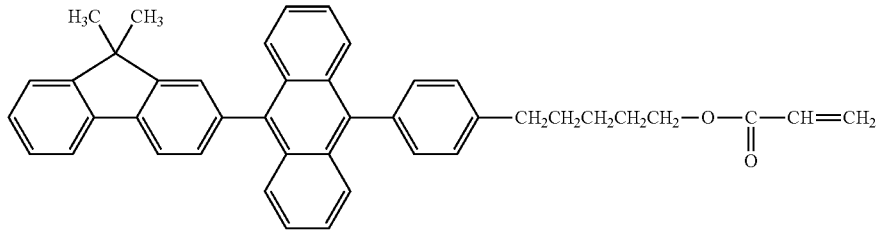
No. 46
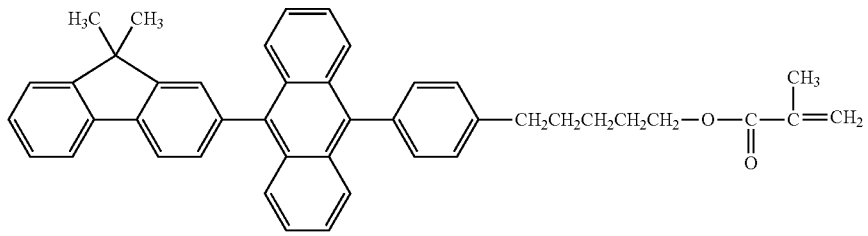
No. 47
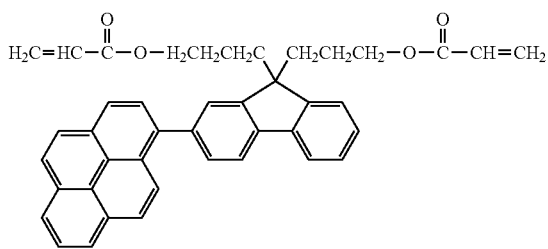
No. 48
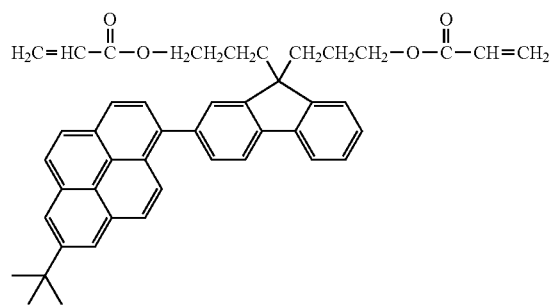
No. 49
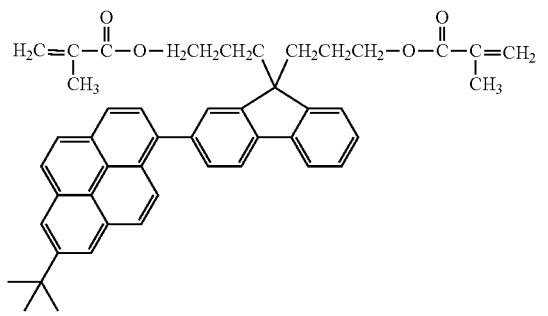
No. 50
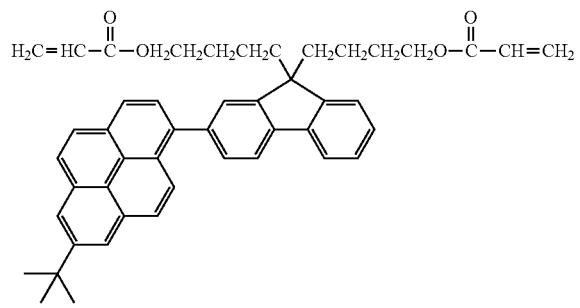

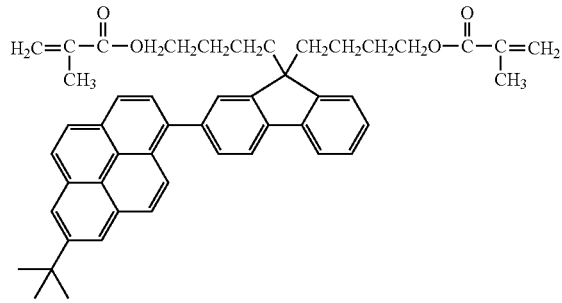
No. 51
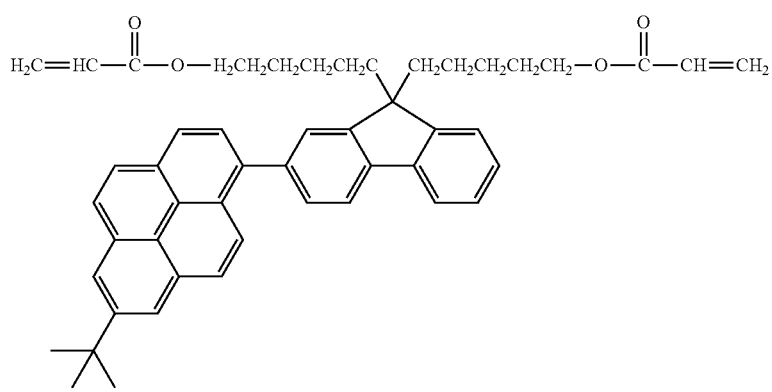
No. 52
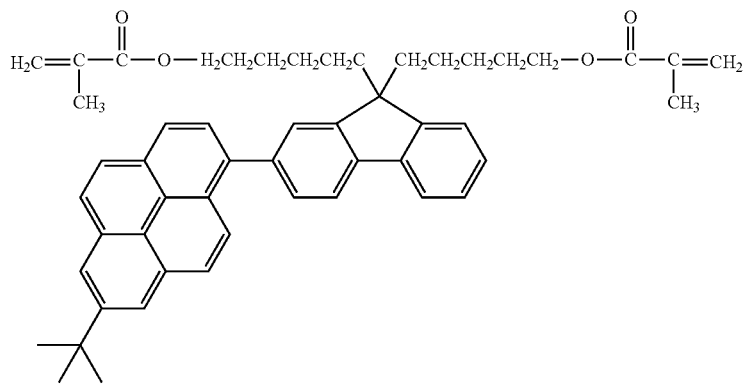
No. 53
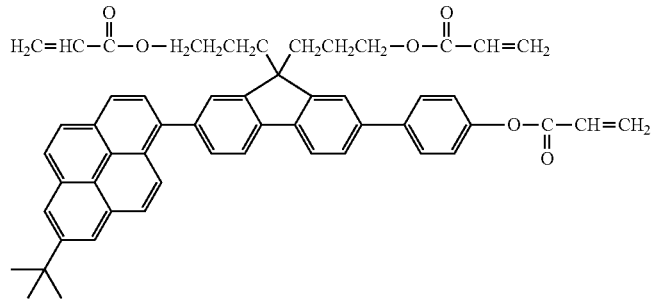
No. 54

-continued
No. 55
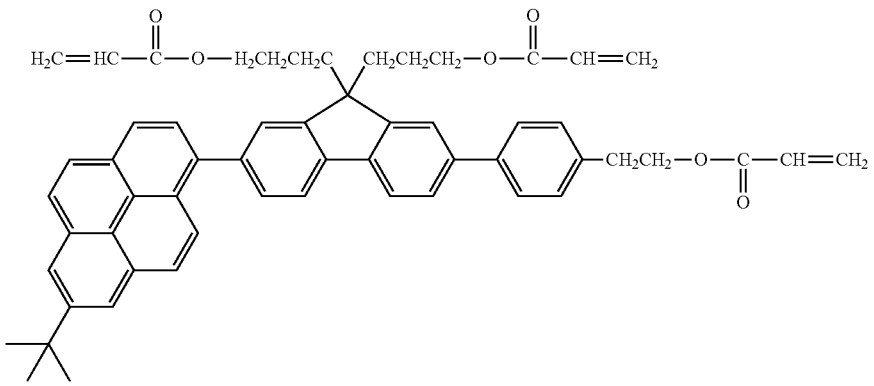
No. 56
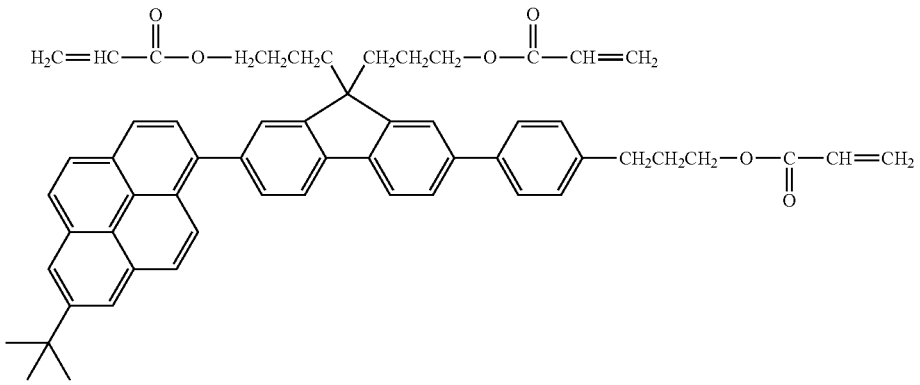
No. 57
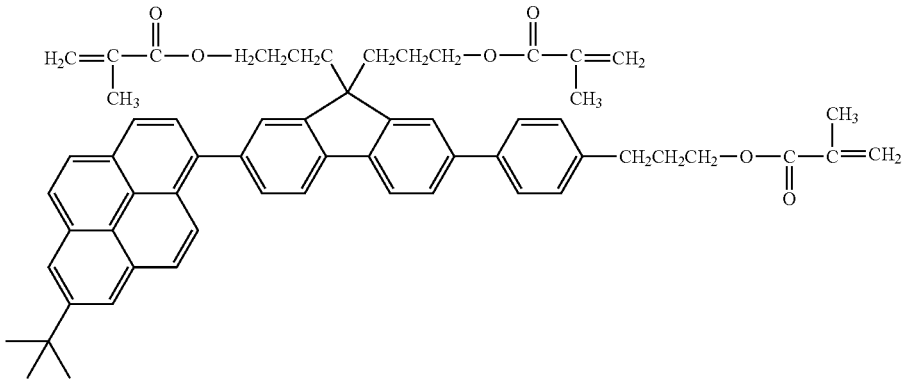
No. 58
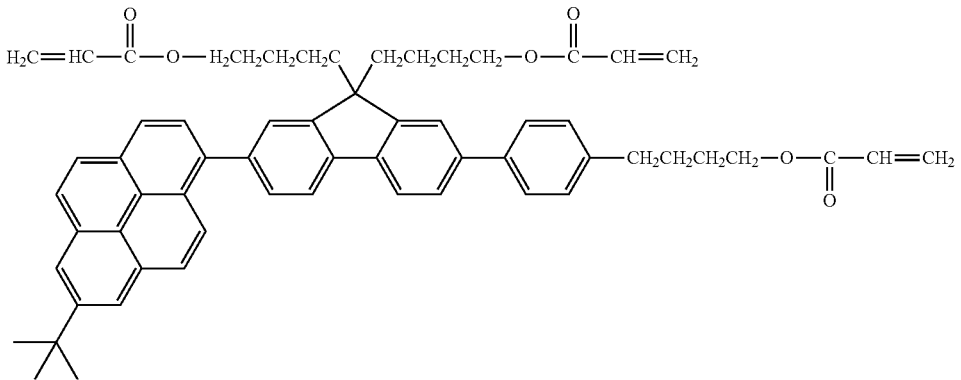

-continued
No. 59
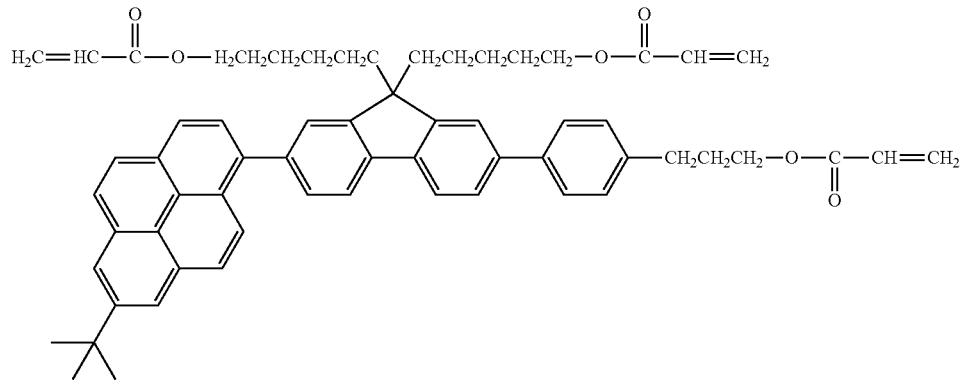
No. 60
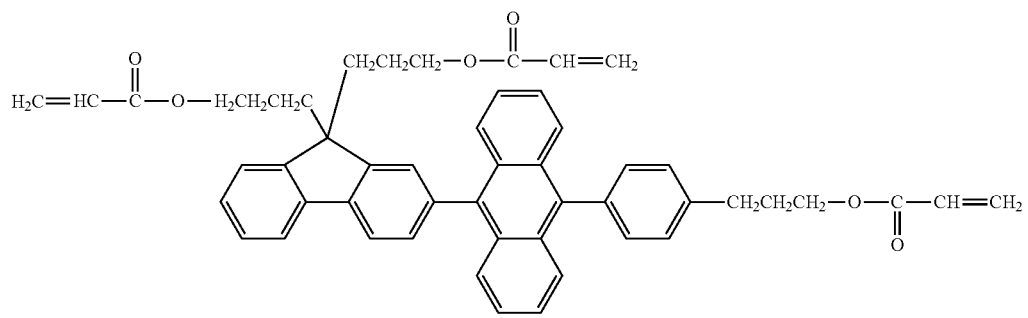
No. 61
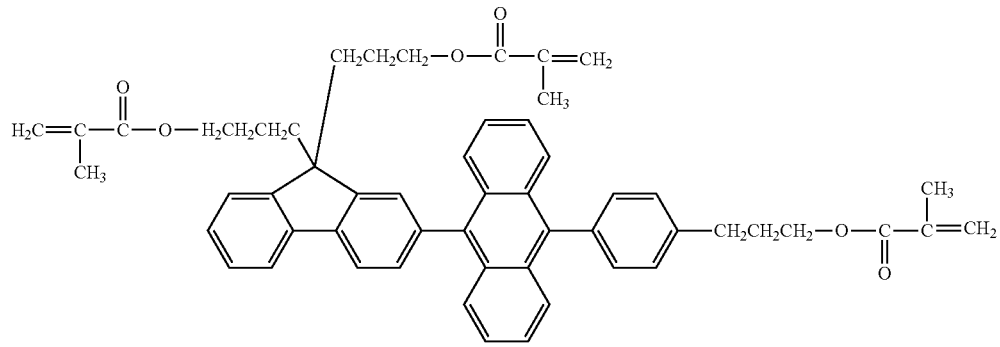
No. 62
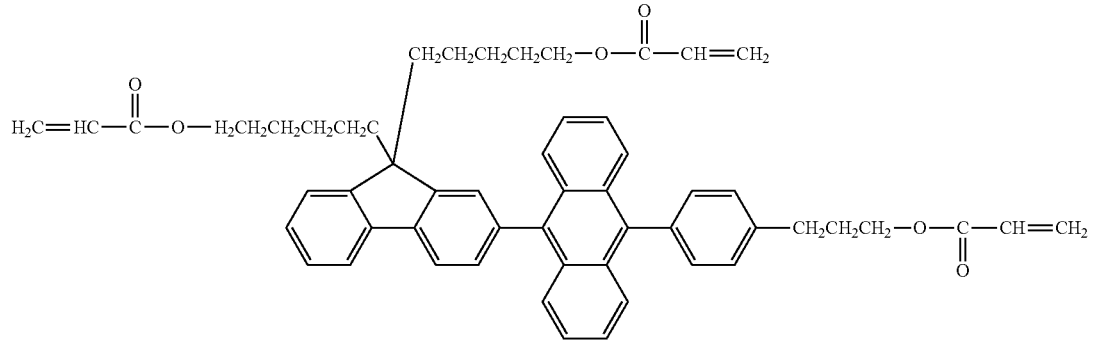

No. 63
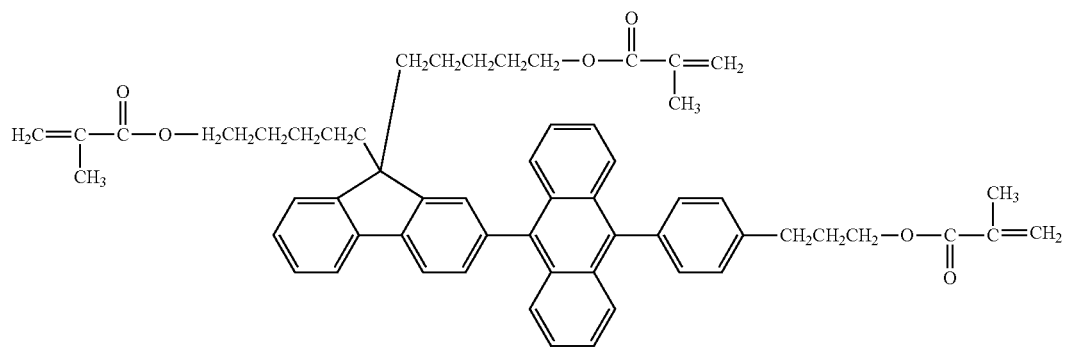
No. 64
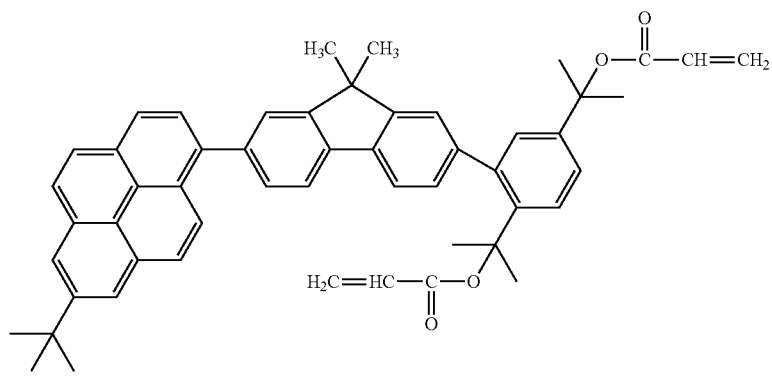
No. 65
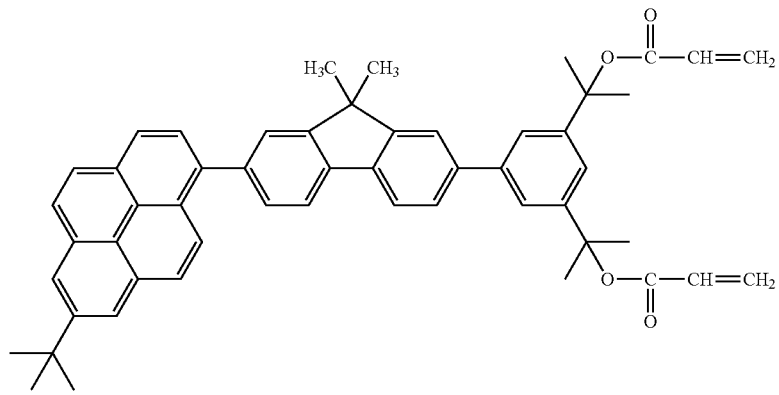
No. 66
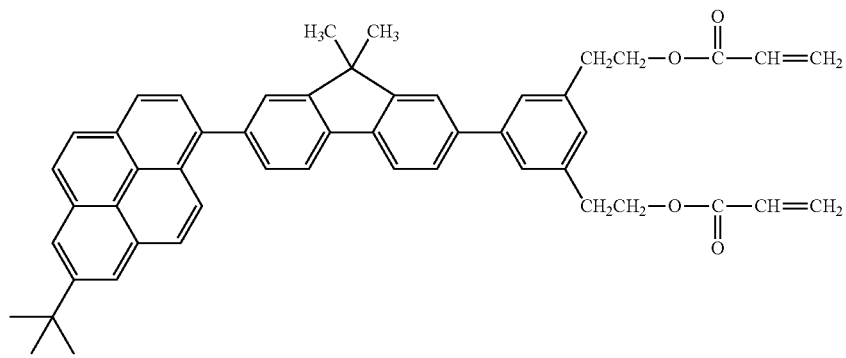

-continued
No. 67
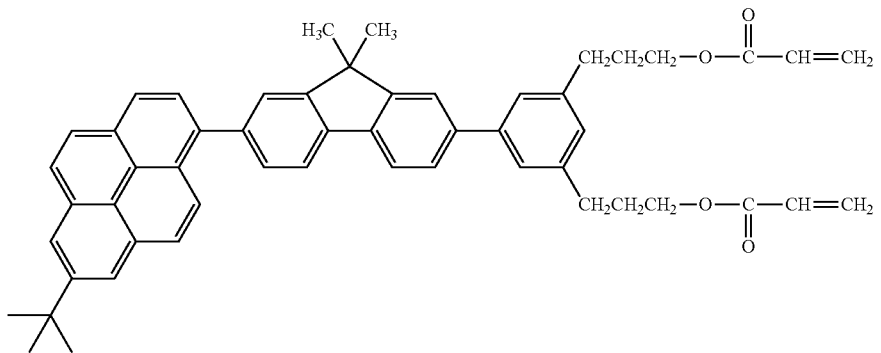
No. 68
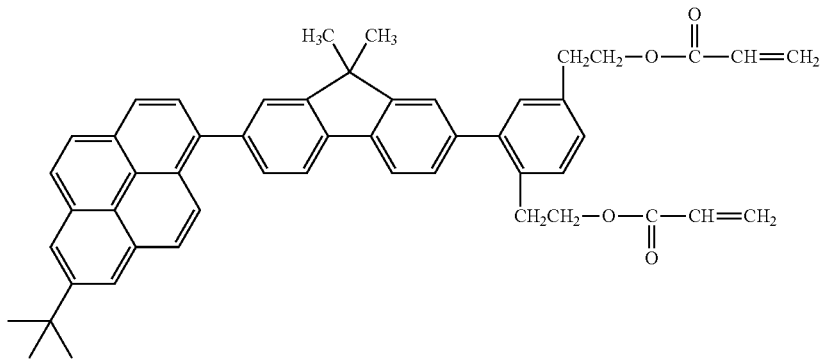
No. 69
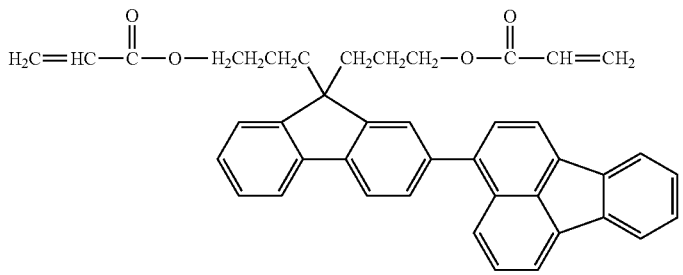
No. 70
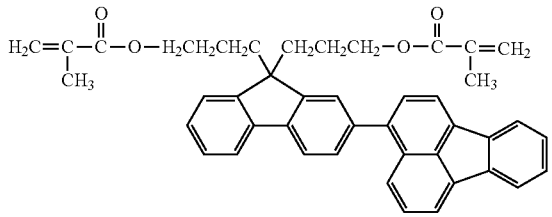
No. 71
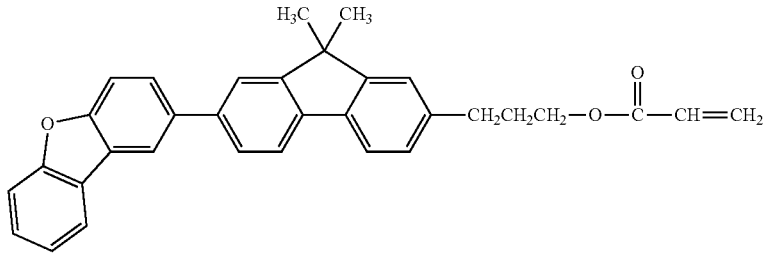

-continued
No. 72
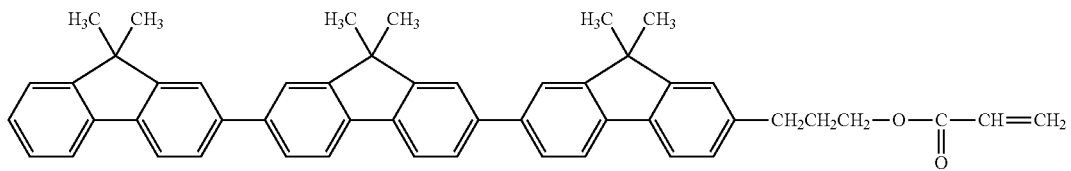
No. 73
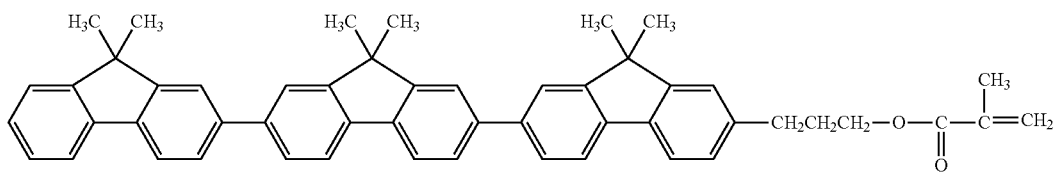
No. 74
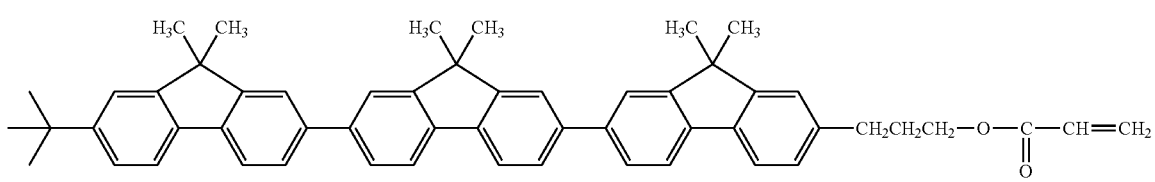
No. 75
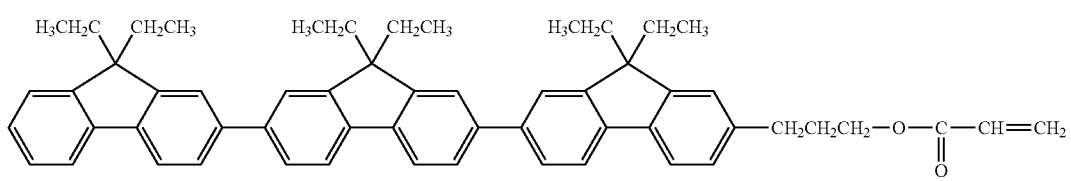
No. 76
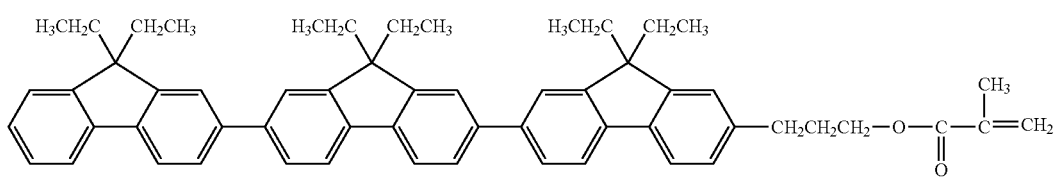
No. 77
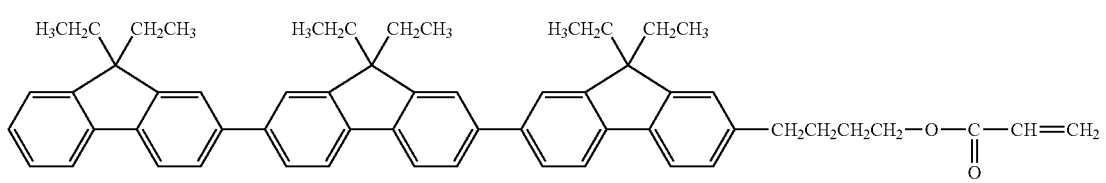
No. 78
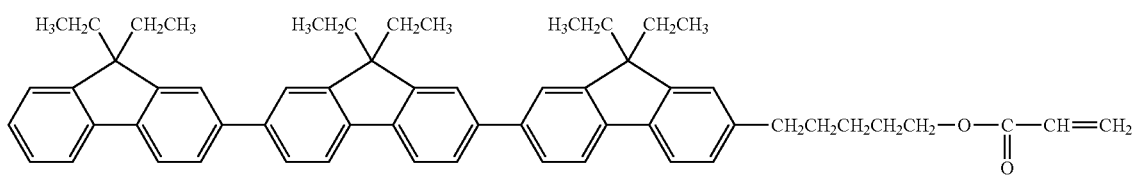
No. 79
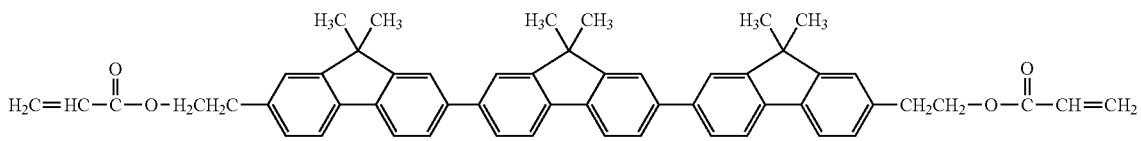

-continued
No. 80
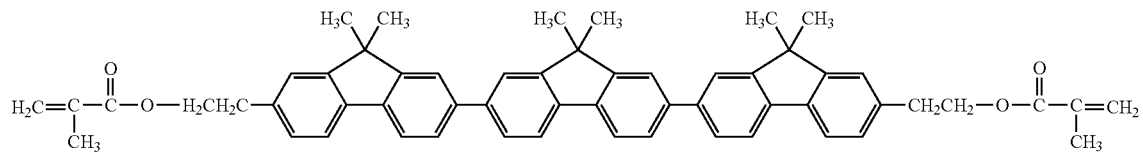
No. 81
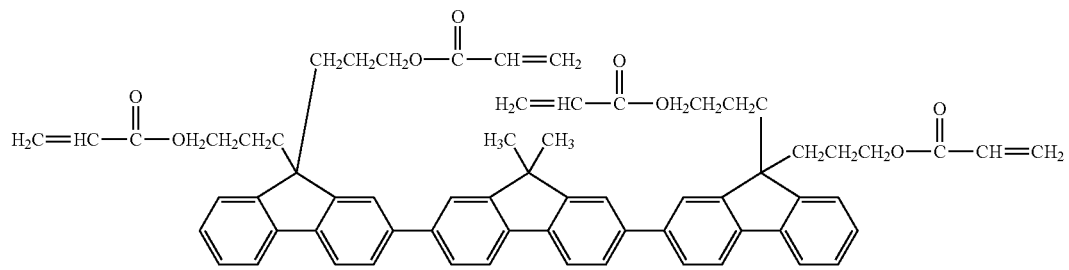
No. 82
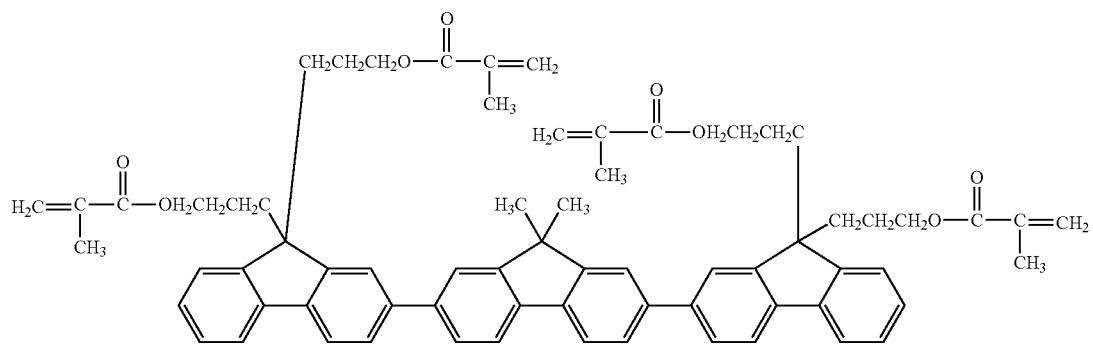
No. 83
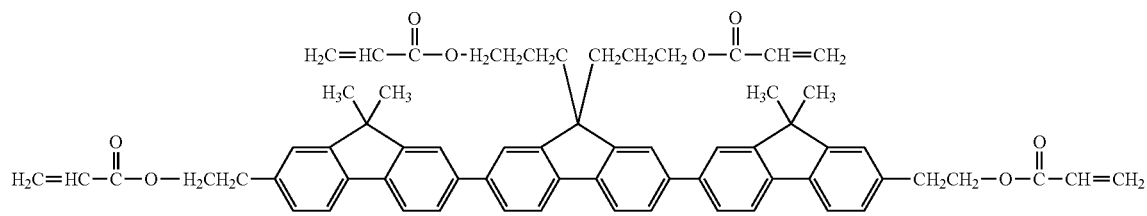
No. 84
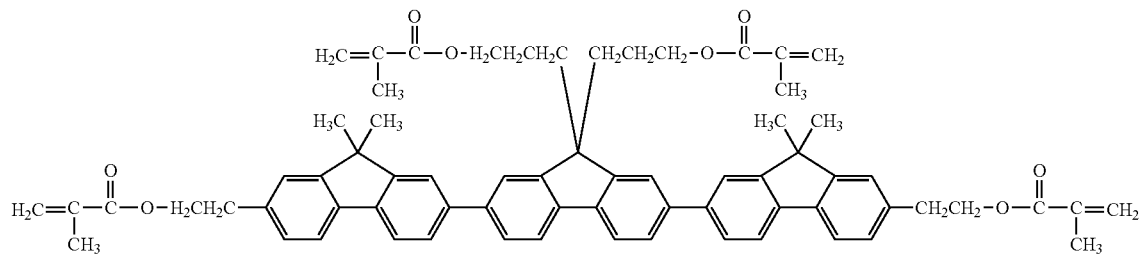

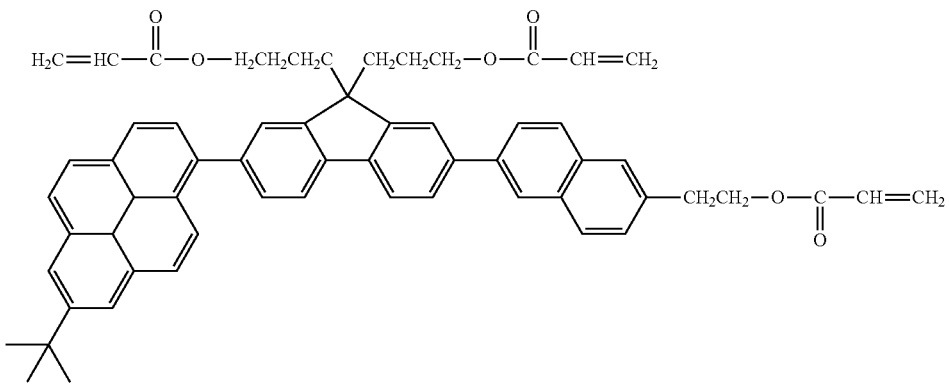
No. 85
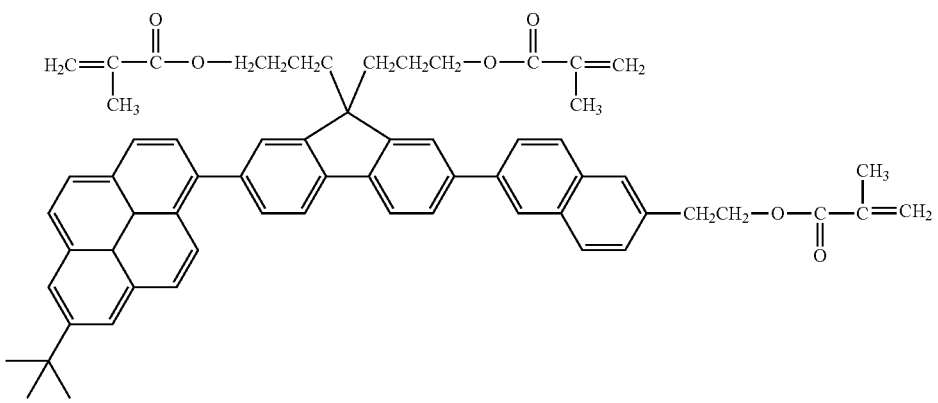
No. 86
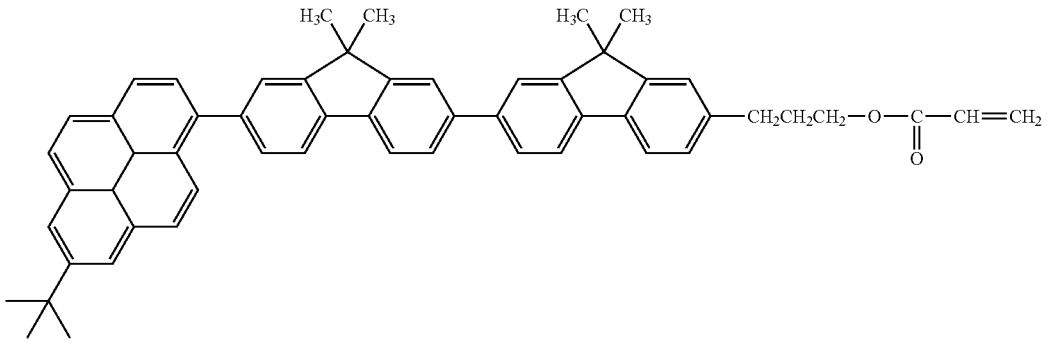
No. 87
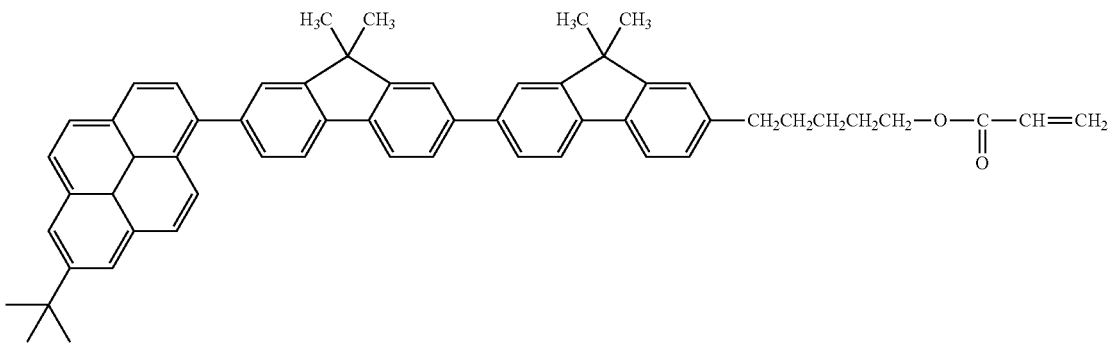
No. 88

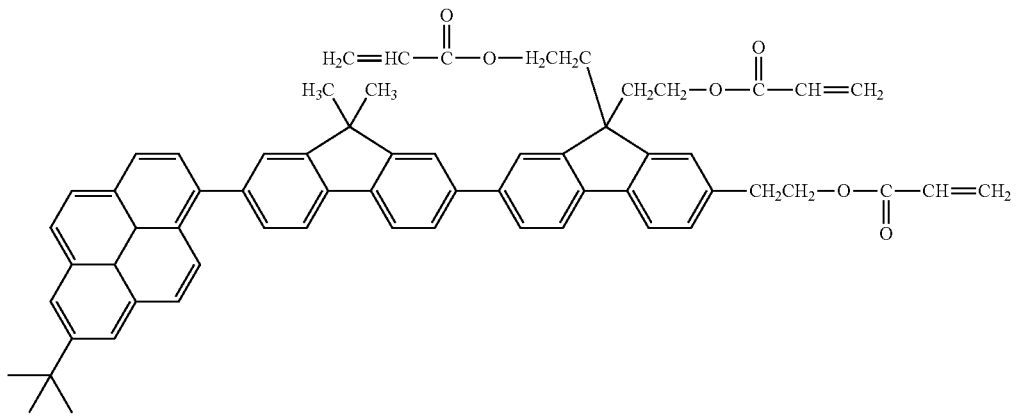
No. 89
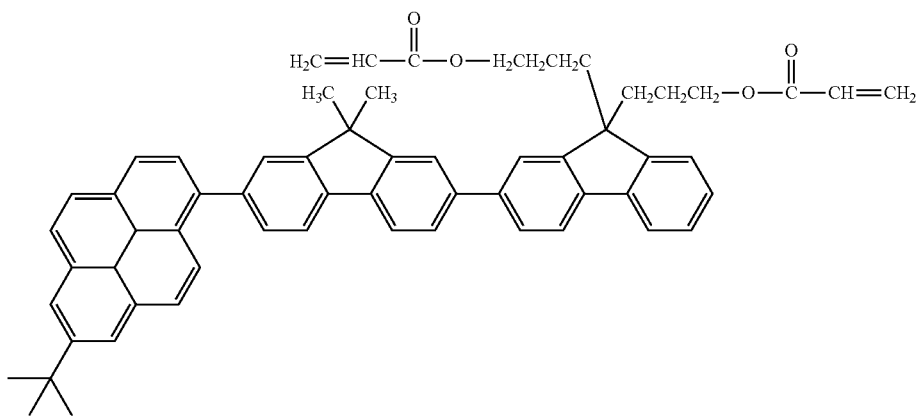
No. 90
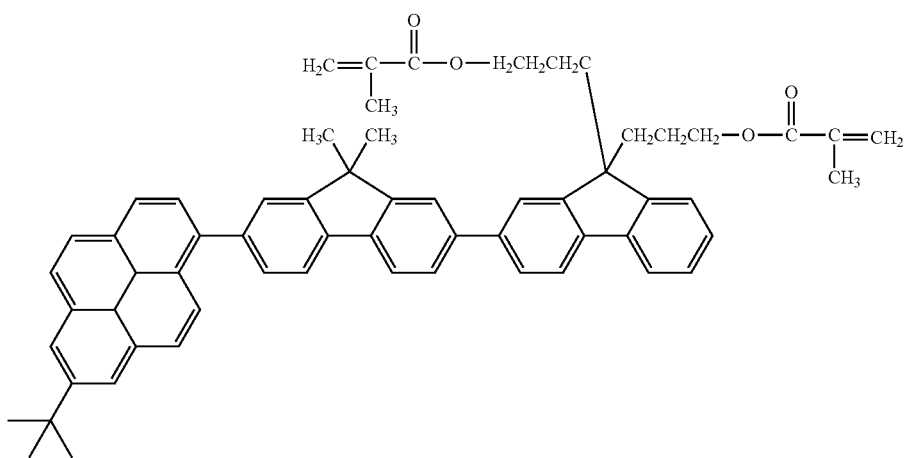
No. 91

-continued
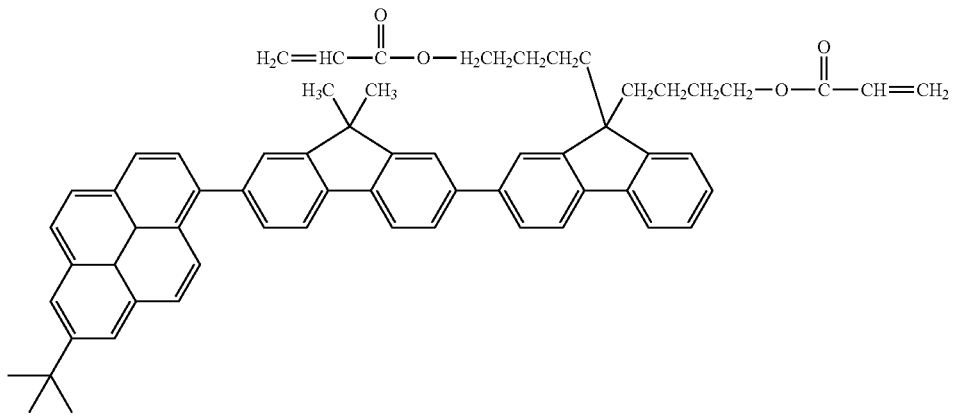
No. 92
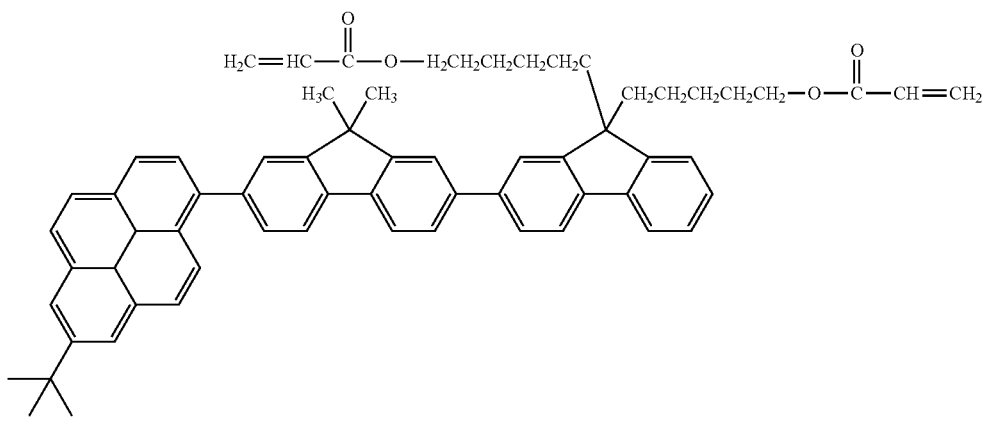
No. 93
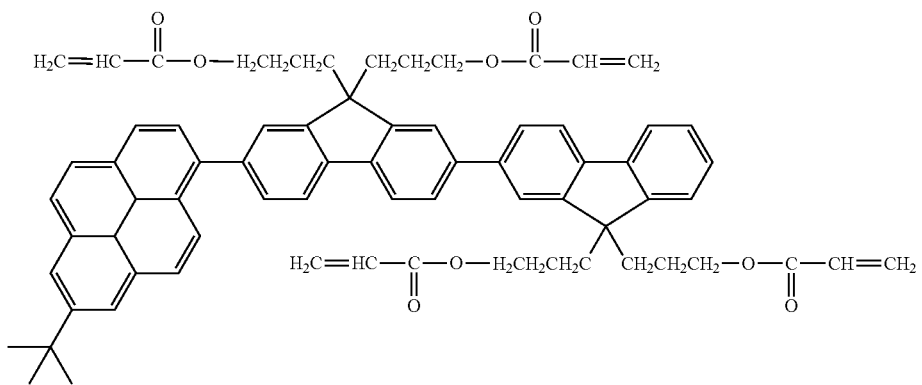
No. 94
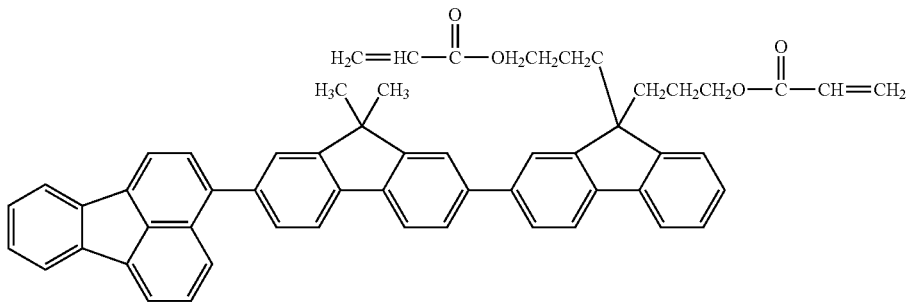
No. 95

No. 96
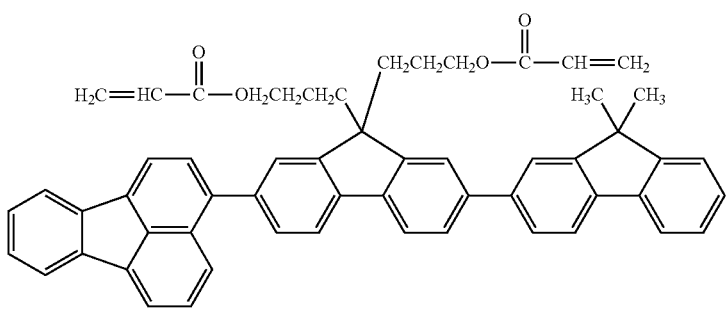
No. 97
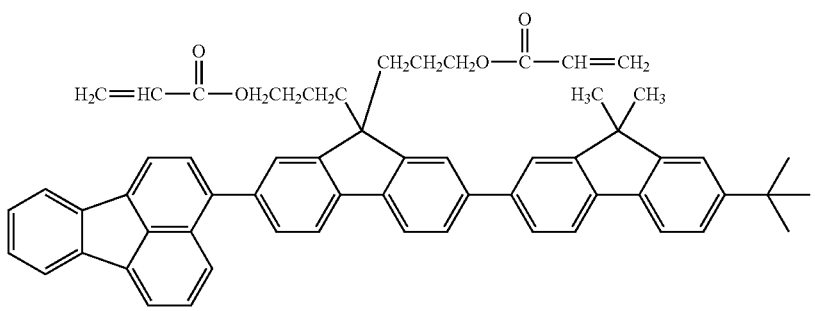
No. 98
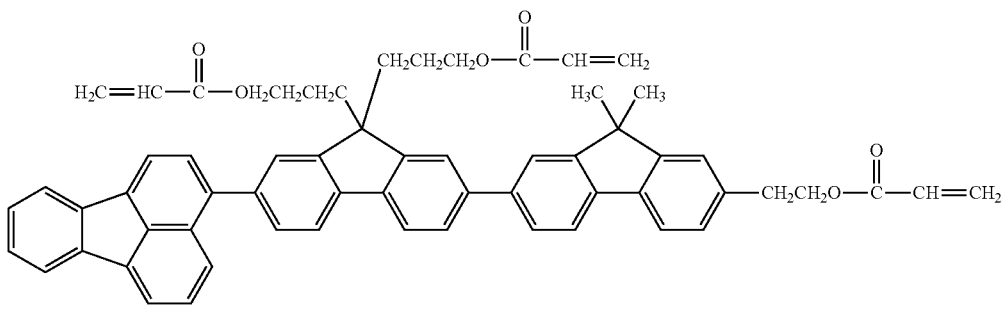
No. 99
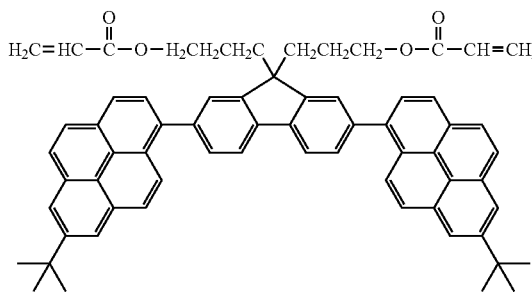
No. 100
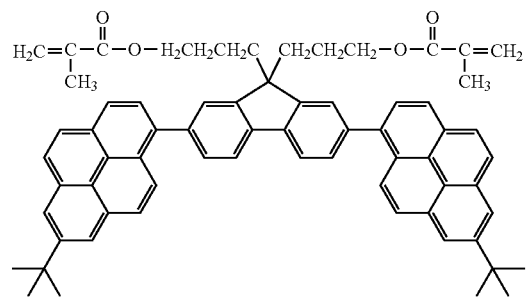
No. 101
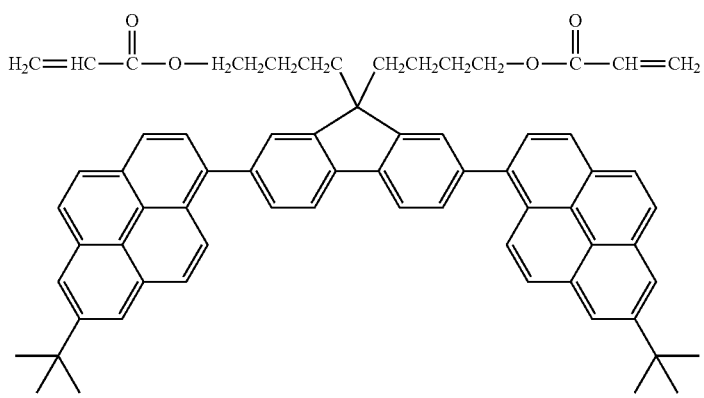

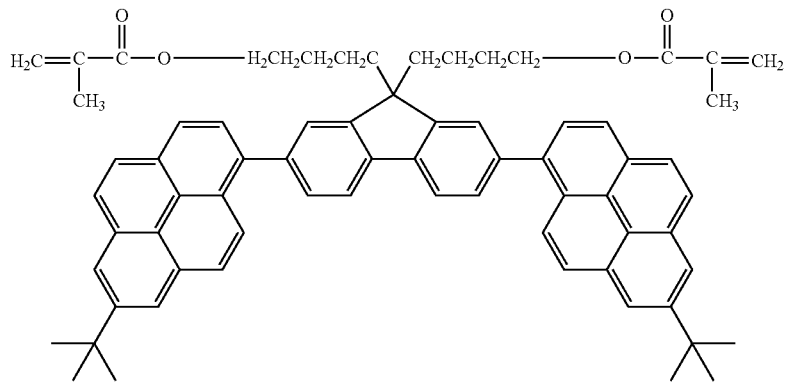
No. 102
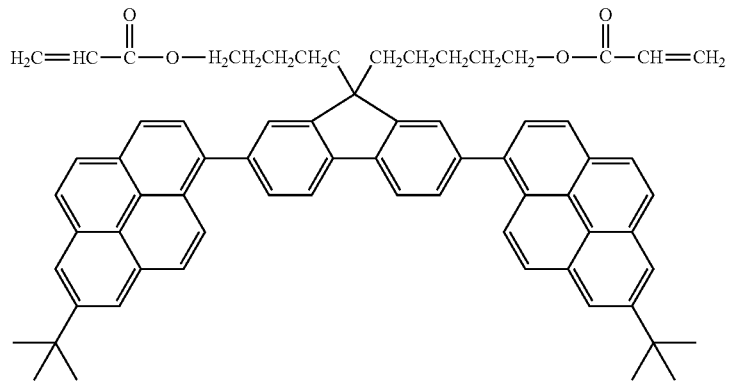
No. 103
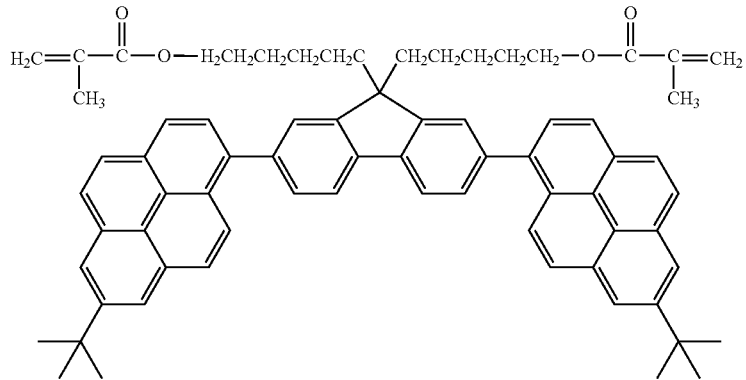
No. 104
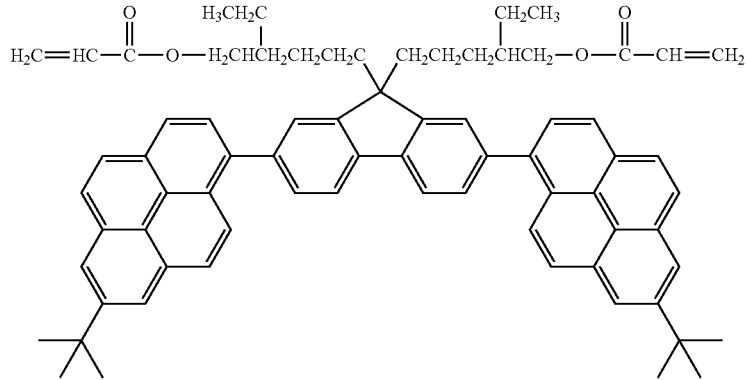
No. 105

-continued
No. 106
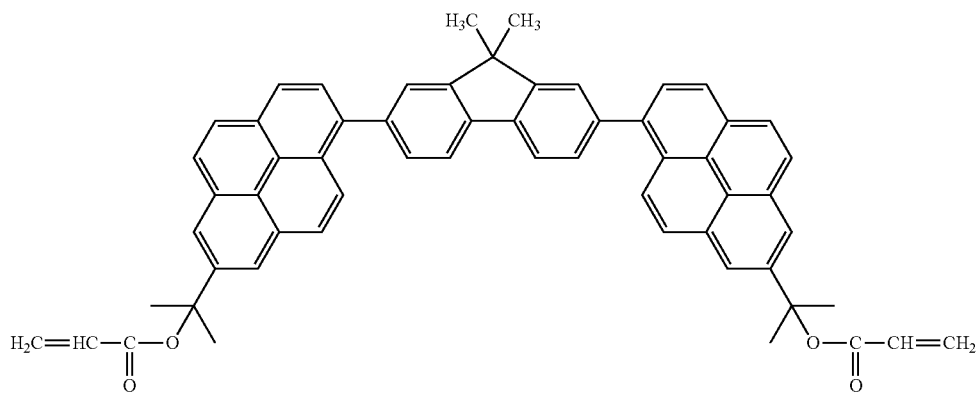
No. 107
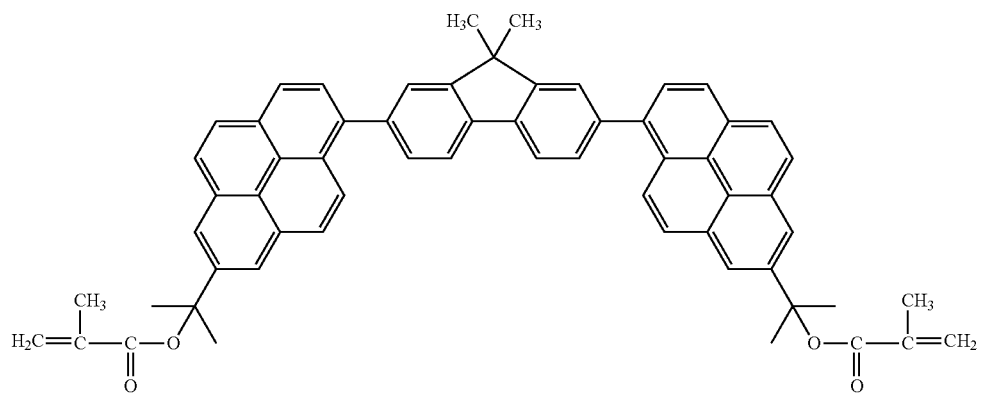
No. 108
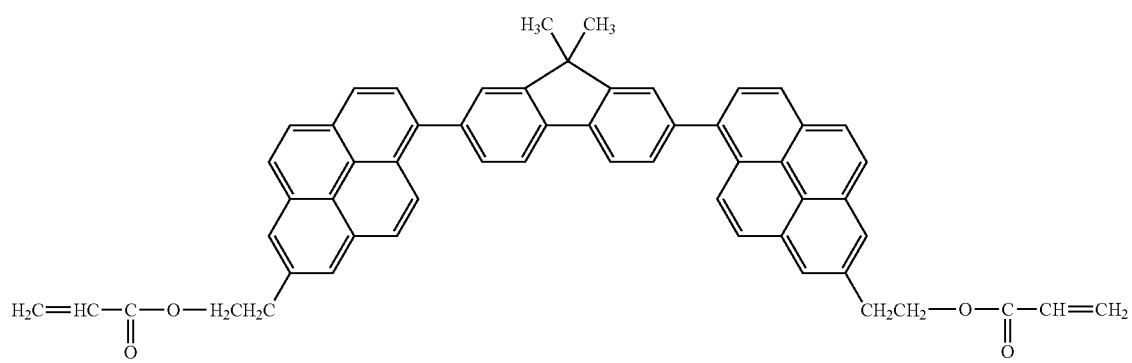
No. 109
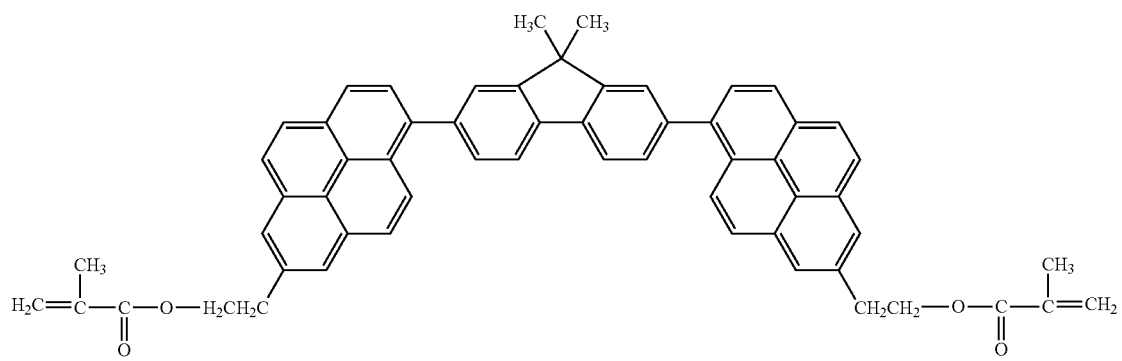

No. 110
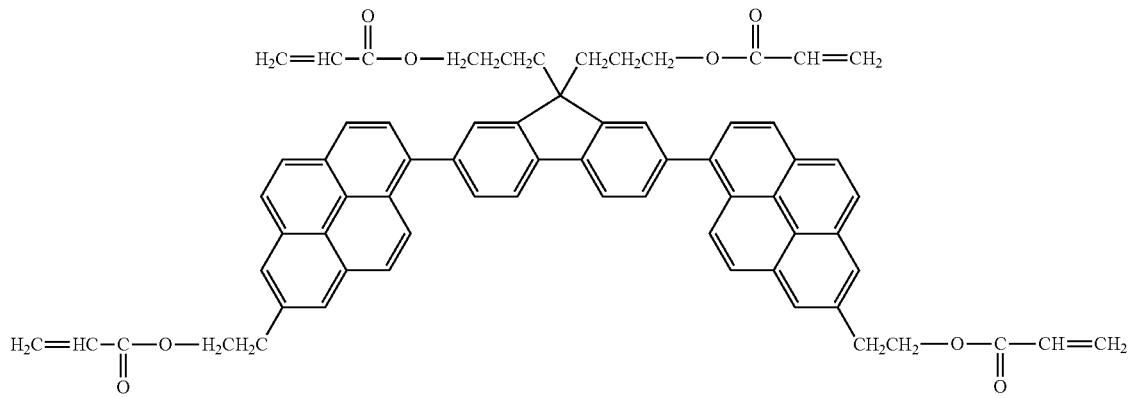
No. 111
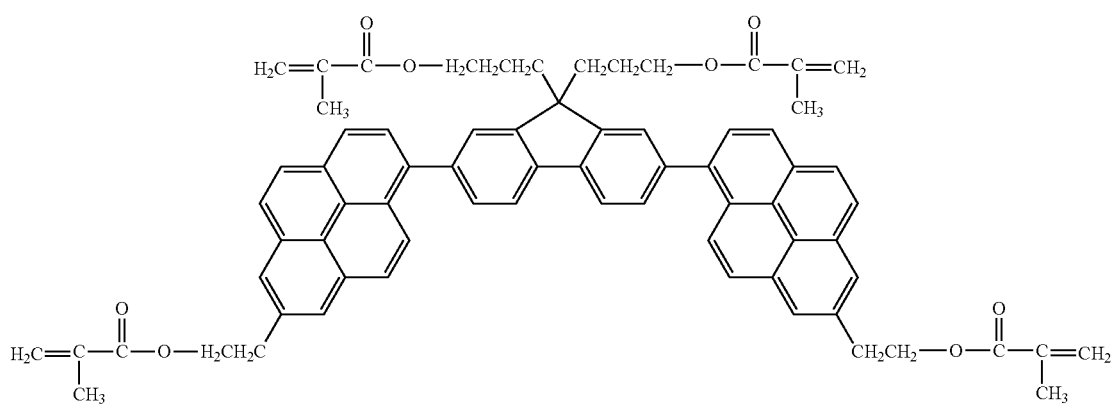
No. 112
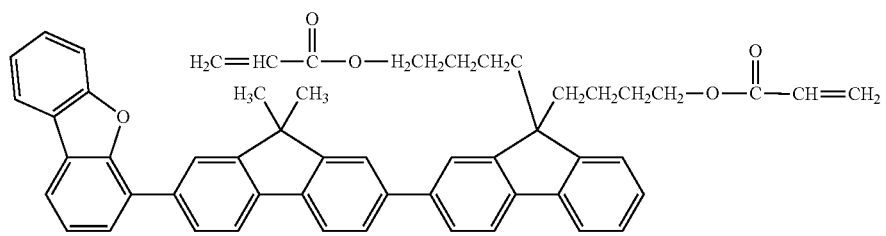
No. 113
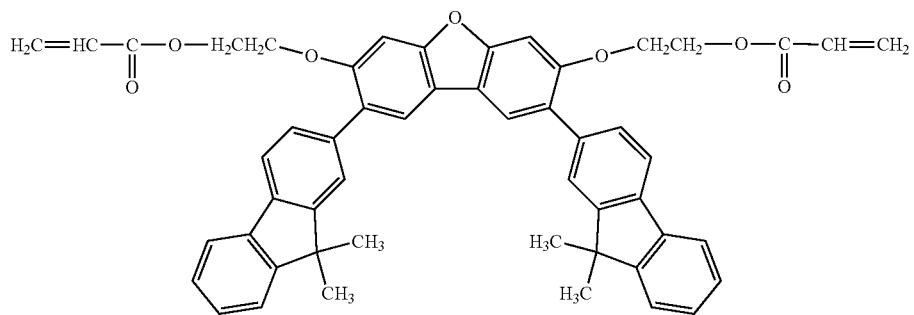

No. 114
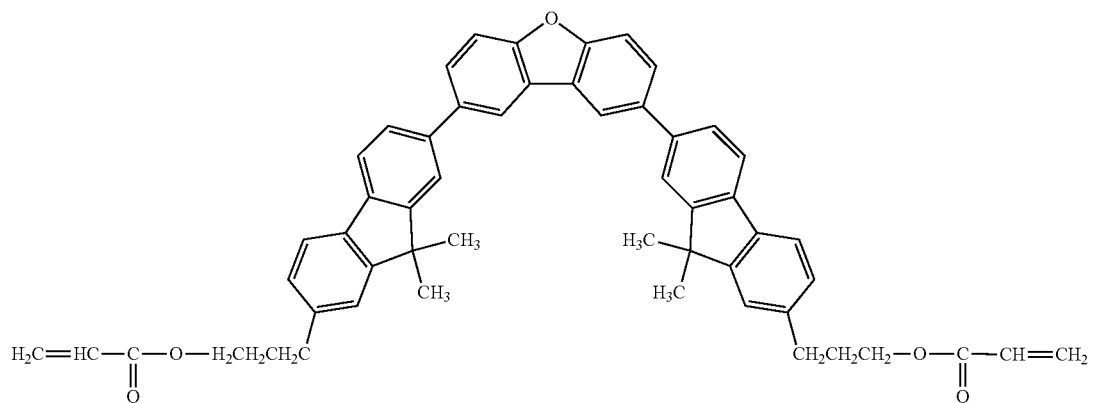
No. 115
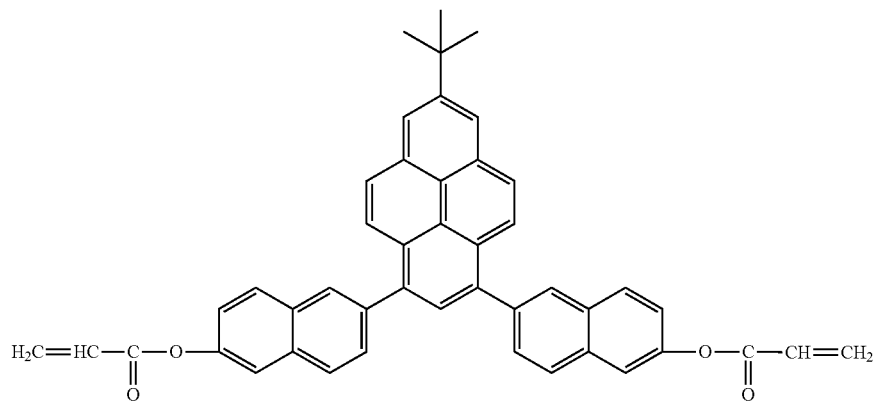
No. 116
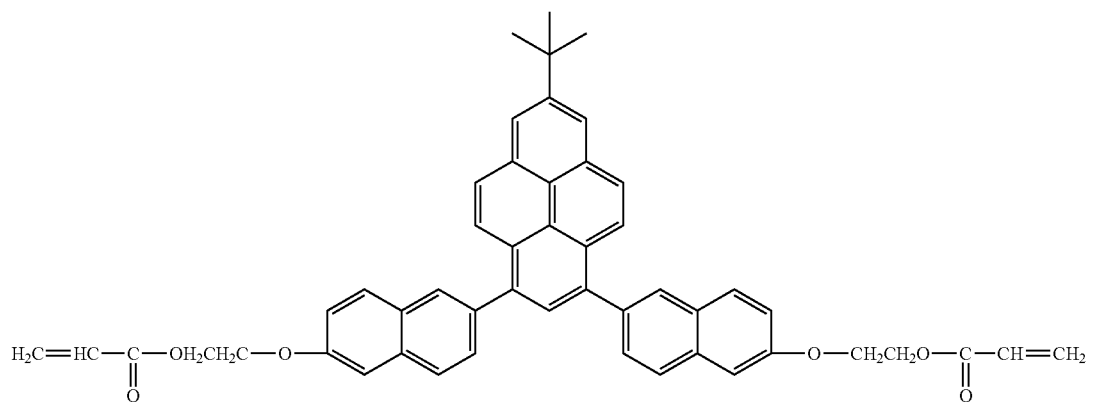

No. 117
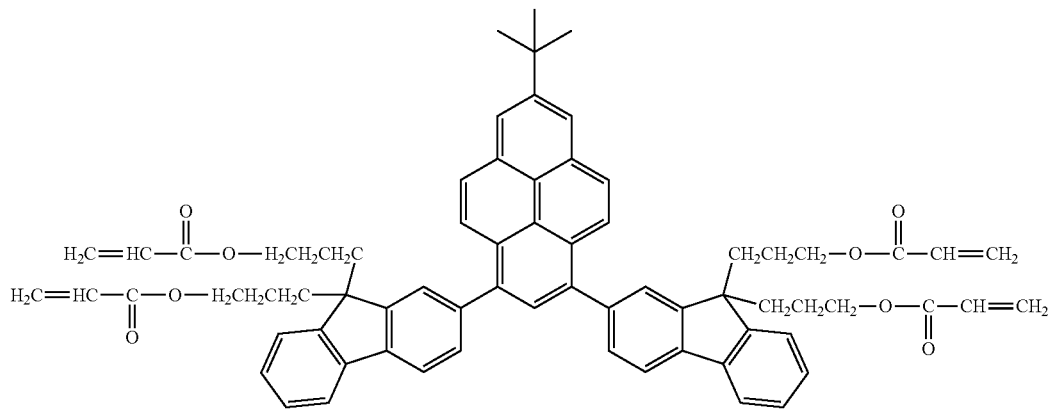
No. 118
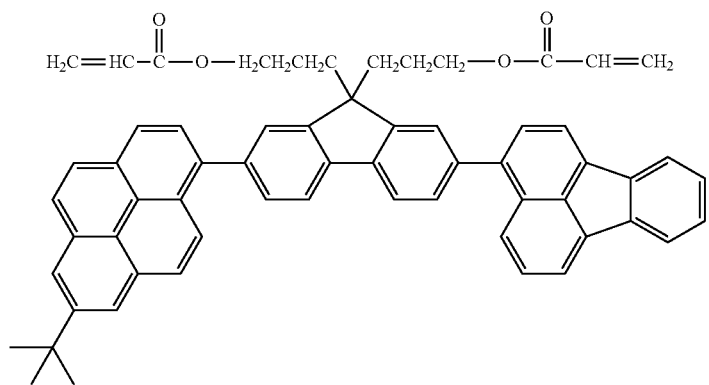
No. 119
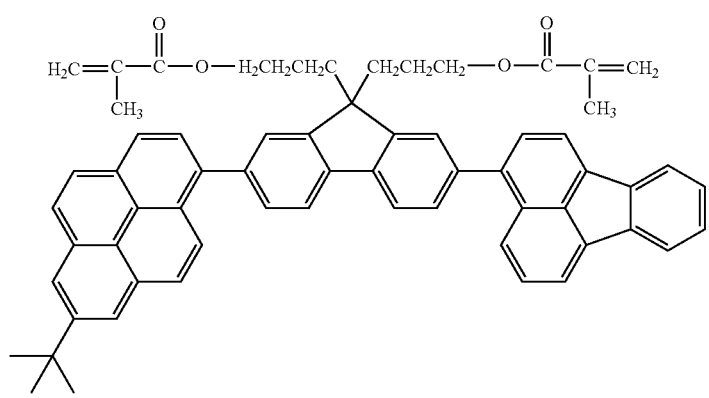
No. 120
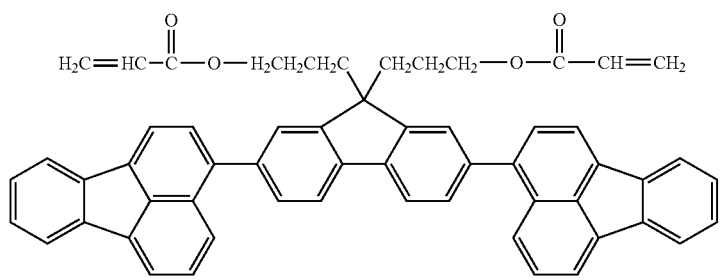

-continued
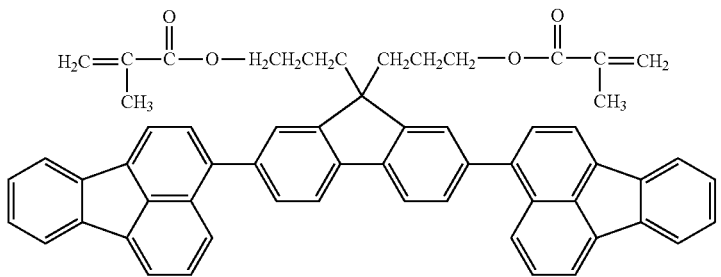
No. 121
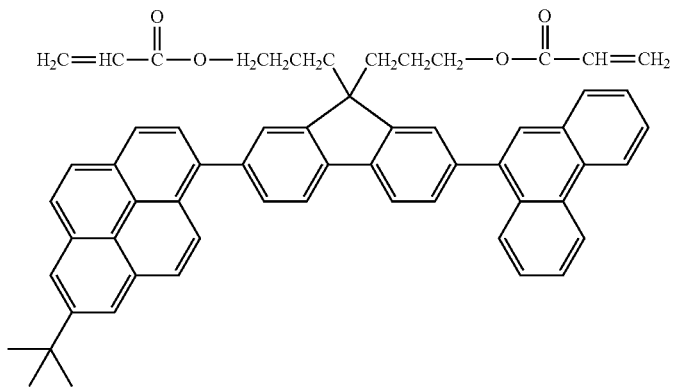
No. 122
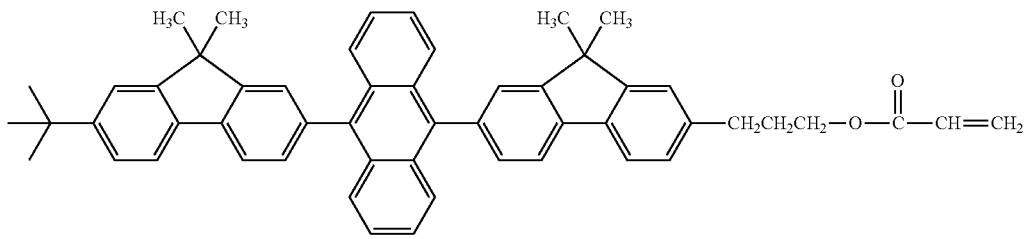
No. 123
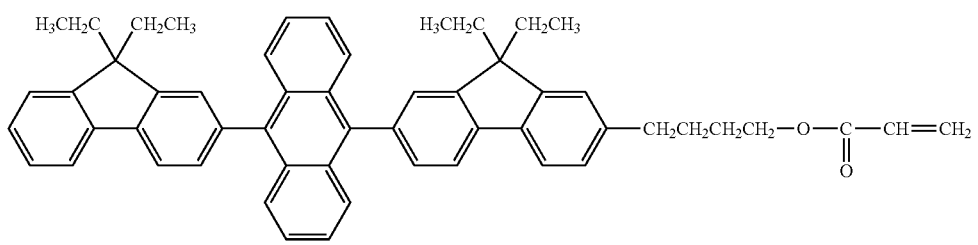
No. 124
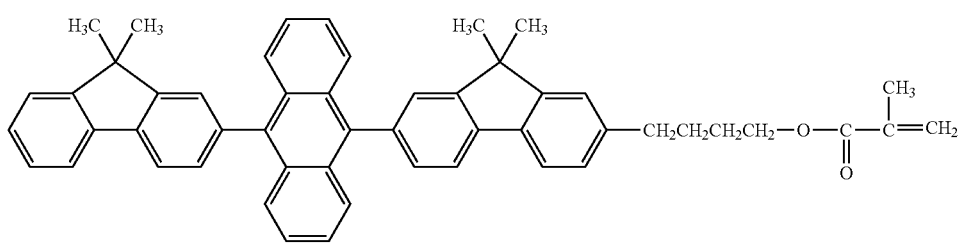
No. 125

No. 126
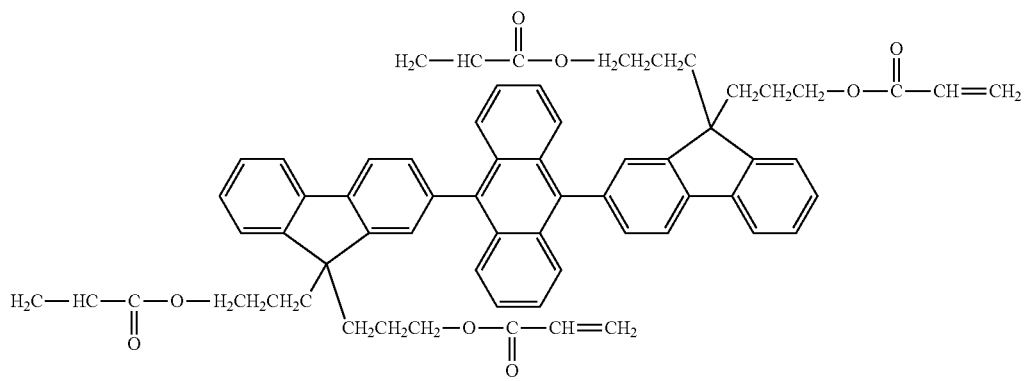
No. 127
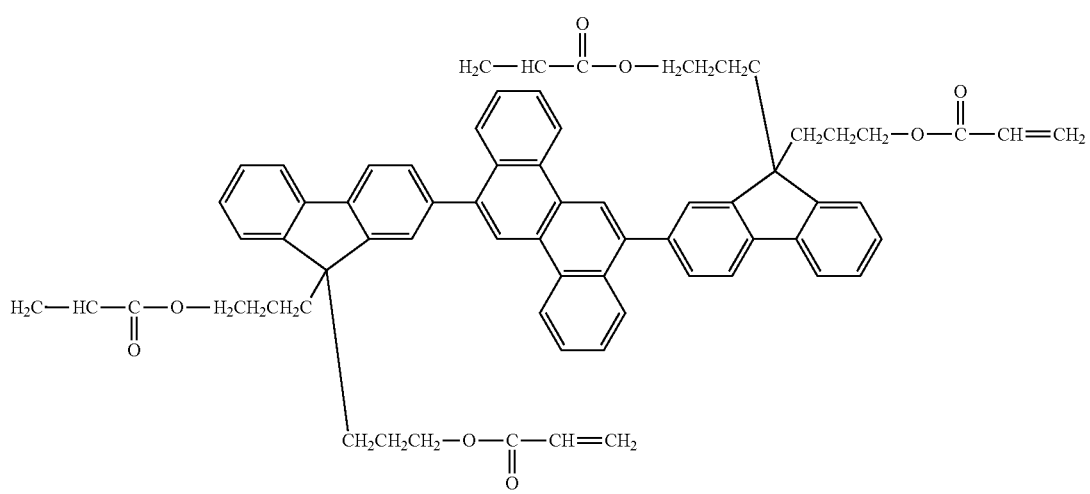
No. 128
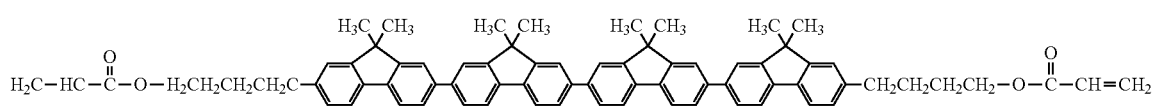
No. 129
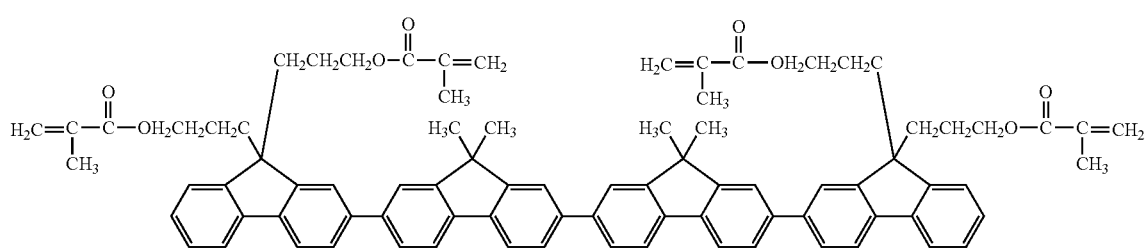
No. 130
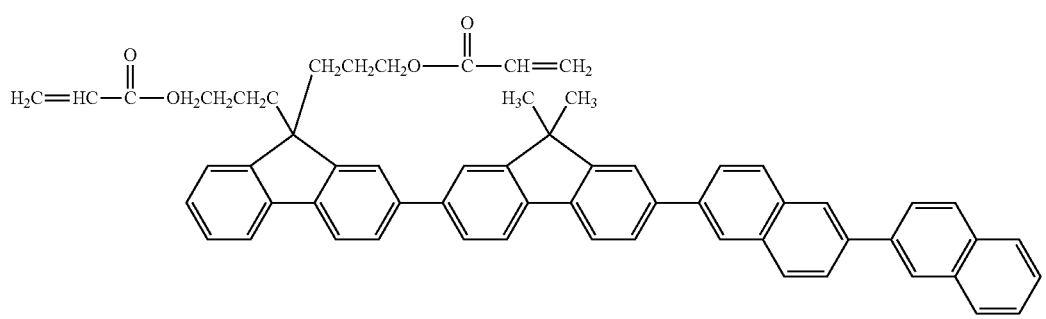

-continued
No. 131
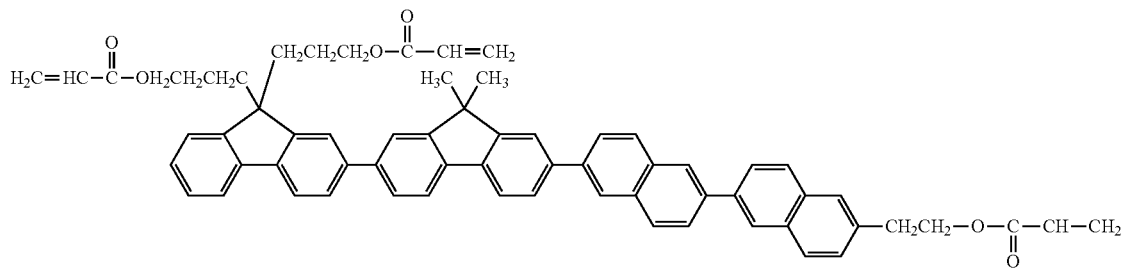
No. 132
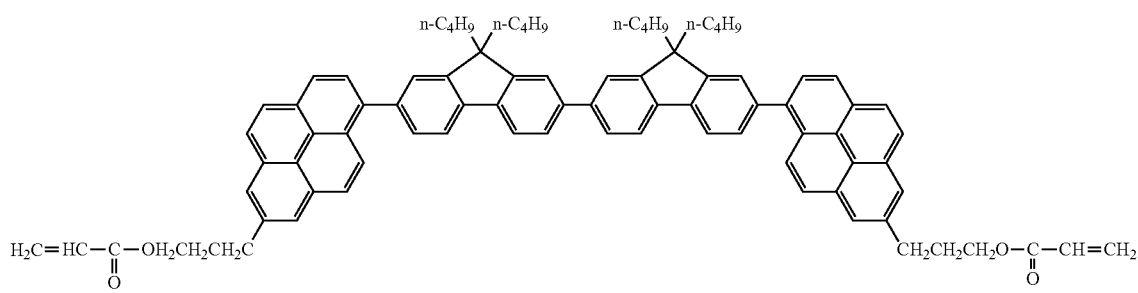
No. 133
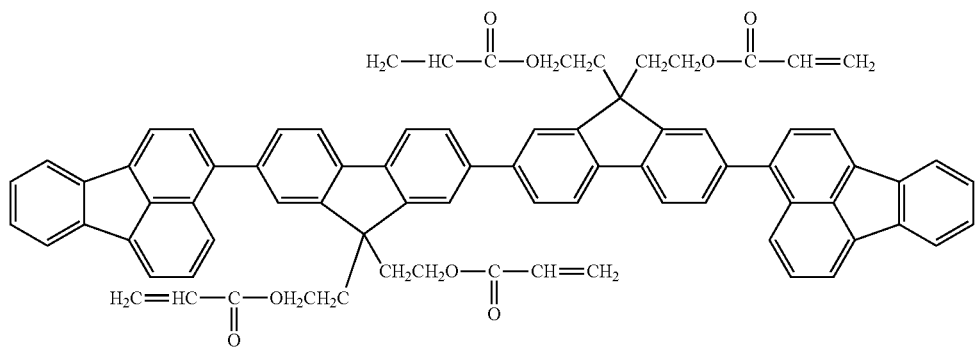
No. 134
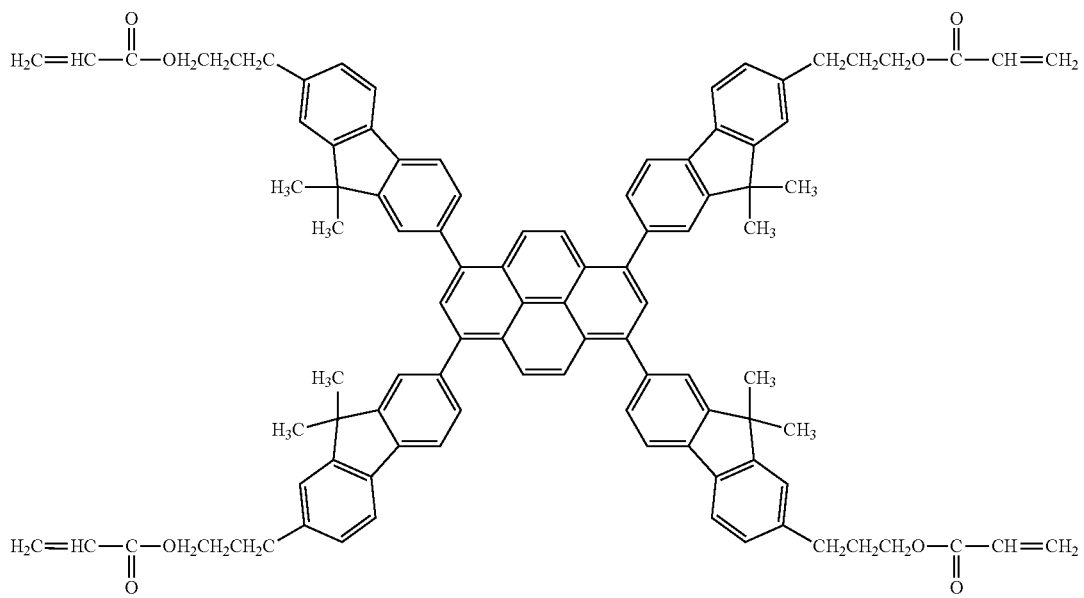

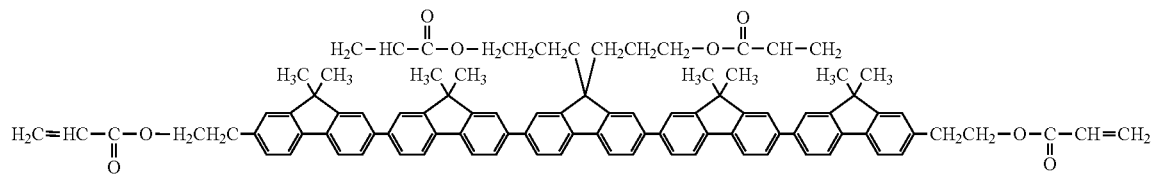
No. 135
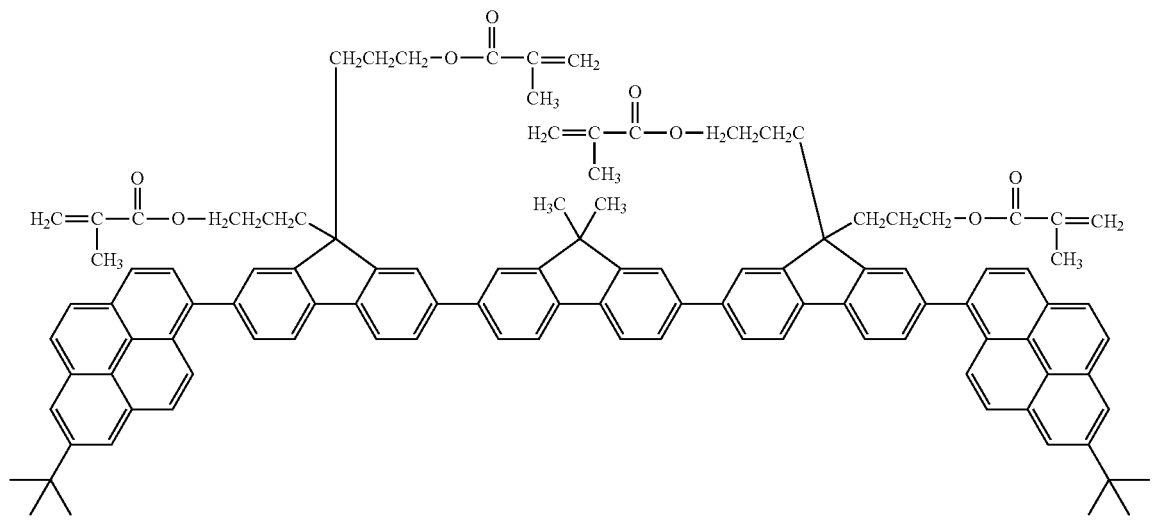
No. 136
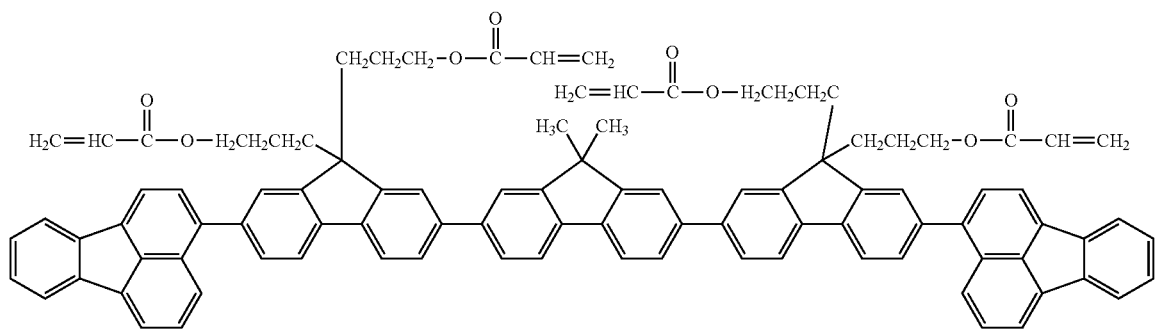
No. 137
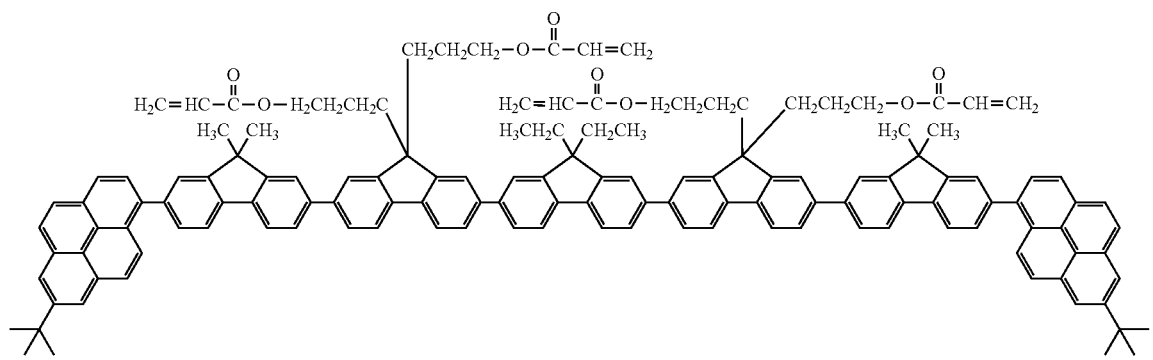
No. 138

-continued
No. 139
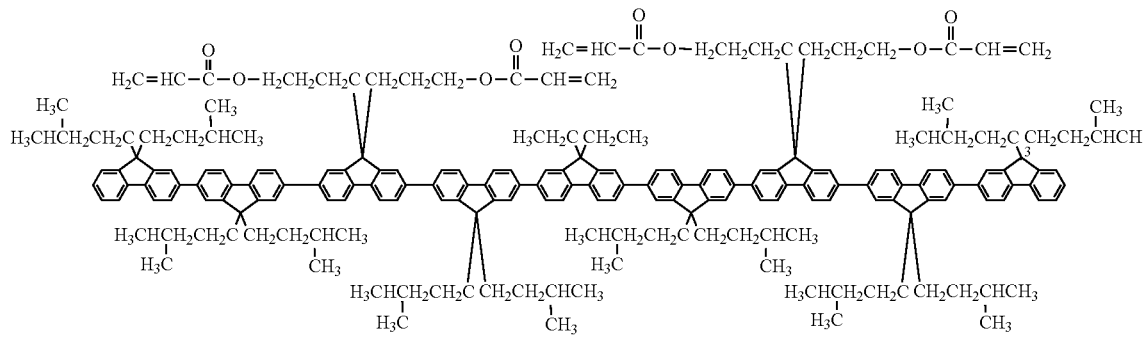
No. 140
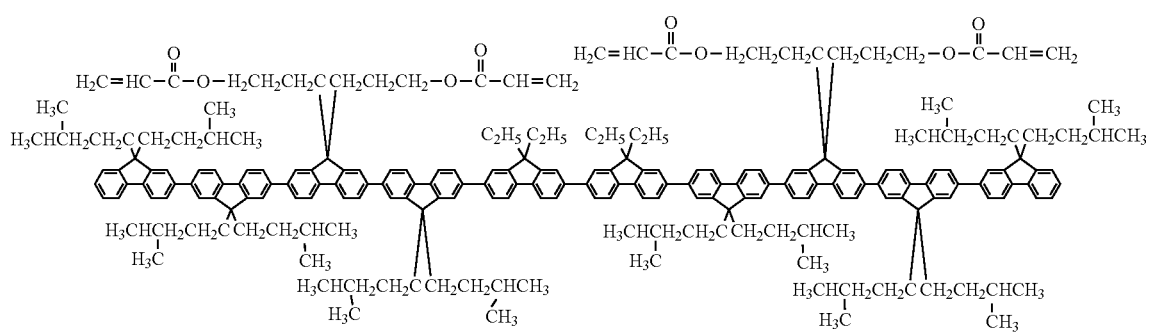
No. 141
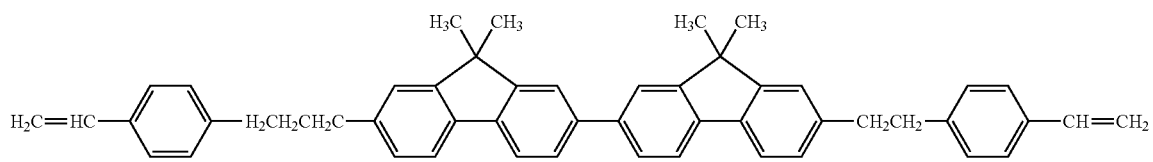
No. 142
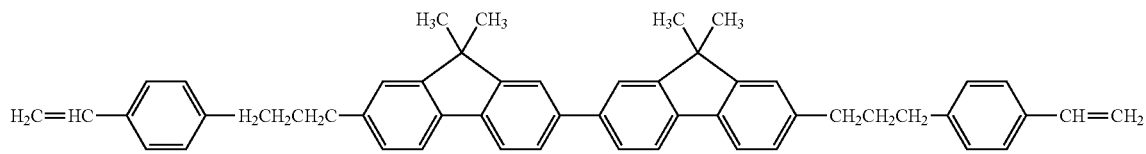
No. 143
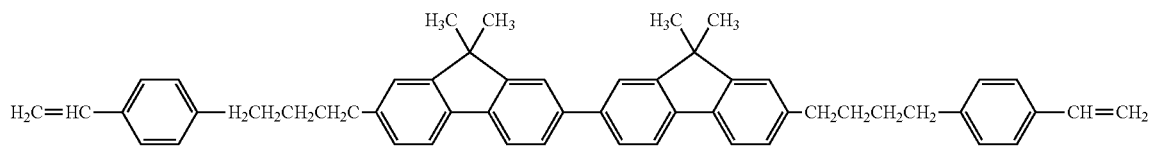
No. 144
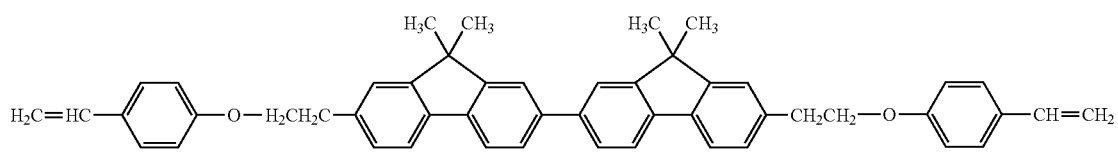

-continued
No. 145
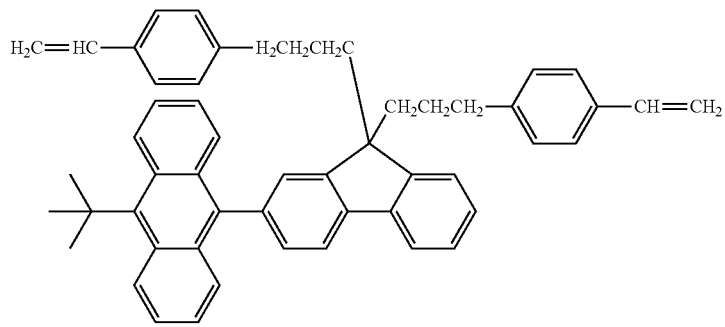
No. 146
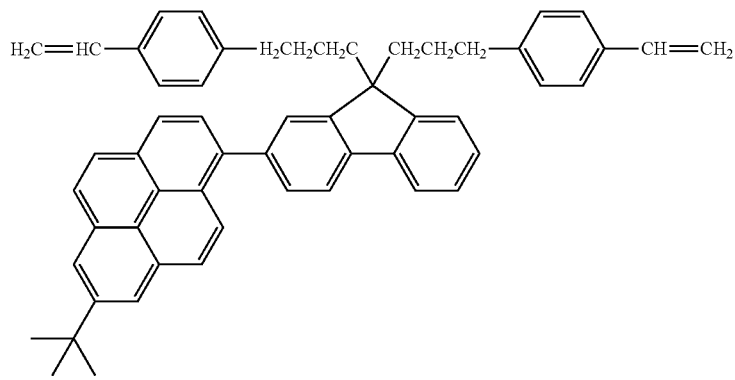
No. 147
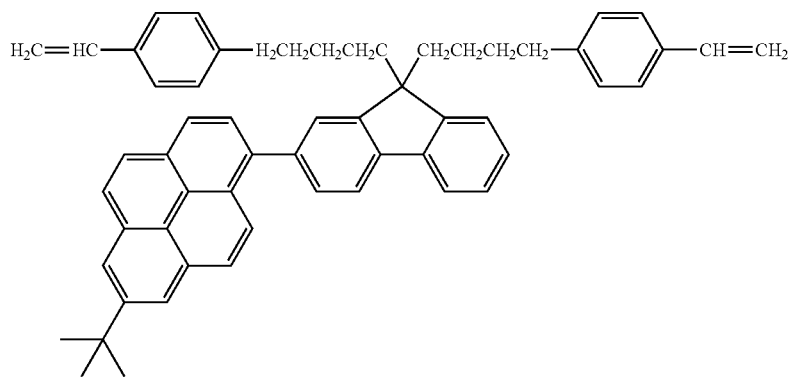
No. 148
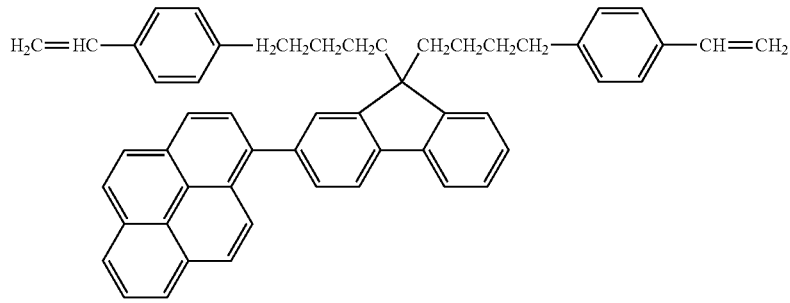
No. 149
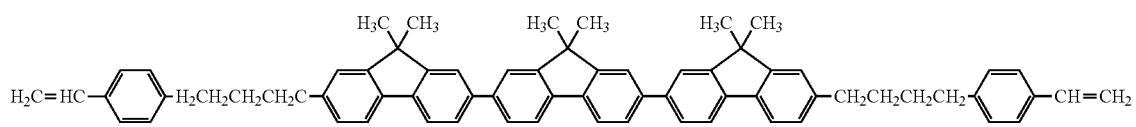

-continued
No. 150
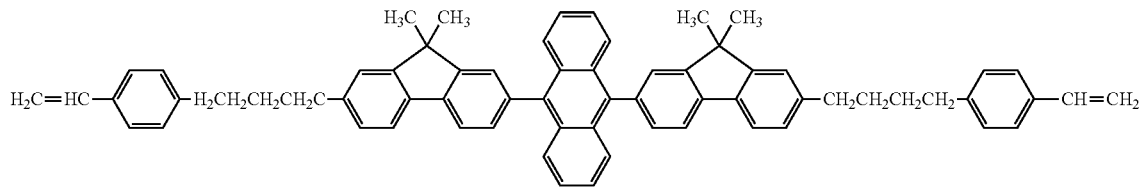
No. 151
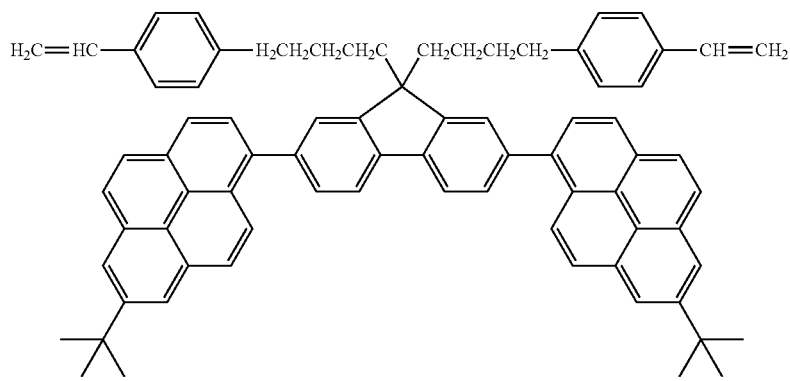
No. 152
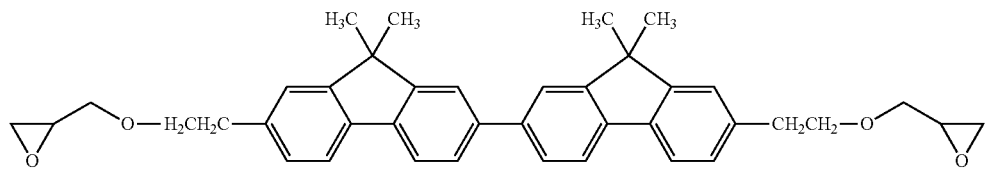
No. 153
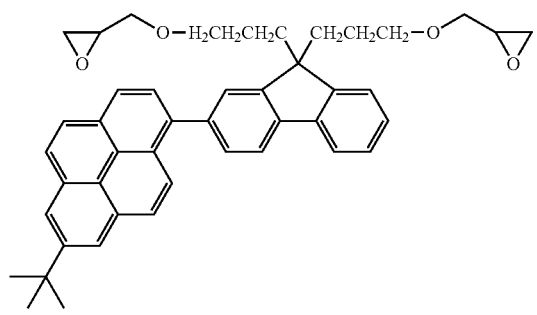
No. 154
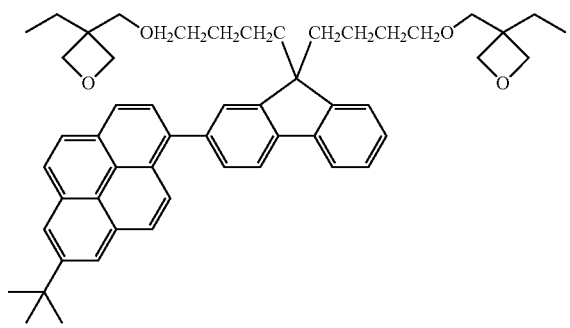
No. 155
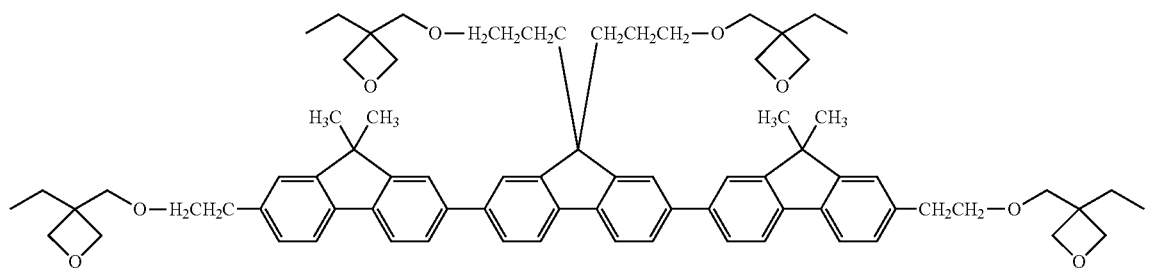

-continued
No. 156
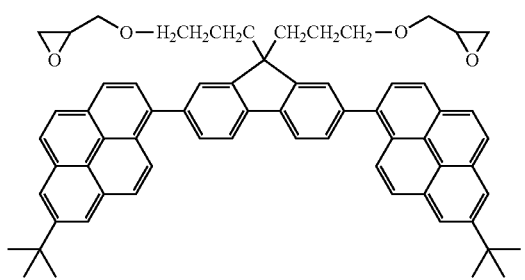
No. 157
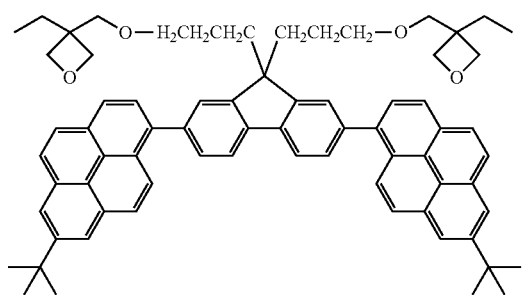
No. 158
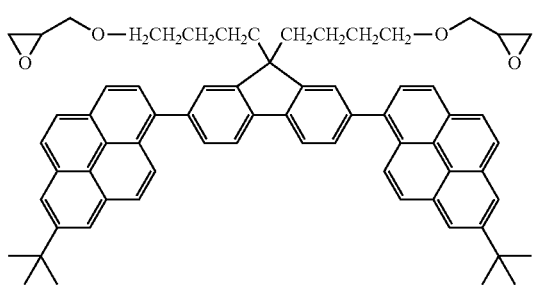
No. 159
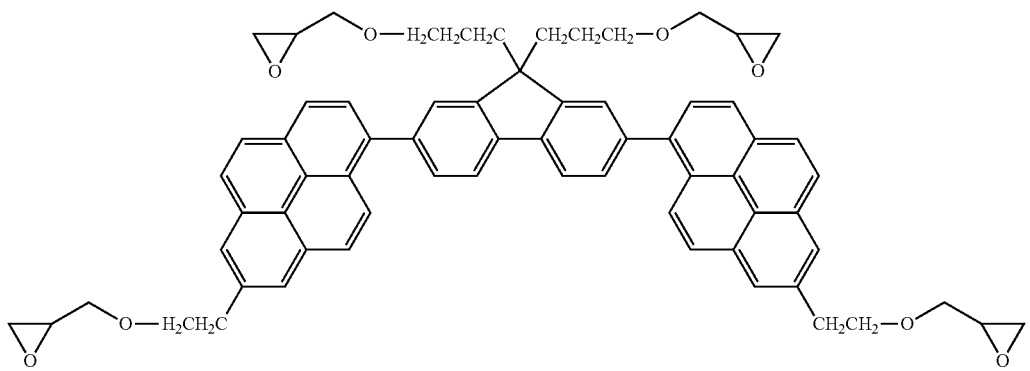
No. 160
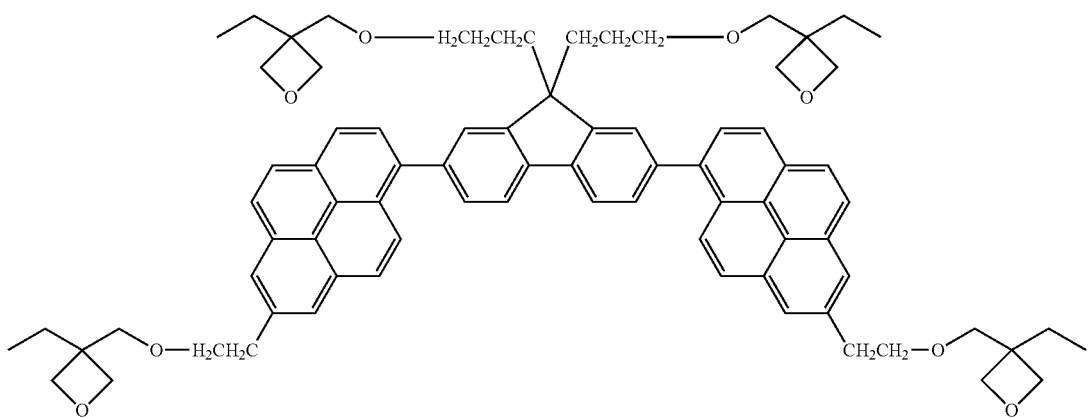

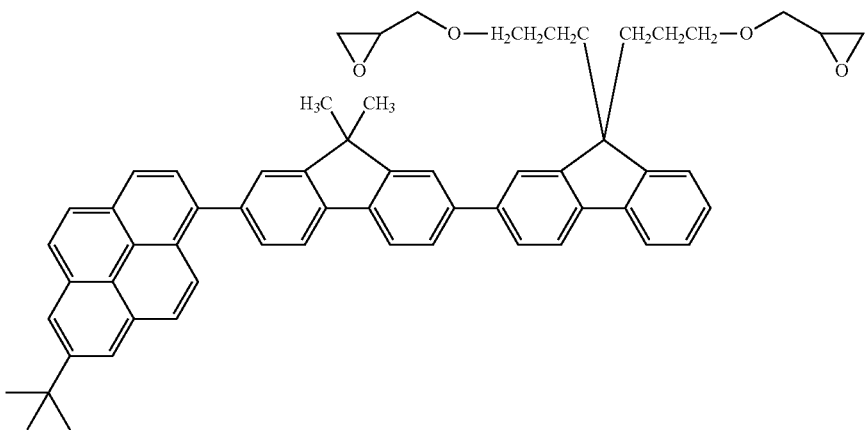
No. 161
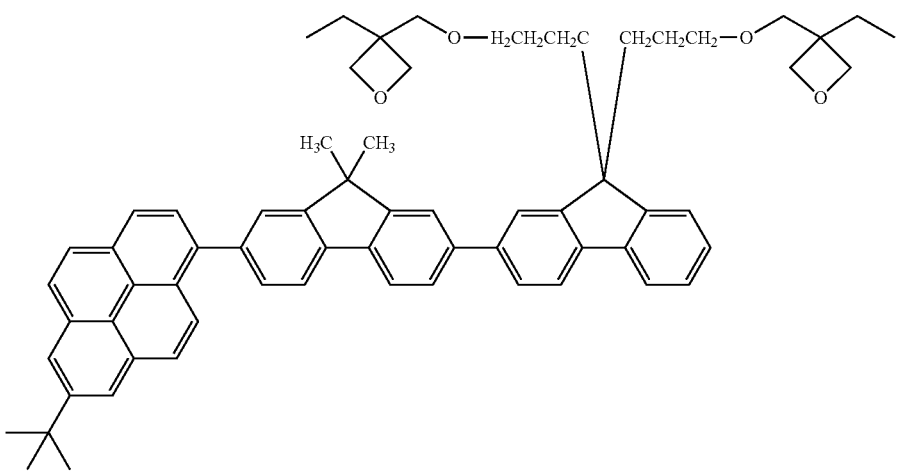
No. 162
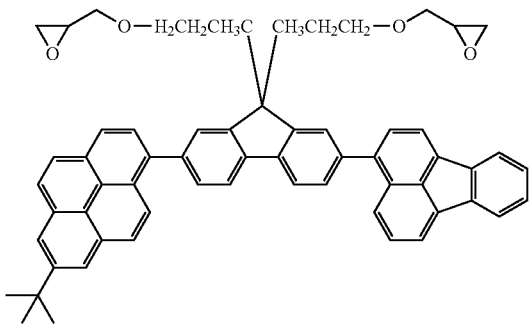
No. 163
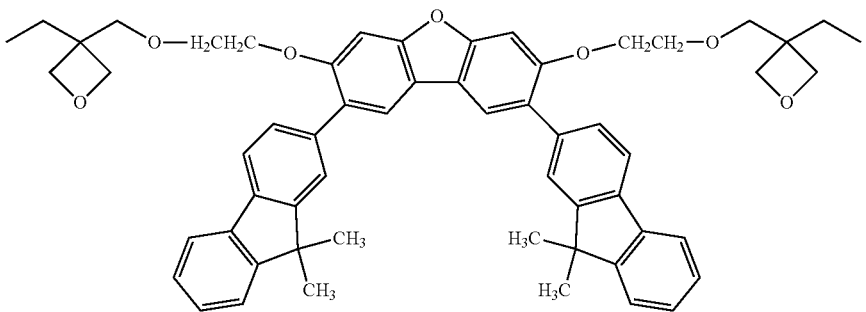
No. 164

-continued
No. 165
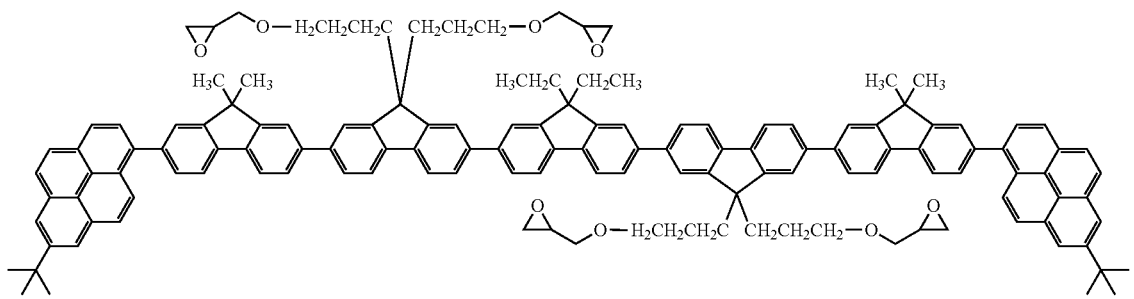
No. 166
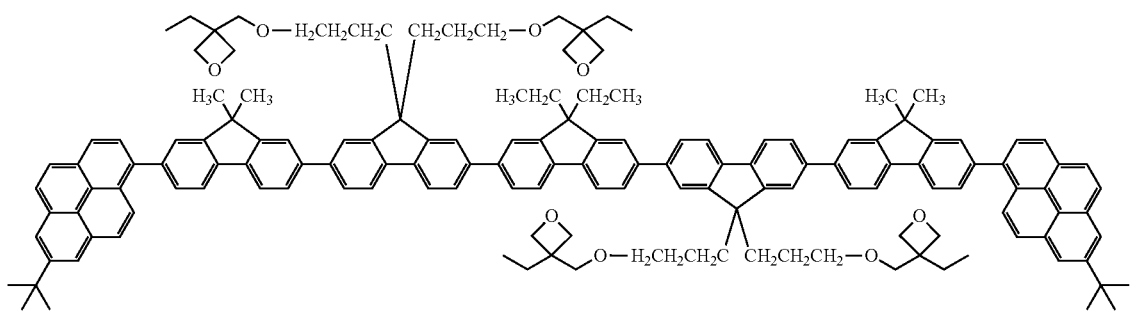
No. 167
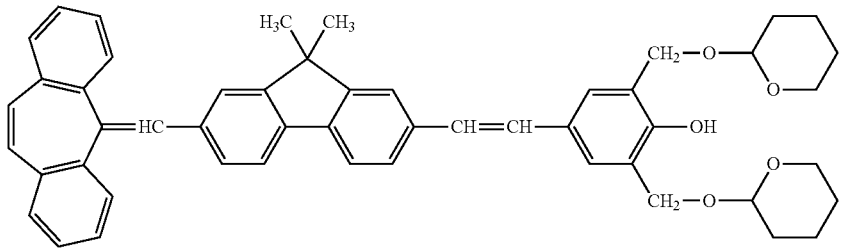
No. 168
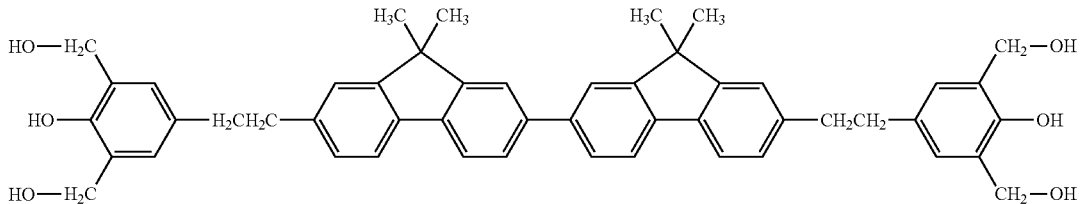
No. 169
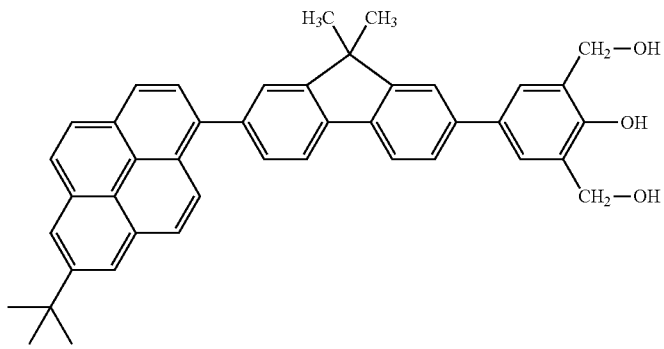

-continued
No. 170
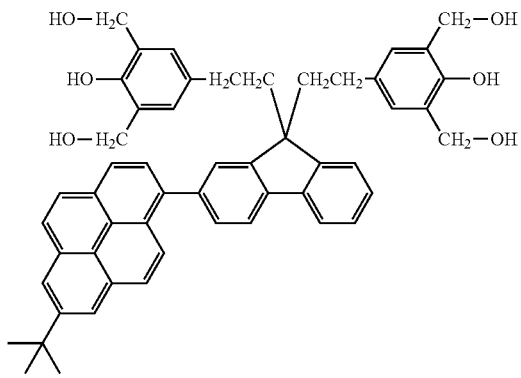
No. 171
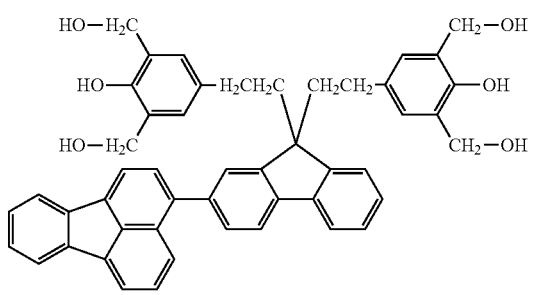
No. 172
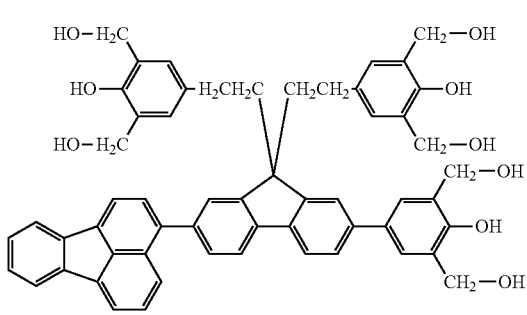
No. 173
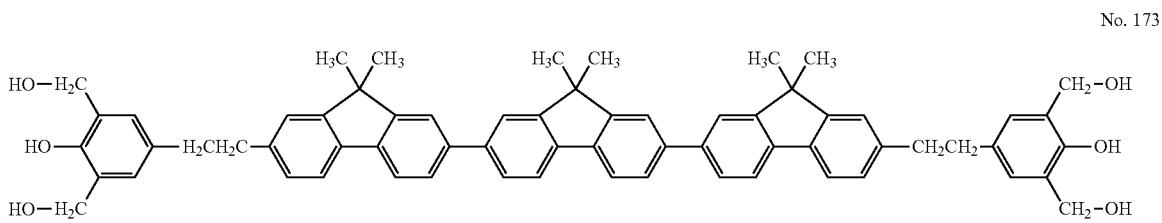
No. 174
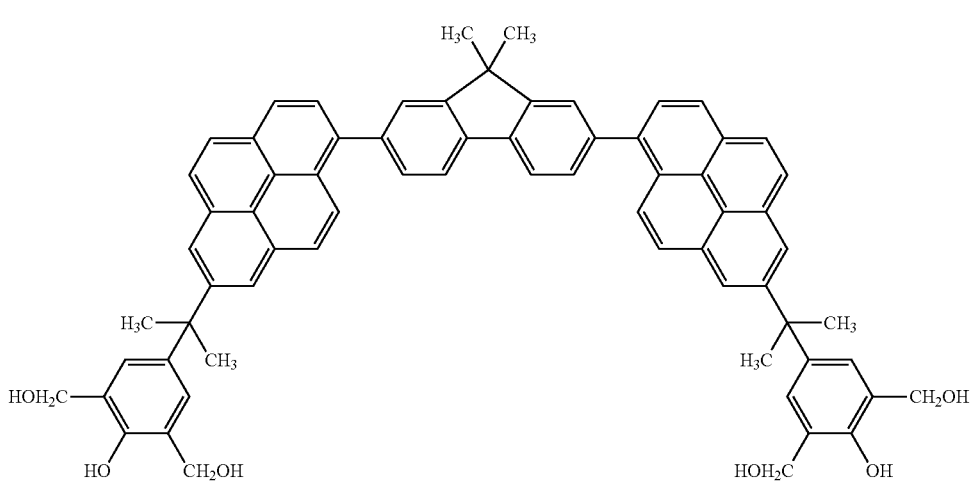

No. 175
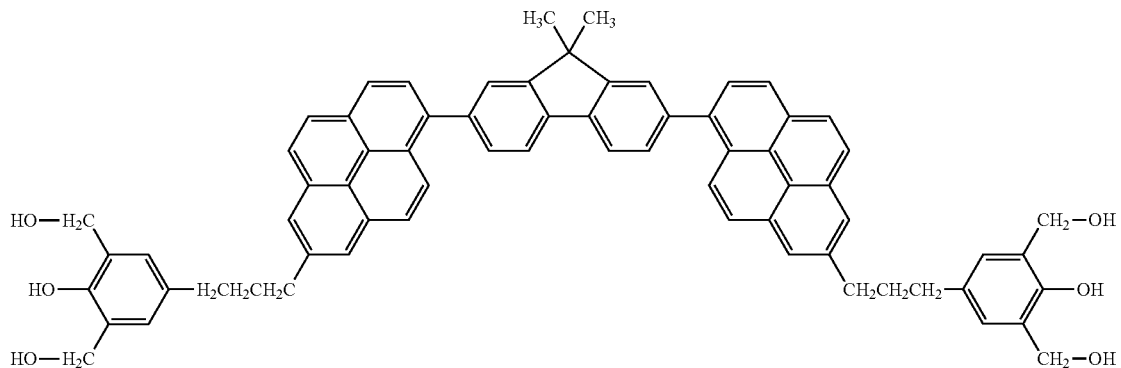
No. 176
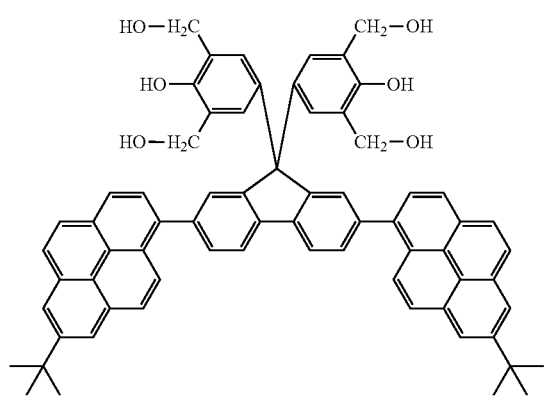
No. 177
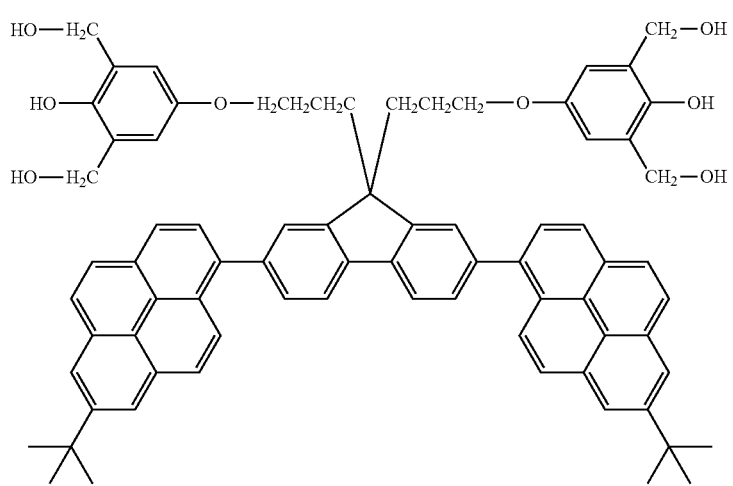

-continued
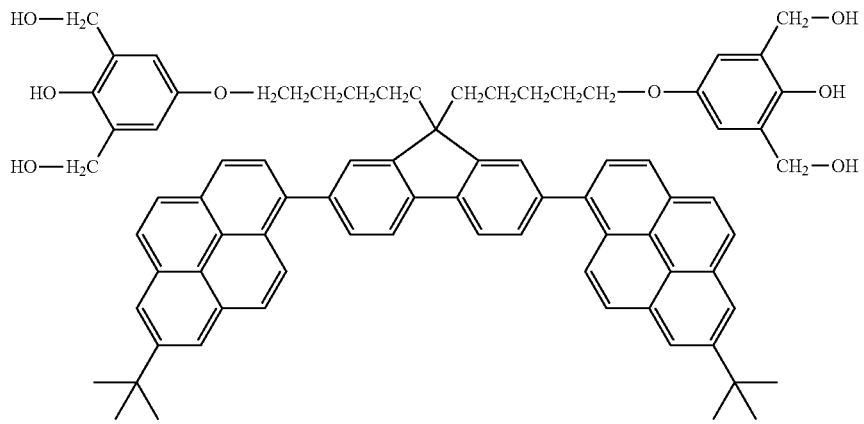
No. 178
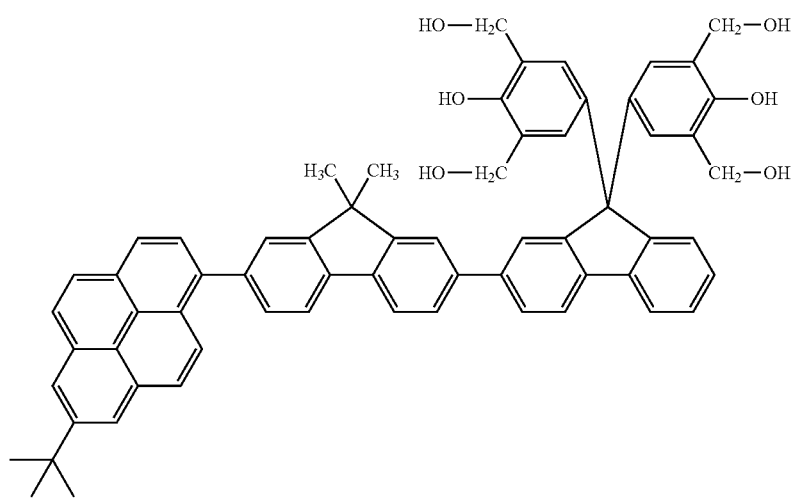
No. 179
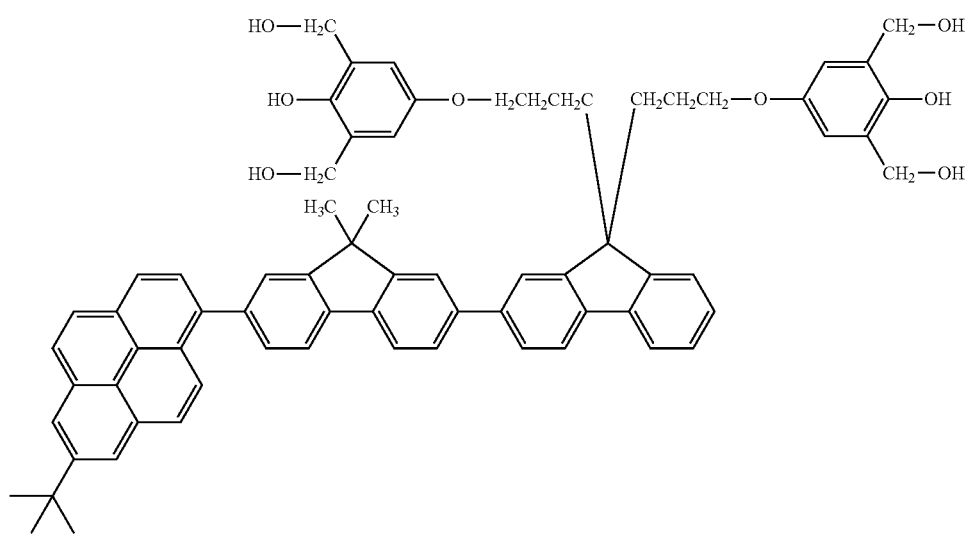
No. 180

-continued

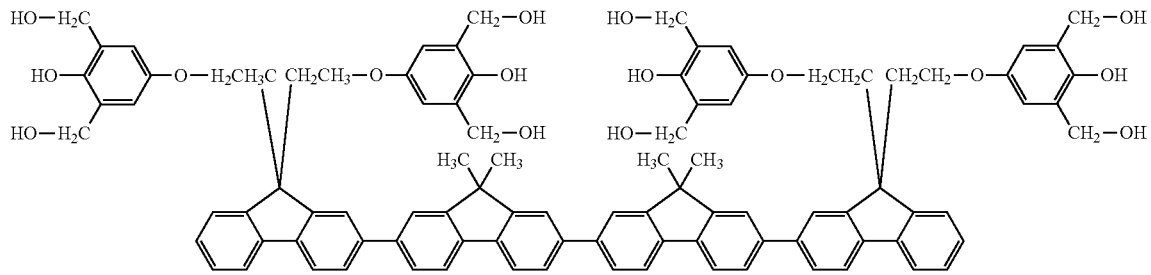
No. 181

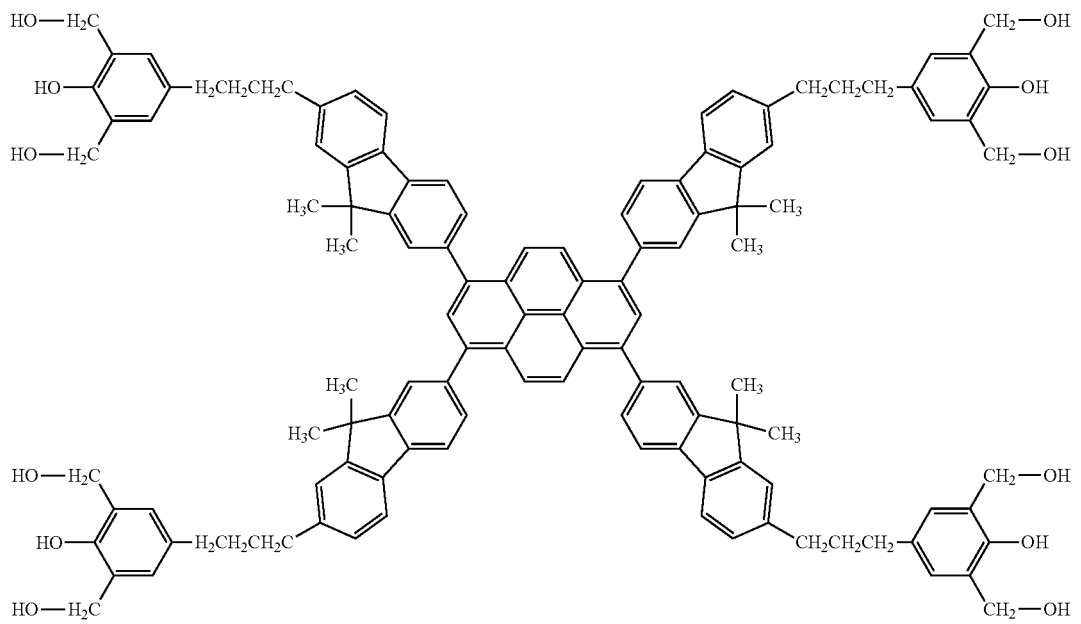
No. 182

A representative synthesis example of the hole transporting substance to be used in the present invention is described below.

Exemplified Compound No. 99 shown above was synthesized by a reaction represented by the following reaction formula (1). 8 Parts of a dihydroxy compound shown in the formula, 90 parts of tetrahydrofuran, and 3.6 parts of triethylamine were loaded into a three-necked flask, and the mixture wad dissolved, followed by the cooling of the mixture with ice water. Next, 2.7 parts of acryloyl chloride were slowly dropped under cooling at 5° C. or less while attention was paid to a temperature increase. After the completion of the dropping, the temperature of the reaction mixture was gradually increased until an internal temperature became 50° C., and the reaction was continued for 30 minutes.

After the completion of the reaction, 80 parts of a 10% aqueous solution of sodium hydroxide were added to the reaction mixture. 80 Parts of ethyl acetate were loaded into the mixture and an organic phase was separated, followed by the extraction of a product. The extraction operation was further performed with 80 parts of ethyl acetate twice. The resultant organic phase was subjected to a washing operation with 80 parts of pure water about three times. The washing was performed until the pH of an aqueous phase became about 7. The resultant organic phase was dehydrated with anhydrous magnesium sulfate and magnesium sulfate was removed by filtration. After that, the organic phase was concentrated to provide a crude product.

An impurity was removed from the resultant crude product by silica gel column chromatography. Further, the resultant was recrystallized with a mixed solvent of 20 parts of ethyl acetate and 20 parts of n-hexane, and was filtered and dried. Thus, the target diacrylated hole transporting substance was purified (yield=6.8 parts, percent yield=74.9%).

Reaction formula (1)

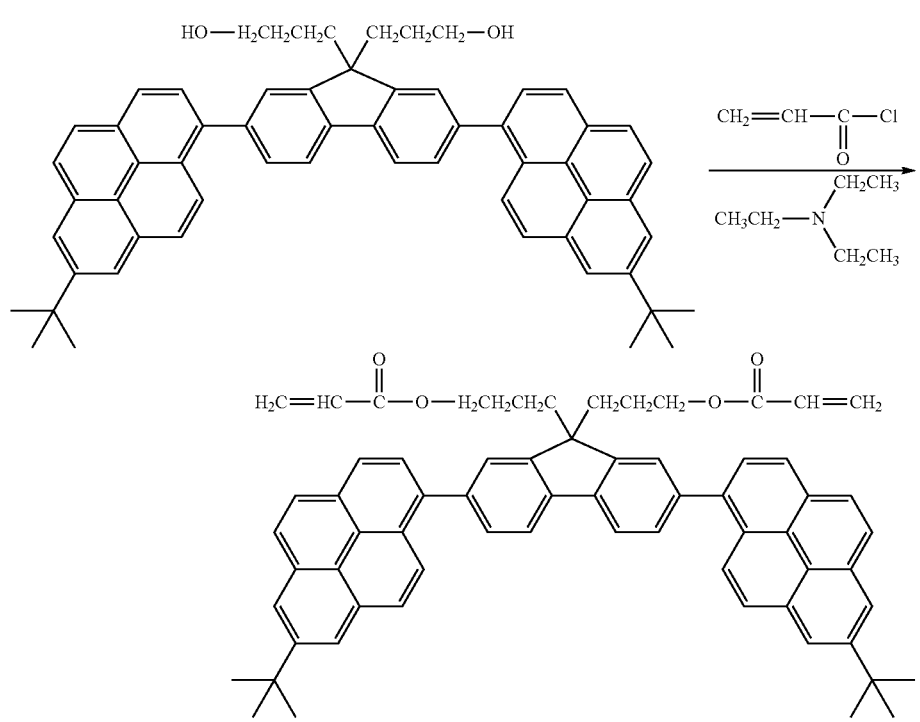

The surface layer of the present invention can contain a polymerized product of a composition containing: the hole transporting substance having a reactive functional group of the present invention; and a compound having a reactive functional group and free of a structure having hole transportability. The mechanical strength of the resultant polymerized product can be additionally improved. It is more preferred that: the hole transporting substance of the present invention has one or more reactive functional groups; and the compound free of a structure having hole transportability has two or more reactive functional groups.

The reactive functional group of the compound having a reactive functional group and free of a structure having hole transportability may be the above-mentioned reactive functional group. The reactive functional group is preferably a radically polymerizable functional group such as a styryl group, a vinyl group, an acryloyloxy group, or a methacryloyloxy group. The reactive functional group is more preferably the following radically polymerizable reactive group: an acryloyloxy group or a methacryloyloxy group.

The term "monofunctional" representing the number of functional groups described below means that a compound has one reactive functional group.

Examples of the compound having a reactive functional group and free of a structure having hole transportability include the following compounds. The examples described below each have an acryloyloxy group as a reactive functional group.

As a monofunctional polymerizable monomer, there are given, for example, ethyl acrylate, n-propyl acrylate, n-butyl acrylate, isobutyl acrylate, 2-ethylhexyl acrylate, 2-hydroxyethyl acrylate, tetrahydrofurfuryl acrylate, benzyl acrylate, cyclohexyl acrylate, ethoxy-diethylene glycol acrylate, isoamyl acrylate, lauryl acrylate, stearyl acrylate, phenoxyethyl acrylate, phenoxydiethyleneglycol acrylate, and ethoxylated o-phenylphenol acrylate.

As a difunctional polymerizable monomer, there are given, for example, 1,4-butanediol acrylate, 1,5-pentanediol diacrylate, 3-methyl-1,5-pentanediol diacrylate, 1,6-hexanediol acrylate, 1,9-nonanediol diacrylate, 1,10-decanediol diacrylate, triethylene glycol diacrylate, neopentyl glycol diacrylate, and tricyclodecanedimethanol diacrylate.

As a trifunctional polymerizable monomer, there are given, for example, trimethylolpropane triacrylate, pentaerythritol triacrylate, and ethoxylated isocyanuric acid triacrylate.

As a tetrafunctional polymerizable monomer, there are given, for example, pentaerythritol tetraacrylate and dimethylolpropane tetraacrylate.

As a hexafunctional polymerizable monomer, there is given, for example, dipentaerythritol hexaacrylate.

Although acrylate monomers are exemplified as described above, a compound having a reactive functional group synthesized by substituting an acryloyloxy group with a methacryloyloxy group or any other reactive functional group may be used as required.

The molecular weight of the compound having a reactive functional group and free of a structure having hole transportability is preferably 100 or more and 1,000 or less.

Inorganic fine particles whose surfaces are treated with a compound having a chain polymerizable functional group may be incorporated into the surface layer from the viewpoint of the wear resistance. A silane compound having not only the chain polymerizable functional group but also a halogen atom, an alkoxy group, an acyloxy group, an aminooxy group, or the like in a molecule is used as the compound having the chain polymerizable functional group. Silyl group reacts with the inorganic fine particle, and the chain polymerizable functional group undergoes a polymerization reaction with the hole transporting substance of the present invention to be strongly stuck into the surface layer, whereby the wear resistance can be improved. Of such groups, an alkoxysilane group is preferred.

Examples of the chain polymerizable functional group include: radically polymerizable functional groups such as a vinyl group, an acryloyl group, and a methacryloyl group; and cationically polymerizable functional groups such as an epoxy group and an oxetane group. Of the chain polymerizable functional groups, an acryloyl group or a methacryloyl group is preferred. Examples of a compound preferred as the compound having the chain polymerizable functional group are shown below. One kind of these silane compounds may be used, or two or more kinds thereof may be used as a mixture.

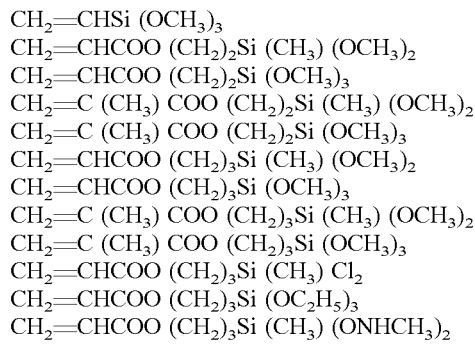

As the inorganic fine particles, there may be used particles including at least one kind selected from the group consisting of alumina, silica, tin oxide and titanium oxide.

The surface layer can be formed by: forming a coat of a surface-layer coating solution containing the hole transporting substance of the present invention; and drying and/or curing the coat.

As a solvent to be used for the surface-layer coating solution, there may be used, for example, an alcohol-based solvent, a sulfoxide-based solvent, a ketone-based solvent, an ether-based solvent, an ester-based solvent, an aliphatic halogenated hydrocarbon-based solvent, or an aromatic hydrocarbon-based solvent.

When the surface layer is a protective layer, the thickness of the surface layer is preferably 0.1 µm or more and 15 µm or less. In addition, when the surface layer is a charge transporting layer, the thickness is preferably 5 µm or more and 40 µm or less.

A method of curing the coat of the surface-layer coating solution (polymerizing the hole transporting substance of the present invention) is, for example, a method involving polymerizing the substance with heat, light (such as UV light), or a radiation (such as an electron beam). Of those, a radiation is preferred, and an electron beam is more preferred out of the radiations.

The substance is preferably polymerized with an electron beam because an extremely denseness (high-density) three-dimensional network structure is obtained and the wear resistance improves. In addition, productivity improves because the polymerization reaction is efficiently performed within a short time period. An accelerator to be used when the substance is irradiated with an electron beam is, for example, a scanning-, electrocurtain-, broad beam-, pulse-, or laminar-type accelerator.

When an electron beam is used, the acceleration voltage of the electron beam is preferably 120 kV or less from the following viewpoint: the deterioration of the material characteristics due to the electron beam can be suppressed without the impairment of polymerization efficiency. In addition, an electron beam absorbed dose on the surface of the coat of the surface-layer coating solution is preferably 5 kGy or more and 50 kGy or less, more preferably 1 kGy or more and 10 kGy or less.

In addition, when the hole transporting substance of the present invention is polymerized with an electron beam, the following is preferred for the purpose of the suppression of the polymerization-inhibiting action of oxygen: after having been irradiated with the electron beam in an inert gas atmosphere, the hole transporting substance is heated in the inert gas atmosphere. Examples of the inert gas include nitrogen, argon, and helium.

Next, the entire construction of the electrophotographic photosensitive member of the present invention is described.

<Electrophotographic Photosensitive Member>

A preferred construction of the electrophotographic photosensitive member in the present invention is a construction in which a charge generating layer and a hole transporting layer are laminated in the stated order on a support. As required, a conductive layer or an undercoat layer may be provided between the charge generating layer and the support, and a protective layer may be provided on the hole transporting layer. It should be noted that in the present invention, the charge generating layer and the hole transporting layer are collectively referred to as "photosensitive layer".

The hole transporting substance of the present invention is incorporated into a surface layer. The term "surface layer" as used in the present invention refers to the protective layer when the protective layer is provided in the electrophotographic photosensitive member, and refers to the hole transporting layer when the protective layer is not provided.

In addition, the photosensitive layer may be formed of a single-layer photosensitive layer containing a charge generating substance and the hole transporting substance.

<Support>

A conductive support formed of a material having electroconductivity is preferred as the support to be used in the present invention. Examples of the material for the support include: metals and alloys such as iron, copper, gold, silver, aluminum, zinc, titanium, lead, nickel, tin, antimony, indium, chromium, an aluminum alloy, and stainless steel. In addition, there may be used a support made of a metal or support made of a resin having a coat formed by depositing aluminum, an aluminum alloy, an indium oxide-tin oxide alloy, or the like through vacuum evaporation. In addition, there may also be used a support obtained by impregnating a plastic or paper with conductive particles such as carbon black, tin oxide particles, titanium oxide particles, or silver particles, or a support containing a conductive resin. The shape of the support is, for example, a cylinder-like, belt-like, sheet-like, or plate-like shape, and is most generally a cylinder-like shape.

The surface of the support may be subjected to a cutting treatment, a surface roughening treatment, an alumite treatment, or the like from the viewpoints of, for example, the suppression of an interference fringe due to the scattering of laser light, the alleviation of a defect in the surface of the support, and an improvement in conductivity of the support.

A conductive layer may be provided between the support and the undercoat layer or charge generating layer to be described later for the purpose of the suppression of an interference fringe due to the scattering of laser light or the like, resistance control, or the covering of a flaw of the support.

The conductive layer can be formed by: applying a conductive-layer coating solution obtained by subjecting carbon black, a conductive pigment, a resistance regulating pigment, or the like to a dispersion treatment together with a binder resin; and drying the resultant coat. A compound that undergoes curing polymerization through heating, UV irradiation, radiation irradiation, or the like may be added to the conductive-layer coating solution. The surface of the conductive layer obtained by dispersing the conductive pigment or the resistance regulating pigment tends to be roughened.

The thickness of the conductive layer is preferably 0.1 µm or more and 50 µm or less, more preferably 0.5 µm or more and 40 µm or less, still more preferably 1 µm or more and 30 µm or less.

Examples of the binder resin to be used for the conductive layer include: a polymer and copolymer of a vinyl compound such as styrene, vinyl acetate, vinyl chloride, an acrylic acid ester, a methacrylic acid ester, vinylidene fluoride, or trifluoroethylene; and a polyvinyl alcohol resin, a polyvinyl acetal resin, a polycarbonate resin, a polyester resin, a polysulfone resin, a polyphenylene oxide resin, a polyurethane resin, a cellulose resin, a phenol resin, a melamine resin, a silicone resin, an epoxy resin, and an isocyanate resin.

Examples of the conductive pigment and the resistance regulating pigment include particles of a metal (alloy) such as aluminum, zinc, copper, chromium, nickel, silver, or stainless steel, and plastic particles each having the metal deposited on its surface. In addition, there may be used particles of a metal oxide such as zinc oxide, titanium oxide, tin oxide, antimony oxide, indium oxide, bismuth oxide, tin-doped indium oxide, or antimony- or tantalum-doped tin oxide. One kind of those pigments may be used alone or two or more kinds thereof may be used in combination.

The undercoat layer (intermediate layer) may be provided between the support or the conductive layer and the charge generating layer for the purposes of, for example, an improvement in adhesiveness of the charge generating layer, an improvement in property by which a hole is injected from the support, and the protection of the charge generating layer from an electrical breakdown.

The undercoat layer can be formed by: applying an undercoat-layer coating solution obtained by dissolving a binder resin in a solvent; and drying the resultant coat.

Examples of the binder resin to be used for the undercoat layer include a polyvinyl alcohol resin, poly-N-vinylimidazole, a polyethylene oxide resin, ethyl cellulose, an ethylene-acrylic acid copolymer, casein, a polyamide resin, an N-methoxymethylated 6-nylon resin, a copolymerized nylon resin, a phenol resin, a polyurethane resin, an epoxy resin, an acrylic resin, a melamine resin, and a polyester resin.

Metal oxide particles may further be incorporated into the undercoat layer. An example of the metal oxide particles is particles containing titanium oxide, zinc oxide, tin oxide, zirconium oxide, or aluminum oxide. In addition, the metal oxide particles may be metal oxide particles each having a surface treated with a surface treatment agent such as a silane coupling agent.

The thickness of the undercoat layer is preferably 0.05 µm or more and 30 µm or less, more preferably 1 µm or more and 25 µm or less. Organic resin fine particles or a leveling agent may further be incorporated into the undercoat layer.

Next, the charge generating layer is described. The charge generating layer can be formed by: applying a charge-generating-layer coating solution obtained by subjecting a charge generating substance to a dispersion treatment together with a binder resin and a solvent to form a coat; and drying the resultant coat. Alternatively, the charge generating layer may be a deposited film of the charge generating substance.

Examples of the charge generating substance to be used for the charge generating layer include azo pigments, phthalocyanine pigments, indigo pigments, perylene pigments, polycyclic quinone pigments, squarylium dyes, pyrylium salts, thiapyrilium salts, triphenylmethane dyes, quinacridone pigments, azulenium salt pigments, cyanine dyestuffs, anthanthrone pigments, pyranthrone pigments, xanthene dyes, quinone imine dyes, and styryl dyes. Only one kind of those charge generating substances may be used or two or more kinds thereof may be used. Of those charge generating substances, from the viewpoint of sensitivity, phthalocyanine pigments or azo pigments are preferred, and phthalocyanine pigments are particularly more preferred.

Of the phthalocyanine pigments, in particular, oxytitanium phthalocyanines, chlorogallium phthalocyanines, or hydroxygallium phthalocyanines exhibit excellent charge generation efficiency. Further, of the hydroxygallium phthalocyanines, a hydroxygallium phthalocyanine crystal of a crystal form having peaks at Bragg angles $2\theta$ in $CuK\alpha$ characteristic X-ray diffraction of $7.4°\pm0.3°$ and $28.2°\pm0.3°$ is more preferred from the viewpoint of sensitivity.

Examples of the binder resin to be used for the charge generating layer include: polymers of vinyl compounds such as styrene, vinyl acetate, vinyl chloride, an acrylic acid ester, a methacrylic acid ester, vinylidene fluoride, and trifluoroethylene; and a polyvinyl alcohol resin, a polyvinyl acetal resin, a polycarbonate resin, a polyester resin, a polysulfone resin, a polyphenylene oxide resin, a polyurethane resin, a cellulose resin, a phenol resin, a melamine resin, a silicone resin, and an epoxy resin.

The mass ratio between the charge generating substance and the binder resin preferably falls within the range of from 1:0.3 to 1:4.

The thickness of the charge generating layer is preferably 0.05 µm or more and 1 µm or less, more preferably 0.1 µm or more and 0.5 µm or less.

Next, the hole transporting layer is described. When the hole transporting layer is the surface layer, the surface layer contains the polymerized product of the hole transporting substance of the present invention as described above.

On the other hand, when the protective layer is provided on the hole transporting layer, the hole transporting layer can be formed by: forming a coat of a hole-transporting-layer coating solution obtained by mixing the hole transporting substance and a binder resin in a solvent; and drying the coat. Hereinafter, the hole transporting substance and binder resin to be used in the hole transporting layer are described.

Examples of the hole transporting substance include a carbazole compound, a hydrazone compound, an N,N-dialkylaniline compound, a diphenylamine compound, a triphenylamine compound, a triphenylmethane compound, a pyrazoline compound, a styryl compound, and a stilbene compound.

Examples of the binder resin include an acrylic acid ester, a methacrylic acid ester, a polyvinyl alcohol resin, a polyvinyl acetal resin, a polycarbonate resin, and a polyester resin. In addition, there may be used a curable resin such as a curable phenol resin, a curable urethane resin, a curable melamine resin, a curable epoxy resin, a curable acrylic resin, or a curable methacrylic resin.

Examples of the solvent to be used for the hole-transporting-layer coating solution include an alcohol-based solvent, a sulfoxide-based solvent, a ketone-based solvent, an ether-based solvent, an ester-based solvent, an aliphatic halogenated hydrocarbon-based solvent, and an aromatic hydrocarbon-based solvent.

The thickness of the hole transporting layer is preferably 1 μm or more and 100 μm or less, more preferably 3 μm or more and 50 μm or less, still more preferably 5 μm or more and 40 μm or less.

Various additives can be added to each layer of the electrophotographic photosensitive member of the present invention. Specific examples thereof include an organic pigment, an organic dye, a coat surface adjustor, an electron transport agent, an oil, a wax, an antioxidant, a light absorber, a polymerization initiator, a radical deactivator, organic resin fine particles, and inorganic particles.

The surface of each layer of the electrophotographic photosensitive member may be subjected to surface processing with, for example, a polishing sheet, a shape transfer mold member, glass beads, or zirconia beads. In addition, unevenness may be formed in the surface with the constituent material for the coating solution.

In the application of the coating solution for each of the layers, there may be used any known application method such as a dip coating method, a spray coating method, a circular amount-regulating type (ring) coating method, a spin coating method, a roller coating method, a Mayer bar coating method, or a blade coating method.

Next, a process cartridge including the electrophotographic photosensitive member and an image forming process of the present invention are described.

FIG. 1 illustrates an example of the construction of the process cartridge of the present invention. In FIG. 1, a cylindrical electrophotographic photosensitive member 1 is rotationally driven in an arrow direction at a predetermined peripheral speed. The peripheral surface of the electrophotographic photosensitive member 1 to be rotationally driven is uniformly charged to a predetermined positive or negative potential by a charging device 2. Next, the charged peripheral surface of the electrophotographic photosensitive member 1 receives exposure light (image exposure light) 3 output from an exposing device (not shown) such as slit exposure or laser beam scanning exposure. Thus, electrostatic latent images corresponding to a target image are sequentially formed on the peripheral surface of the electrophotographic photosensitive member 1. Any one of a voltage obtained by superimposing an AC component on a DC component and a voltage consisting of the DC component may be used as a voltage to be applied to the charging device (such as a charging roller) 2.

The electrostatic latent images formed on the peripheral surface of the electrophotographic photosensitive member 1 are developed with toner in the developer of a developing device 4 to be turned into toner images. Next, the toner images formed and supported on the peripheral surface of the electrophotographic photosensitive member 1 are sequentially transferred onto a transfer material (such as paper or an intermediate transfer member) 6 by a transfer bias from a transferring device (such as a transfer roller) 5. The transfer material 6 is fed in synchronization with the rotation of the electrophotographic photosensitive member 1.

The surface of the electrophotographic photosensitive member 1 after the transfer of the toner images is subjected to an electricity eliminating treatment with pre-exposure light 7 from a pre-exposing device (not shown), and is then cleaned through the removal of transfer residual toner by a cleaning device 8. Thus, the electrophotographic photosensitive member 1 is repeatedly used in image formation. It should be noted that the pre-exposing device may be operated before or after the cleaning step, and the pre-exposing device is not necessarily needed.

The electrophotographic photosensitive member 1 may be mounted onto an electrophotographic apparatus such as a copying machine or a laser beam printer. In addition, a process cartridge 9 formed by storing two or more of the components such as the electrophotographic photosensitive member 1, the charging device 2, the developing device 4, and the cleaning device 8 in a container and integrally supporting the components can be detachably mountable to the main body of the electrophotographic apparatus. In FIG. 1, the electrophotographic photosensitive member 1, the charging device 2, the developing device 4, and the cleaning device 8 are integrally supported to form a cartridge. Then, the cartridge is used as a process cartridge 9 detachably mountable to the main body of the electrophotographic apparatus.

Next, an electrophotographic apparatus including the electrophotographic photosensitive member of the present invention is described.

Figure 2:
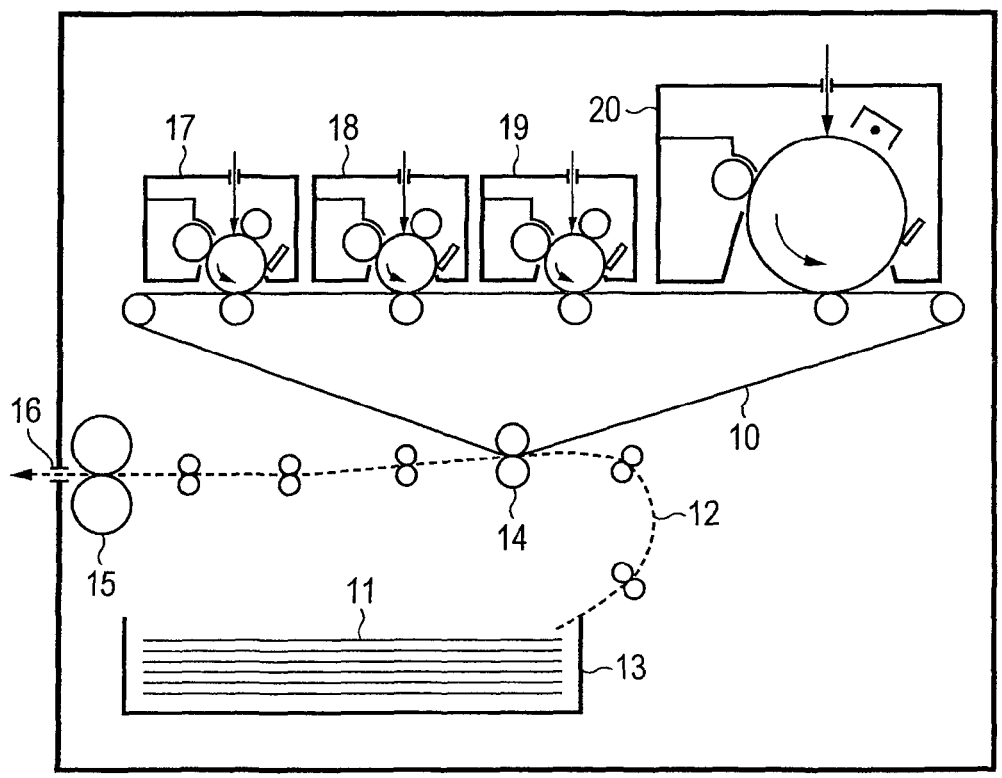
FIG. 2 is a schematic view illustrating an example of an electrophotographic apparatus including an electrophotographic photosensitive member.

FIG. 2 illustrates an example of the construction of the electrophotographic apparatus of the present invention. A process cartridge 17 for a yellow color, a process cartridge 18 for a magenta color, a process cartridge 19 for a cyan color, and a process cartridge 20 for a black color, corresponding to the respective colors, i.e., the yellow color, the magenta color, the cyan color, and the black color, are placed side by side along an intermediate transfer member 10. As illustrated in FIG. 2, the diameter and constituent material of the electrophotographic photosensitive member, a developer, a charging system, and any other device do not necessarily need to be standardized for the respective colors. For example, in the electrophotographic apparatus of FIG. 2, the diameter of the electrophotographic photosensitive member for the black color is larger than that for any other color (yellow, magenta, or cyan). In addition, a system involving using corona discharge is adopted as a charging system for the black color while a system involving applying a voltage obtained by superimposing an AC component on a DC component is adopted as a charging system for any other color.

When an image forming operation starts, the toner images of the respective colors are sequentially superimposed on the intermediate transfer member 10 according to the image forming process. In tandem with the foregoing, transfer paper 11 is sent from a sheet feeding tray 13 along a sheet feeding path 12, and is then fed to a secondary transferring device 14 in timing with the rotation operation of the intermediate transfer member. The toner images on the intermediate transfer member 10 are transferred onto the transfer paper 11 by a transfer bias from the secondary transferring device 14. The toner images transferred onto the transfer paper 11 are conveyed along the sheet feeding path 12, fixed on the transfer paper by a fixing device 15, and then discharged from a sheet discharging portion 16.

Hereinafter, the present invention is described in more detail by way of specific examples. It should be noted that the term "part(s)" in the examples refers to "part(s) by mass". In addition, an electrophotographic photosensitive member is hereinafter sometimes simply referred to as "photosensitive member".

<Production of Electrophotographic Photosensitive Member>

Example Photosensitive Member 1

A cylindrical aluminum cylinder having an outer diameter of 30 mm, a length of 357.5 mm, and a thickness of 0.7 mm was used as a support (electro-conductive support).

Next, 10 parts of zinc oxide particles (specific surface area: 19 m$^2$/g, powder resistivity: 4.7×10$^6$ Ω·cm) were mixed with 50 parts of toluene by stirring, and 0.08 part of a silane coupling agent was added to the mixture, followed by stirring for 6 hours. After that, toluene was removed by distillation under reduced pressure and the residue was dried by heating at 130° C. for 6 hours to provide surface-treated zinc oxide particles. KBM602 (compound name: N-2-(aminoethyl)-3-aminopropylmethyldimethoxysilane) manufactured by Shin-Etsu Chemical Co., Ltd. was used as the silane coupling agent.

Bragg angles 2θ±0.2° in CuKα characteristic X-ray diffraction of 7.4° and 28.2° was prepared. 2 Parts of the hydroxygallium phthalocyanine crystal, 0.02 part of a calixarene compound represented by the following structural formula (A), 1 part of polyvinyl butyral (trade name: S-LEC BX-1, manufactured by SEKISUI CHEMICAL CO., LTD.), and 60 parts of cyclohexanone were loaded into a sand mill using glass beads each having a diameter of 1 mm, followed by a dispersion treatment for 4 hours. After that, 70 parts of ethyl acetate were added to the resultant to prepare a charge-generating-layer coating solution. The charge-generating-layer coating solution was applied onto the undercoat layer by dipping, and the resultant coat was dried for 15 minutes at 80° C. to form a charge generating layer having a thickness of 0.17 μm.

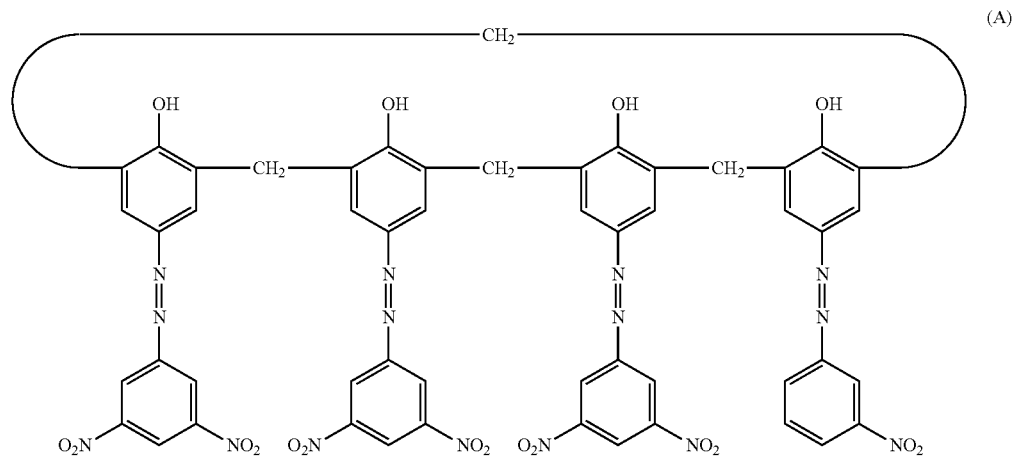

(A)

Next, 15 parts of a polyvinyl butyral resin (weight-average molecular weight: 40,000, trade name: BM-1, manufactured by SEKISUI CHEMICAL CO., LTD.) and 15 parts of a blocked isocyanate (trade name: Sumidur 3175, manufactured by Sumika Bayer Urethane Co., Ltd.) were dissolved in a mixed solution of 73.5 parts of methyl ethyl ketone and 73.5 parts of 1-butanol. 80.8 Parts of the surface-treated zinc oxide particles and 0.8 part of 2,3,4-trihydroxybenzophenone (manufactured by Tokyo Chemical Industry Co., Ltd.) were added to the solution, and the mixture was dispersed with a sand mill apparatus using glass beads each having a diameter of 0.8 mm under an atmosphere having a temperature of 23±3° C. for 3 hours. After the dispersion, 0.01 part of silicone oil (trade name: SH28PA, manufactured by Dow Corning Toray Co., Ltd.) and 5.6 parts of cross-linked polymethyl methacrylate (PMMA) particles (trade name: TECHPOLYMER SSX-102, manufactured by SEKISUI PLASTICS CO., Ltd., average primary particle diameter: 2.5 μm) were added to the resultant, and the resultant was stirred to prepare an undercoat-layer coating solution.

The undercoat-layer coating solution was applied onto the support by dipping to form a coat, and the resultant coat was dried for 40 minutes at 160° C. to form an undercoat layer having a thickness of 18 μm.

Next, a hydroxygallium phthalocyanine crystal (charge generating substance) of a crystal form having peaks at Next, 6 parts of a compound represented by the following structural formula (B), 3 parts of a compound represented by the following structural formula (C), 1 part of a compound represented by the following structural formula (D), and 10 parts of a bisphenol Z-type polycarbonate resin (trade name: Iupilon 2400, manufactured by Mitsubishi Engineering-Plastics Corporation) were dissolved in a mixed solvent of 60 parts of monochlorobenzene and 20 parts of dimethoxymethane to prepare a hole-transporting-layer coating solution. The hole-transporting-layer coating solution was applied onto the charge generating layer by dipping, and the resultant coat was dried for 50 minutes at 100° C. to form a hole transporting layer having a thickness of 18 μm.

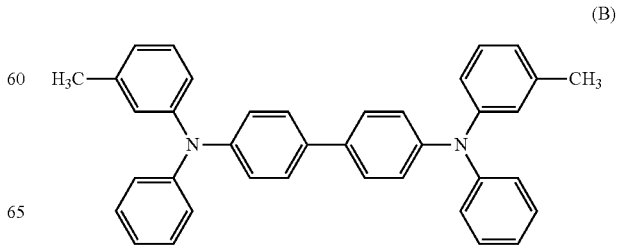

(B)

-continued

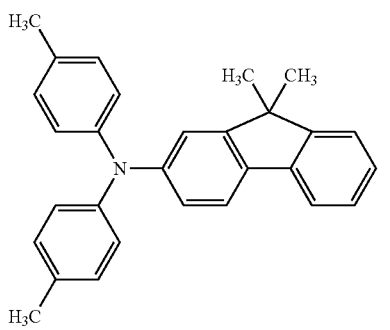
(C)

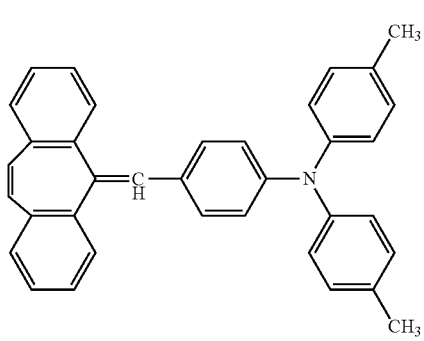
(D)

Next, 3 parts of the compound represented by Exemplified Compound No. 52 were dissolved in 5 parts of 1-methoxy-2-propanol and 2 parts of ethylene glycol dimethyl ether to prepare a protective-layer coating solution. The protective-layer coating solution was applied onto the hole transporting layer by dipping, and the resultant coat was dried for 10 minutes at 50° C., followed by a polymerization curing treatment through electron beam irradiation and heating under the following conditions.

In an atmosphere having an oxygen concentration of 100 ppm or less, the electron beam irradiation was performed with an electron beam irradiation apparatus under the conditions of an irradiation distance of 30 mm, an acceleration voltage of 70 kV, a beam current of 10 mA, and an irradiation time of 6.4 seconds while the aluminum cylinder was rotated at a speed of 300 rpm. After the electron beam irradiation, the temperature of the surface of the protective layer coat was caused to reach 130° C. over 20 seconds with an induction heating apparatus. Next, the aluminum cylinder was taken out to the air atmosphere and further heated for 10 minutes at 100° C. to form a protective layer having a thickness of 5 μm.

An example photosensitive member 1 was produced as described above.

Example Photosensitive Members 2 to 5

Electrophotographic photosensitive members were produced in the same manner as in the example photosensitive member 1 except that the compound represented by Exemplified Compound No. 52 was changed to Exemplified Compounds No. 81 (photosensitive member 2), No. 59 (photosensitive member 3), No. 61 (photosensitive member 4), and No. 94 (photosensitive member 5), respectively.

Example Photosensitive Member 6

An electrophotographic photosensitive member was produced in the same manner as in the example photosensitive member 1 except that a protective layer was formed as described below.

4 Parts of the compound represented by Exemplified Compound No. 48 were dissolved in 100 parts of tetrahydrofuran to prepare a protective-layer coating solution. The protective-layer coating solution was applied onto the hole transporting layer by spraying, and the resultant coat was dried for 10 minutes at 50° C., followed by a polymerization curing treatment through electron beam irradiation and heating under the same conditions as those of the example photosensitive member 1. Next, the aluminum cylinder was taken out to the air atmosphere and further heated for 10 minutes at 100° C. to form the protective layer having a thickness of 5 μm.

Example Photosensitive Member 7

An electrophotographic photosensitive member was produced in the same manner as in the example photosensitive member 6 except that Exemplified Compound No. 48 in the example photosensitive member 6 was changed to the compound represented by Exemplified Compound No. 99.

Example Photosensitive Member 8

The same aluminum cylinder as that used in the example photosensitive member 1 was used as a support.

Next, 60 parts of $TiO_2$ particles coated with oxygen-deficient $SnO_2$ (powder resistivity: 100 Ω·cm, coat with $SnO_2$ (mass ratio): 35%), 36.5 parts of a phenol resin (trade name: PLYOPHEN J-325, manufactured by DIC Corporation, resin solid content: 60%), and 20 parts of methoxypropanol as a solvent were dispersed with a horizontal sand mill disperser using glass beads each having a diameter of 1 mm.

The glass beads were removed from the dispersion with a mesh. After that, 1.6 parts of silicone resin particles (trade name: TOSPEARL 120, manufactured by Momentive Performance Materials Inc., average particle diameter: 2 μm) and 0.008 part of silicone oil (SH28PA) were added to the dispersion, and the resultant was stirred to prepare a conductive-layer coating solution. The average particle diameter of the $TiO_2$ particles coated with oxygen-deficient $SnO_2$ in the conductive-layer coating solution was 0.35 μm. The conductive-layer coating solution was applied onto the support by dipping to form a coat, and the resultant coat was dried and cured for 30 minutes at 140° C. to form a conductive layer having a thickness of 18 μm.

Next, 10 parts of a methoxymethylated 6-nylon resin (trade name: TORESIN EF-30T, manufactured by Nagase ChemteX Corporation) were dissolved in a mixed solvent of 100 parts of methanol and 50 parts of n-butanol to prepare an undercoat-layer coating solution. The undercoat-layer coating solution was applied onto the conductive layer by dipping, and the resultant coat was dried for 30 minutes at 100° C. to form an undercoat layer having a thickness of 0.45 μm. Next, a charge generating layer and a hole transporting layer were formed in the stated order in the same manner as in the example photosensitive member 1.

Next, a protective layer was formed in the same manner as in the example photosensitive member 6 except that Exemplified Compound No. 48 was changed to the compound represented by Exemplified Compound No. 148.

Example Photosensitive Member 9

An electrophotographic photosensitive member was produced in the same manner as in the example photosensitive member 6 except that Exemplified Compound No. 48 in the example photosensitive member 6 was changed to the compound represented by Exemplified Compound No. 101.

Figure 3:
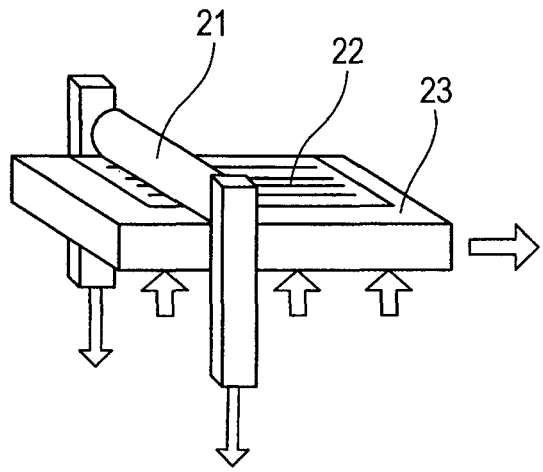
FIG. 3 is a schematic view illustrating an example of a pressure-contact shape transferring apparatus to be used in the formation of a depressed portion in the surface of an electrophotographic photosensitive member.
Figure 4A:
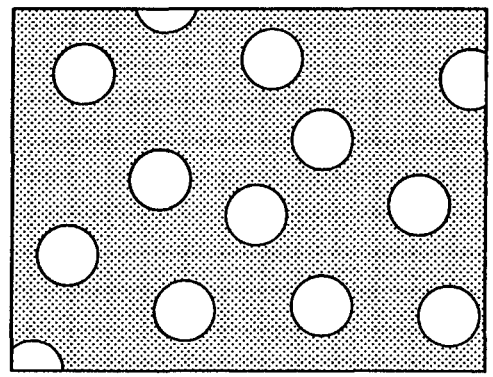
FIG. 4A is a schematic view illustrating the shape of a mold member used for an example photosensitive member 9 of the present invention.
Figure 4B:
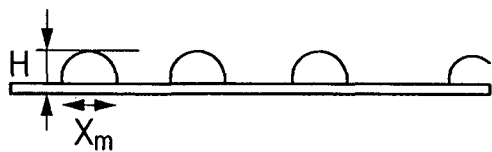
FIG. 4B is a schematic view illustrating the shape of the mold member used for the example photosensitive member 9 of the present invention.

The resultant photosensitive member was placed in a pressure-contact shape transferring apparatus of a construction illustrated in FIG. 3 with a mold member as illustrated in FIGS. 4A and 4B. The mold member illustrated in FIGS. 4A and 4B is as follows: the shape of a protruded portion is a dome-type shape having a diameter Xm of 50 μm and a height H of 3 μm, and the ratio of the total area of the protruded portions per a predetermined area including 10 or more protruded portions is 15% (hereinafter sometimes simply referred to as "area ratio of the protruded portions of the mold member"). The protective layer of the electrophotographic photosensitive member was subjected to surface shape processing with the mold member under the following conditions.

At the time of the processing, the temperatures of an electrophotographic photosensitive member 21 and a mold member 22 were controlled so that the temperature of the surface of the electrophotographic photosensitive member became 90° C. In FIG. 3, the mold member 22 was moved at a speed of 20 mm/sec in an arrow direction represented by a direction horizontal to the surface of the mold member 22 while the electrophotographic photosensitive member 21 and a pressure member 23 were pressed against each other in an arrow direction represented by a direction vertical to the surface of the mold member 22 at a pressure of 2.0 MPa. Thus, depressed portions were formed in the surface of the protective layer while the electrophotographic photosensitive member 21 was rotated to follow the movement. The depressed portions formed in the surface of the protective layer were observed with a laser microscope (VK-9500 manufactured by KEYENCE CORPORATION). As a result, the deepest depth of the depressed portions was 2 μm, the longest diameter of the depressed portions was 50 μm, and the area ratio was 15%. Thus, an example photosensitive member 9 was produced.

Example Photosensitive Member 10

An electrophotographic photosensitive member was produced in the same manner as in the example photosensitive member 6 except that Exemplified Compound No. 48 in the example photosensitive member 6 was changed to the compound represented by Exemplified Compound No. 114.

Example Photosensitive Members 11 to 14

Electrophotographic photosensitive members were produced in the same manner as in the example photosensitive member 6 except that Exemplified Compound No. 48 was changed to Exemplified Compounds No. 117 (photosensitive member 11), No. 122 (photosensitive member 12), No. 126 (photosensitive member 13), and No. 127 (photosensitive member 14), respectively.

Example Photosensitive Member 15

An electrophotographic photosensitive member was produced in the same manner as in the example photosensitive member 1 except that a protective layer was formed as described below.

4 Parts of the compound represented by Exemplified Compound No. 158 and 0.01 part of p-toluenesulfonic acid were dissolved in 100 parts of tetrahydrofuran to prepare a protective-layer coating solution. The protective-layer coating solution was applied onto the hole transporting layer by spraying, and the resultant coat was dried and thermally cured for 60 minutes at 150° C. to form the protective layer having a thickness of 6 μm.

Example Photosensitive Member 16

An electrophotographic photosensitive member was produced in the same manner as in the example photosensitive member 15 except that Exemplified Compound No. 158 in the example photosensitive member 15 was changed to the compound represented by Exemplified Compound No. 167 and the thickness of the protective layer was set to 6 μm.

Example Photosensitive Member 17

An electrophotographic photosensitive member was produced in the same manner as in the example photosensitive member 1 except that a protective layer was formed as described below.

4 Parts of the compound represented by Exemplified Compound No. 171 were dissolved in 100 parts of tetrahydrofuran to prepare a protective-layer coating solution. The protective-layer coating solution was applied onto the hole transporting layer by spraying, and the resultant coat was dried and thermally cured for 60 minutes at 150° C. to form the protective layer having a thickness of 7 μm.

Example Photosensitive Member 18

An electrophotographic photosensitive member was produced in the same manner as in the example photosensitive member 1 except that a protective layer was formed as described below.

Next, 1.5 parts of a fluorine atom-containing resin (trade name: GF400, manufactured by TOAGOSEI CO., LTD.) were dissolved in a mixed solvent of 45 parts of 1-propanol and 45 parts of 1,1,2,2,3,3,4-heptafluorocyclopentane (trade name: ZEORORA H, manufactured by ZEON CORPORATION). After that, 30 parts of ethylene fluoride resin powder (trade name: LUBRON L-2, manufactured by DAIKIN INDUSTRIES, LTD.) were added to the solution and the resultant was dispersed with a high-pressure disperser (trade name: Microfluidizer M-110EH, manufactured by Microfluidics in the U.S.) to provide an ethylene fluoride resin dispersion.

8 Parts of Exemplified Compound No. 18, 8 parts of Exemplified Compound No. 49, 8 parts of Exemplified Compound No. 68, 1 part of 1-hydroxycyclohexyl phenyl ketone, and 12 parts of the ethylene fluoride resin dispersion were added to a mixed solvent of 30 parts of tetrahydrofuran, 30 parts of 1-propanol, and 40 parts of 1,1,2,2,3,3,4-heptafluorocyclopentane (trade name: ZEORORA H, manufactured by ZEON CORPORATION), and the resultant was stirred to prepare a protective-layer coating solution. The protective-layer coating solution was applied onto the hole transporting layer by dipping, and the resultant coat was dried for 10 minutes at 45° C., followed by a photocuring treatment under the following conditions.

Under an atmosphere having an oxygen concentration of 6,000 to 8,000 ppm, photoirradiation was performed with a metal halide lamp having an output of 160 W/cm under the conditions of an irradiation distance of 100 mm, an irradiation intensity of 600 mW/cm$^2$, and an irradiation time of 2 minutes while the aluminum cylinder having applied thereto the coat of the protective-layer coating solution was rotated at a speed of 100 rpm. After the photoirradiation, the resultant was heated for 30 minutes at 135° C. to form the protective layer having a thickness of 4 μm.

Example Photosensitive Member 19

An electrophotographic photosensitive member was produced in the same manner as in the example photosensitive member 1 except that a protective layer was formed as described below.

10 Parts of the compound represented by Exemplified Compound No. 14, 10 parts of trimethylolpropane triacrylate, 2 parts of 1-hydroxycyclohexyl phenyl ketone as a photopolymerization initiator, 2 parts of 2,2-bis(4,4-di-t-butylperoxycyclohexyl)propane, and 580 parts of tetrahydrofuran were mixed to prepare a protective-layer coating solution. The protective-layer coating solution was applied onto the hole transporting layer by spraying, and the resultant coat was dried for 10 minutes at 45° C., followed by photoirradiation by the same method as that of the example photosensitive member 18. After that, the resultant was subjected to a heat treatment to form the protective layer having a thickness of 4 μm.

Example Photosensitive Member 20

An electrophotographic photosensitive member was produced in the same manner as in the example photosensitive member 1 except that a protective layer was formed as described below.

10 Parts of the compound represented by Exemplified Compound No. 30, 10 parts of trimethylolpropane triacrylate, and 570 parts of tetrahydrofuran were mixed to prepare a protective-layer coating solution. The protective-layer coating solution was applied onto the hole transporting layer by spraying, and the resultant coat was irradiated with an electron beam by the same method as that of the example photosensitive member 1. After that, the resultant was subjected to a heat treatment to form the protective layer having a thickness of 4 μm.

Example Photosensitive Member 21

An electrophotographic photosensitive member was produced in the same manner as in the example photosensitive member 1 except that a protective layer was formed as described below.

12 Parts of the compound represented by Exemplified Compound No. 45, 8 parts of ditrimethylolpropane tetraacrylate, and 570 parts of tetrahydrofuran were mixed to prepare a protective-layer coating solution. The protective-layer coating solution was applied onto the hole transporting layer by spraying, and the resultant coat was irradiated with an electron beam by the same method as that of the example photosensitive member 1. After that, the resultant was subjected to a heat treatment to form the protective layer having a thickness of 4 µm.

Example Photosensitive Member 22

An electrophotographic photosensitive member was produced in the same manner as in the example photosensitive member 1 except that a protective layer was formed as described below.

10 Parts of the compound represented by Exemplified Compound No. 50, 10 parts of 1,6-hexanediol diacrylate, and 570 parts of tetrahydrofuran were mixed to prepare a protective-layer coating solution. The protective-layer coating solution was applied onto the hole transporting layer by spraying, and the resultant coat was irradiated with an electron beam by the same method as that of the example photosensitive member 1. After that, the resultant was subjected to a heat treatment to form the protective layer having a thickness of 4 µm.

Example Photosensitive Member 23

An electrophotographic photosensitive member was produced in the same manner as in the example photosensitive member 1 except that a protective layer was formed as described below.

100 Parts of alumina particles having a number-average particle diameter of 20 nm, 30 parts of a compound having a chain polymerizable functional group represented by a rational formula "CH$_2$=CHCOO(CH$_2$)$_2$Si (CH$_3$) (OCH$_3$)$_2$", and 1,000 parts of methyl ethyl ketone were loaded into a wet sand mill containing alumina beads, and were mixed at 30° C. for 6 hours. After that, the methyl ethyl ketone and the alumina beads were separated by filtration, and the resultant was dried at 60° C. to provide surface-treated alumina particles.

2 Parts of Exemplified Compound No. 101, 2 parts of trimethylolpropane triacrylate, 0.6 part of 1-hydroxycyclohexyl phenyl ketone, and 1 part of the surface-treated alumina particles were dissolved in 100 parts of tetrahydrofuran to prepare a protective-layer coating solution. The protective-layer coating solution was applied onto the hole transporting layer by spraying, and the resultant coat was dried for 10 minutes at 45° C., followed by a photocuring treatment in the same manner as in the example photosensitive member 18. Thus, the protective layer having a thickness of 4 µm was formed.

Example Photosensitive Member 24

Surface-treated silica particles were obtained in the same manner as in the example photosensitive member 23 except that the alumina particles having a number-average particle diameter of 20 nm in the example photosensitive member 23 were changed to silica particles having a number-average particle diameter of 20 nm. A protective layer was formed and an electrophotographic photosensitive member was produced in the same manner as in the example photosensitive member 18.

Example Photosensitive Member 25

Surface-treated tin oxide particles were obtained in the same manner as in the example photosensitive member 23 except that the alumina particles having a number-average particle diameter of 20 nm in the example photosensitive member 23 were changed to tin oxide particles having a number-average particle diameter of 20 nm.

2 Parts of Exemplified Compound No. 101, 1 part of trimethylolpropane triacrylate, 1 part of a compound represented by the following structural formula (12), 0.6 part of 1-hydroxycyclohexyl phenyl ketone, and 1 part of the surface-treated tin oxide particles were dissolved in 100 parts of tetrahydrofuran to prepare a protective-layer coating solution. The protective-layer coating solution was applied onto the hole transporting layer by spraying, and the resultant coat was dried for 10 minutes at 45° C., followed by a photocuring treatment in the same manner as in the example photosensitive member 18. Thus, a protective layer having a thickness of 4 µm was formed and an electrophotographic photosensitive member was produced.

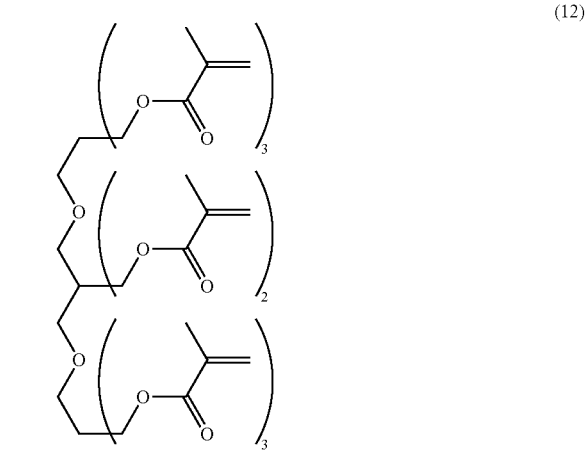

(12)

Example Photosensitive Member 26

An electrophotographic photosensitive member was produced in the same manner as in the example photosensitive member 1 except that a protective layer was formed as described below.

Next, 3.5 parts of Exemplified Compound No. 132, 0.1 part of 1-hydroxycyclohexyl phenyl ketone, and 0.3 part of α-alumina particles (trade name: SUMICORANDOM AA-3, manufactured by Sumitomo Chemical Co., Ltd.) were added to 100 parts of tetrahydrofuran, and the resultant was stirred to prepare a protective-layer coating solution. The protective-layer coating solution was applied onto the hole transporting layer by spraying, and the resultant coat was dried for 10 minutes at 45° C., followed by a photocuring treatment in the same manner as in the example photosensitive member 18. Thus, the protective layer having a thickness of 4 µm was formed.

Example Photosensitive Member 27

An example photosensitive member 27 was produced in the same manner as in the example photosensitive member 1 except that a cylindrical aluminum cylinder having an outer diameter of 84.0 mm, a length of 370 mm, and a thickness of 3.0 mm was used as a support.

Comparative Example Photosensitive Member 1

An electrophotographic photosensitive member was produced in the same manner as in the example photosensitive member 1 except that a protective layer was formed as described below.

4 Parts of a compound represented by the following structural formula (13) were dissolved in 100 parts of tetrahydrofuran to prepare a protective-layer coating solution. The protective-layer coating solution was applied onto the hole transporting layer by spraying, and the resultant coat was dried and thermally cured for 60 minutes at 150° C. to form the protective layer having a thickness of 7 µm.

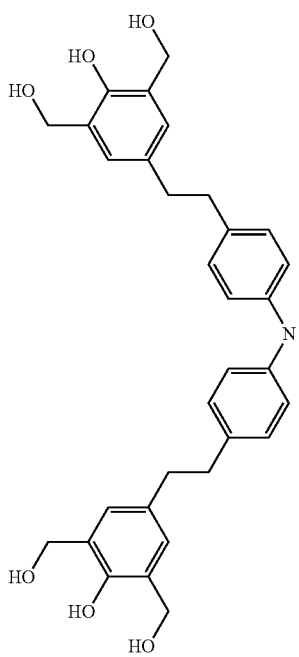
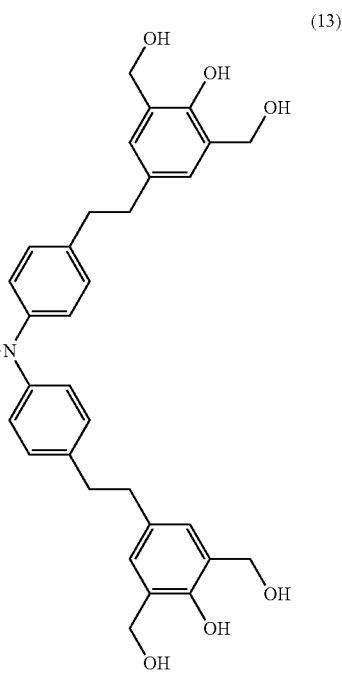

(13)

Comparative Example Photosensitive Member 2

An electrophotographic photosensitive member was produced in the same manner as in the example photosensitive member 1 except that a protective layer was formed as described below.

4 Parts of a compound represented by the following structural formula (14) were dissolved in 100 parts of tetrahydrofuran to prepare a protective-layer coating solution. The protective-layer coating solution was applied onto the hole transporting layer by spraying, and the resultant coat was dried and thermally cured for 60 minutes at 150° C. to form the protective layer having a thickness of 7 μm.

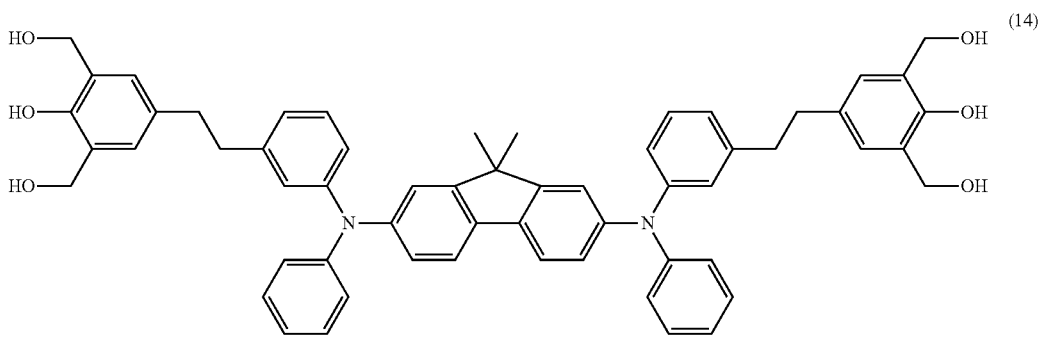 [SMILES: CC1(C)c2cc(N(c3ccccc3)c3cccc(CCc4cc(CO)c(O)c(CO)c4)c3)ccc2-c2ccc(N(c3ccccc3)c3cccc(CCc4cc(CO)c(O)c(CO)c4)c3)cc21]

(14)

Comparative Example Photosensitive Member 3

An electrophotographic photosensitive member was produced in the same manner as in the example photosensitive member 1 except that a protective layer was formed as described below.

3 Parts of a compound represented by the following structural formula (15) and 1 part of a compound represented by the following structural formula (16) were dissolved in 100 parts of tetrahydrofuran to prepare a protective-layer coating solution. The protective-layer coating solution was applied onto the hole transporting layer by spraying, and the resultant was subjected to a curing treatment with an electron beam under the same conditions as those of the example photosensitive member 1 to form the protective layer having a thickness of 5 μm.

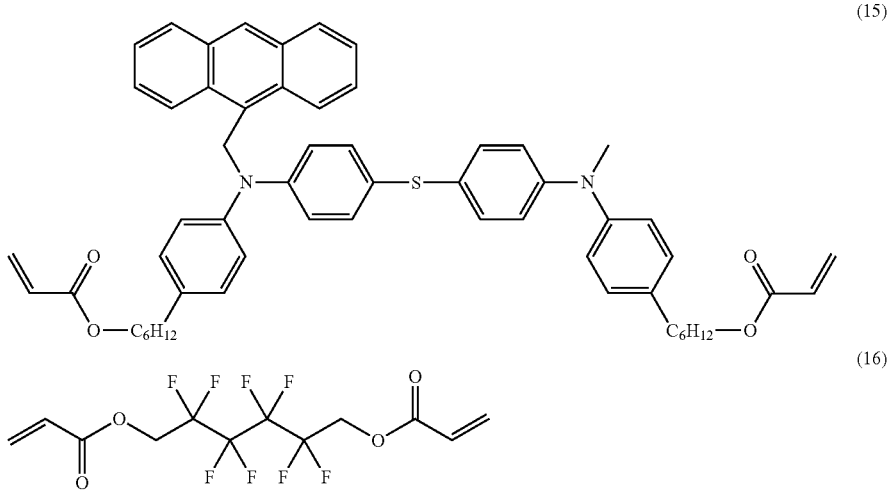

(15)

(16)

Comparative Example Photosensitive Member 4

An electrophotographic photosensitive member was produced in the same manner as in the example photosensitive member 1 except that a protective layer was formed as described below.

3 Parts of a compound represented by the following structural formula (17) and 1 part of a compound represented by the following structural formula (18) were dissolved in 100 parts of tetrahydrofuran to prepare a protective-layer coating solution. The protective-layer coating solution was applied onto the hole transporting layer by spraying, and the resultant was subjected to a curing treatment with an electron beam under the same conditions as those of the example photosensitive member 1 to form the protective layer having a thickness of 5 μm.

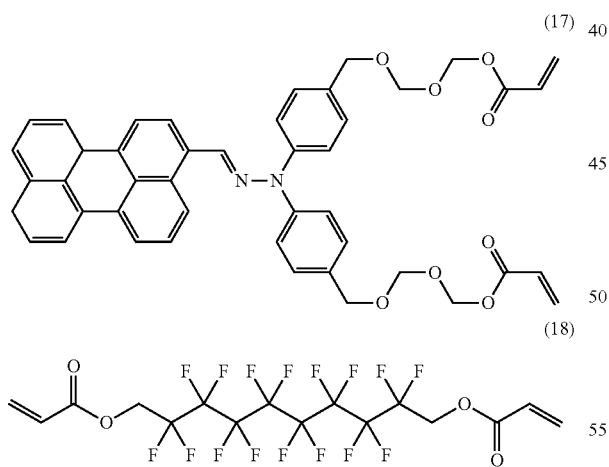

(17)

(18)

Comparative Example Photosensitive Member 5

An electrophotographic photosensitive member was produced in the same manner as in the example photosensitive member 1 except that a protective layer was formed as described below.

2 Parts of a compound represented by the following structural formula (19), 1 part of trimethylolpropane triacrylate, 1 part of caprolactone-modified dipentaerythritol hexaacrylate (KAYARAD DPCA-60, manufactured by NIPPON KAYAKU Co., Ltd.), 0.16 part of a compound represented by the following structural formula (20), and 0.2 part of 1-hydroxycyclohexyl phenyl ketone were dissolved in 100 parts of tetrahydrofuran to prepare a protective-layer coating solution. The protective-layer coating solution was applied onto the hole transporting layer by spraying, and the resultant coat was dried for 10 minutes at 45° C., followed by a photocuring treatment under the same conditions as those of the example photosensitive member 18. Thus, the protective layer having a thickness of 4 μm was formed.

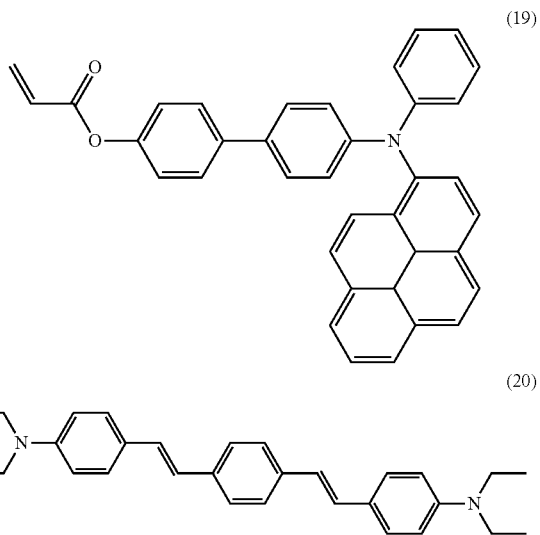

(19)

(20)

Comparative Example Photosensitive Member 6

An electrophotographic photosensitive member was produced in the same manner as in the example photosensitive member 1 except that a protective layer was formed as described below.

2 Parts of a compound represented by the following structural formula (21), 1 part of trimethylolpropane triacrylate, 1 part of caprolactone-modified dipentaerythritol hexaacrylate (KAYARAD DPCA-60), 0.16 part of a compound represented by the following structural formula (22), and 0.2 part of 1-hydroxycyclohexyl phenyl ketone were dissolved in 100 parts of tetrahydrofuran to prepare a protective-layer coating solution. The protective-layer coating solution was applied onto the hole transporting layer by spraying, and the resultant coat was dried for 10 minutes at 45° C., followed by a photocuring treatment under the same conditions as those of the example photosensitive member 18. Thus, the protective layer having a thickness of 4 µm was formed.

(21)

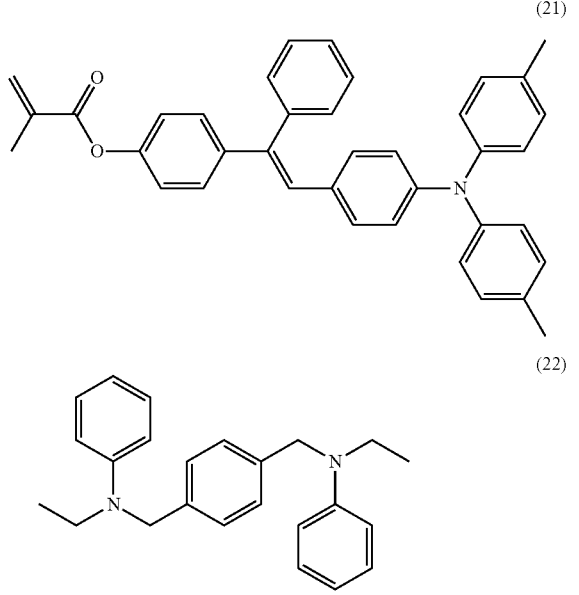

(22)

Comparative Example Photosensitive Member 7

An electrophotographic photosensitive member was produced in the same manner as in the example photosensitive member 1 except that a protective layer was formed as described below.

2 Parts of a compound represented by the following structural formula (23), 1 part of trimethylolpropane triacrylate, 1 part of caprolactone-modified dipentaerythritol hexaacrylate (KAYARAD DPCA-60), 0.16 part of a compound represented by the following structural formula (24), and 0.2 part of 1-hydroxycyclohexyl phenyl ketone were dissolved in 100 parts of tetrahydrofuran to prepare a protective-layer coating solution. The protective-layer coating solution was applied onto the hole transporting layer by spraying, and the resultant coat was dried for 10 minutes at 45° C., followed by a photocuring treatment under the same conditions as those of the example photosensitive member 18. Thus, the protective layer having a thickness of 4 µm was formed.

(23)

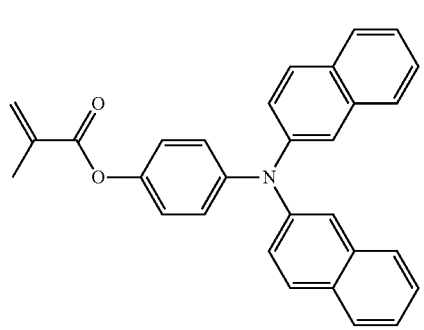

(24)

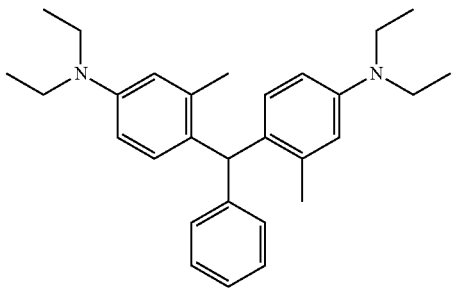

Comparative Example Photosensitive Member 8

An electrophotographic photosensitive member was produced in the same manner as in the example photosensitive member 1 except that a protective layer was formed as described below.

Next, 16 parts of a compound represented by the following structural formula (25) and 4 parts of a compound represented by the following structural formula (26) were dissolved in 100 parts of 1-propanol to prepare a protective-layer coating solution. The protective-layer coating solution was applied onto the hole transporting layer by dipping, and the resultant was subjected to a curing treatment with an electron beam under the same conditions as those of the example photosensitive member 1 to form the protective layer having a thickness of 5 µm.

(25)

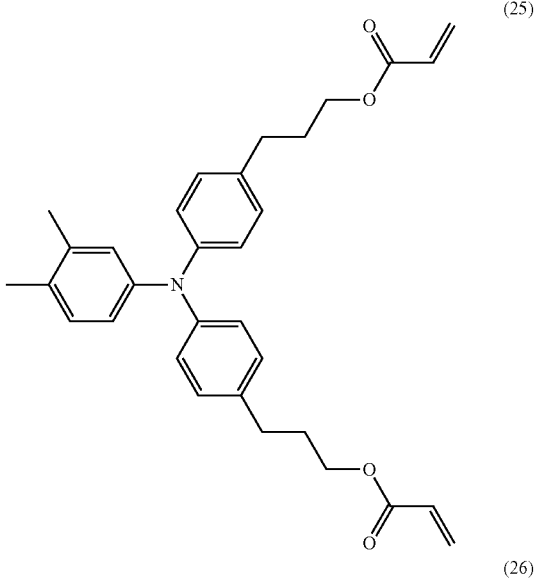

(26)

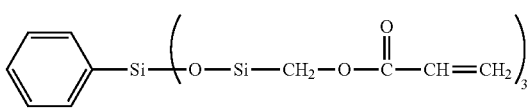

Comparative Example Photosensitive Member 9

An electrophotographic photosensitive member was produced in the same manner as in the example photosensitive member 1 except that a protective layer was formed as described below.

Next, 2 parts of a compound represented by the following structural formula (27) and 2 parts of a compound represented by the following structural formula (28) were dissolved in 100 parts of tetrahydrofuran to prepare a protective-layer coating solution. The protective-layer coating solution was applied onto the hole transporting layer by spraying, and the resultant was subjected to a curing treatment with an electron beam under the same conditions as those of the example photosensitive member 1 to form the protective layer having a thickness of 5 μm.

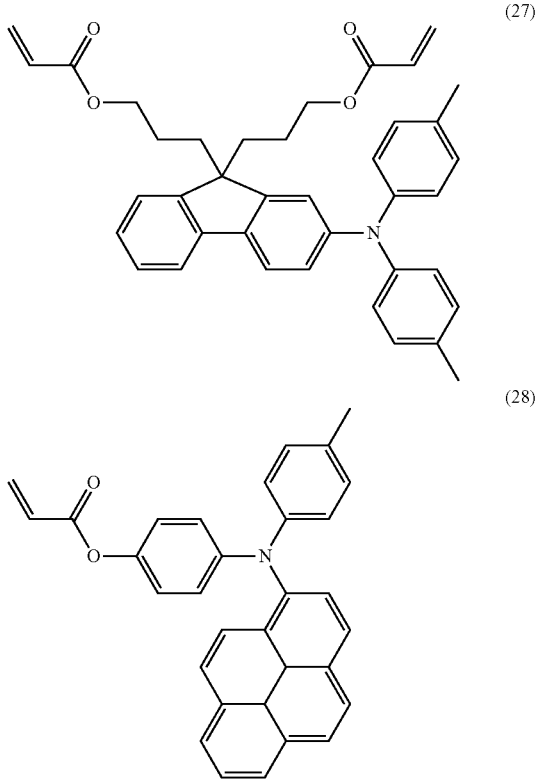

(27)

(28)

Comparative Example Photosensitive Member 10

A comparative example photosensitive member 10 was produced in the same manner as in the comparative example photosensitive member 9 except that a cylindrical aluminum cylinder having an outer diameter of 84.0 mm, a length of 370 mm, and a thickness of 3.0 mm was used as a support in the comparative example photosensitive member 9.

<Evaluation: Sensitivity and Residual Potential>

Each of the produced example photosensitive members 1 to 26 and comparative example photosensitive members 1 to 9 was evaluated for its sensitivity and residual potential under the following conditions.

A photosensitive member testing apparatus (trade name: CYNTHIA 59, manufactured by GEN-TECH, INC.) was used. First, a condition for a charging device was set so that the surface potential of the electrophotographic photosensitive member became −700 V under an environment having a temperature of 23° C. and a humidity of 50% RH. The photosensitive member was irradiated with monochromatic light having a wavelength of 780 nm, and the quantity of the light needed for reducing the potential of −700 V to −200 V was measured and defined as a sensitivity (μJ/cm$^2$). Further, the potential of the photosensitive member when the photosensitive member was irradiated with light having a quantity of 20 (μJ/cm$^2$) was measured and defined as a residual potential (V).

<Evaluation: Image Deletion 1>

Image deletion 1 was evaluated with the produced example photosensitive members 1 to 26 and comparative example photosensitive members 1 to 9 under the following conditions.

A reconstructed machine of a copying machine available under the trade name "iR-C3380F" from Canon Inc. was used as an electrophotographic apparatus. With regard to the reconstructed points, the machine was reconstructed so that image exposure laser power, the quantity of a current flowing from the charging roller to the support of the electrophotographic photosensitive member (hereinafter sometimes referred to as "total current"), and a voltage to be applied to the charging roller could be regulated and measured. Further, a cassette heater was removed.

First, the electrophotographic apparatus and the electrophotographic photosensitive members were left to stand in an environment having a temperature of 30° C. and a humidity of 80% RH for 24 hours or more. After that, each of the example and comparative example electrophotographic photosensitive members was mounted onto the cartridge for a cyan color of the electrophotographic apparatus.

Next, a solid image was output on A4 size plain paper with a cyan color alone and an image exposure light quantity was set so that a density on the paper measured with a spectral densitometer (trade name: X-Rite 504, manufactured by X-Rite Inc.) became 1.45.

Next, the applied voltage was applied while being changed from −400 V to −1,600 V by 100 V, and a total current at each applied voltage was measured. Then, a graph whose axis of abscissa and axis of ordinate indicates the applied voltage and the total current, respectively was created, and the applied voltage at which a current component (hereinafter sometimes referred to as "discharge current") diverging from a first-order approximation curve in the applied voltage range of from −400 V to −800 V became 100 μA was measured. The total current was set to the total current value at the applied voltage at which the discharge current became 100 μA.

Next, an A4 size square lattice image having a line width of 0.1 mm and a line interval of 10 mm was read with a scanner and continuously output on 5,000 sheets with a cyan color alone. After the image output, the main power source of the electrophotographic apparatus was turned off and the electrophotographic apparatus was left to stand for 3 days. After the standing, the main power source of the electrophotographic apparatus was turned on. Immediately after that, the square lattice image was similarly output on 1 sheet, the image deletion of the output image was visually observed, and the image deletion 1 was evaluated by the following criteria.

Evaluation ranks were as described below.

Rank 5: No anomaly is observed in the lattice image.
Rank 4: A horizontal line of the lattice image is broken but no anomaly is observed in a vertical line thereof.
Rank 3: A horizontal line of the lattice image disappears but no anomaly is observed in a vertical line thereof.
Rank 2: A horizontal line of the lattice image disappears and a vertical line thereof is broken.
Rank 1: A horizontal line of the lattice image disappears and a vertical line thereof also disappears.

In this case, the horizontal line of the lattice image refers to a line parallel to the cylinder axis direction of the photosensitive member and the vertical line thereof refers to a line vertical to the cylinder axis direction of the photosensitive member.

<Evaluation: Image Deletion 2>

Image deletion 2 was evaluated with the produced example photosensitive member 27 and comparative example photosensitive member 10 under the following conditions.

A copying machine available under the trade name "imagePRESS C1+" from Canon Inc. was reconstructed as described below and used as an electrophotographic apparatus. The machine was reconstructed so that image exposure laser power could be regulated and measured, and a drum heater was removed.

First, the electrophotographic apparatus and the electrophotographic photosensitive members were left to stand in an environment having a temperature of 30° C. and a humidity of 80% RH for 24 hours or more. After that, each of the electrophotographic photosensitive members was mounted onto the electrophotographic apparatus.

Next, a solid image was output on A4 size plain paper with a cyan color alone and an image exposure light quantity was set so that a density on the paper measured with a spectral densitometer (trade name: X-Rite 504, manufactured by X-Rite Inc.) became 1.45.

Next, the same A4 size square lattice image as that of the evaluation method for the image deletion 1 was read with a scanner and output on 5,000 sheets. After the image output, the main power source of the electrophotographic apparatus was turned off and the electrophotographic apparatus was left to stand for 3 days. After the standing, the main power source of the electrophotographic apparatus was turned on. Immediately after that, the square lattice image was similarly output on 1 sheet, the image deletion of the output image was visually observed, and the image deletion 2 was evaluated. The same evaluation ranks as those of the evaluation method for the image deletion 1 were used.

<Evaluation: Wear Amount>

The protective layer of each of the produced example photosensitive members 1 to 26 and comparative example photosensitive members 1 to 9 was evaluated for its wear amount under the following conditions.

A reconstructed machine of a copying machine available under the trade name "iR ADVANCE C5051F" from Canon Inc. was used as an electrophotographic apparatus. The machine was reconstructed so that image exposure laser power could be regulated.

First, the thickness of the protective layer of the electrophotographic photosensitive member before 100,000-sheet output was measured with an interference thickness meter (trade name: MCPD-3700, manufactured by Otsuka Electronics Co., Ltd.).

Next, the electrophotographic apparatus and the electrophotographic photosensitive member were left to stand in an environment having a temperature of 23° C. and a humidity of 50% RH for 24 hours or more. After that, the electrophotographic photosensitive member was mounted onto the cartridge for a cyan color of the electrophotographic apparatus.

Next, a halftone image was output on A4 size plain paper with a cyan color alone and image exposure laser power was set so that the density of the output image measured with a spectral densitometer (trade name: X-Rite 504, manufactured by X-Rite Inc.) became 0.85, followed by continuously output on 100,000 sheets.

Next, the electrophotographic photosensitive member was taken out of the electrophotographic apparatus, the thickness of the protective layer after the 100,000-sheet output was measured, and a difference between the thicknesses of the protective layer before and after the 100,000-sheet output (i.e., the wear amount) was calculated. Table 1 shows the results of the evaluation.

TABLE 1

| | Hole transporting substance | | Result of evaluation of photosensitive member | | | | |
|---|---|---|---|---|---|---|---|
| | Hole transporting substance | Number of $sp^2$ carbon atoms [atom(s)] | Sensitivity [$\mu J/cm^2$] | Residual potential [-V] | Image deletion 1 [rank] | Image deletion 2 [rank] | Wear amount [$\mu m$] |
| Example 1 | Exemplified Compound No. 52 | 28 | 0.37 | 44 | 5 | — | 0.2 |
| Example 2 | Exemplified Compound No. 81 | 36 | 0.42 | 53 | 4 | — | 0.1 |
| Example 3 | Exemplified Compound No. 59 | 34 | 0.39 | 57 | 5 | — | 0.2 |
| Example 4 | Exemplified Compound No. 61 | 32 | 0.42 | 40 | 5 | — | 0.2 |
| Example 5 | Exemplified Compound No. 94 | 40 | 0.35 | 38 | 4 | — | 0.1 |
| Example 6 | Exemplified Compound No. 48 | 28 | 0.37 | 42 | 5 | — | 0.3 |
| Example 7 | Exemplified Compound No. 99 | 44 | 0.33 | 35 | 5 | — | 0.3 |
| Example 8 | Exemplified Compound No. 148 | 28 | 0.38 | 49 | 5 | — | 0.3 |
| Example 9 | Exemplified Compound No. 101 | 44 | 0.34 | 33 | 5 | — | 0.2 |
| Example 10 | Exemplified Compound No. 114 | 36 | 0.44 | 61 | 3 | — | 0.3 |
| Example 11 | Exemplified Compound No. 117 | 40 | 0.33 | 41 | 5 | — | 0.2 |
| Example 12 | Exemplified Compound No. 122 | 42 | 0.34 | 36 | 4 | — | 0.2 |
| Example 13 | Exemplified Compound No. 126 | 38 | 0.38 | 44 | 4 | — | 0.2 |
| Example 14 | Exemplified Compound No. 127 | 42 | 0.34 | 31 | 3 | — | 0.2 |
| Example 15 | Exemplified Compound No. 158 | 44 | 0.31 | 33 | 5 | — | 0.3 |
| Example 16 | Exemplified Compound No. 167 | 36 | 0.45 | 64 | 3 | — | 0.3 |
| Example 17 | Exemplified Compound No. 171 | 28 | 0.36 | 47 | 4 | — | 0.3 |
| Example 18 | Exemplified Compound No. 18 | 24 | 0.39 | 52 | 5 | — | 0.3 |
| | Exemplified Compound No. 49 | 28 | | | | | |
| | Exemplified Compound No. 68 | 36 | | | | | |
| Example 19 | Exemplified Compound No. 14 | 30 | 0.44 | 67 | 4 | — | 0.2 |
| Example 20 | Exemplified Compound No. 30 | 34 | 0.43 | 64 | 4 | — | 0.1 |
| Example 21 | Exemplified Compound No. 45 | 32 | 0.41 | 60 | 4 | — | 0.1 |
| Example 22 | Exemplified Compound No. 50 | 28 | 0.41 | 55 | 5 | — | 0.3 |
| Example 23 | Exemplified Compound No. 101 | 44 | 0.32 | 35 | 5 | — | 0.1 |
| Example 24 | Exemplified Compound No. 101 | 44 | 0.36 | 53 | 4 | — | 0.1 |
| Example 25 | Exemplified Compound No. 101 | 44 | 0.35 | 58 | 4 | — | 0.1 |
| Example 26 | Exemplified Compound No. 132 | 56 | 0.31 | 31 | 5 | — | 0.1 |
| Example 27 | Exemplified Compound No. 52 | 28 | — | — | — | 5 | — |
| Comparative Example 1 | Structural formula (13) | — | 0.22 | 31 | 1 | — | 0.3 |
| Comparative Example 2 | Structural formula (14) | — | 0.19 | 29 | 1 | — | 0.3 |
| Comparative Example 3 | Structural formula (15) | — | 0.39 | 51 | 2 | — | 0.2 |
| Comparative Example 4 | Structural formula (17) | — | 0.32 | 39 | 2 | — | 0.2 |
| Comparative Example 5 | Structural formula (19) | — | 0.19 | 26 | 2 | — | 0.2 |
| Comparative Example 6 | Structural formula (21) | — | 0.28 | 37 | 2 | — | 0.2 |

TABLE 1-continued

|  | Hole transporting substance | Number of sp² carbon atoms [atom(s)] | Sensitivity [μJ/cm²] | Residual potential [−V] | Image deletion 1 [rank] | Image deletion 2 [rank] | Wear amount [μm] |
|---|---|---|---|---|---|---|---|
| Comparative Example 7 | Structural formula (23) | — | 0.23 | 30 | 2 | — | 0.2 |
| Comparative Example 8 | Structural formula (25) | — | 0.17 | 25 | 2 | — | 0.2 |
| Comparative Example 9 | Structural formula (27)/Structural formula (28) | — | 0.20 | 28 | 1 | — | 0.2 |
| Comparative Example 10 | Structural formula (27)/Structural formula (28) | — | — | — | — | 2 | — |

As can be seen from the results of Table 1, the example photosensitive members each had much better performance than that of each of the comparative example photosensitive members in terms of the image deletion while the example photosensitive members each had performance comparable to that of each of the comparative example photosensitive members in terms of the sensitivity, the residual potential, and the wear amount.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-045712, filed Mar. 7, 2013, and Japanese Patent Application No. 2014-040676, filed Mar. 3, 2014, which are hereby incorporated by reference herein in their entirety.

REFERENCE SIGNS LIST 1 electrophotographic photosensitive member
2 charging device
3 exposure light
4 developing device
5 transferring device
6 transfer material
7 pre-exposure light
8 cleaning device
9 process cartridge
10 intermediate transfer member
11 transfer paper
12 sheet feeding path
13 sheet feeding tray
14 secondary transferring device
15 fixing device
16 sheet discharging portion
17 process cartridge for yellow color
18 process cartridge for magenta color
19 process cartridge for cyan color
20 process cartridge for black color
21 electrophotographic photosensitive member
22 mold member
23 pressure member
Xm diameter of protruded portion of mold member
H height of protruded portion of mold member

The invention claimed is:

1. An electrophotographic photosensitive member comprising:
   a conductive support formed of a material having electroconductivity; and
   a photosensitive layer formed on the conductive support,
   a surface layer of the electrophotographic photosensitive member comprising a polymerized product of a hole transporting substance having a reactive functional group, wherein
   a structure other than the reactive functional group of the hole transporting substance is one of (i) a structure consisting of a carbon atom and a hydrogen atom, or (ii) a structure consisting of a carbon atom, a hydrogen atom and an oxygen atom,
   the structure other than the reactive functional group of the hole transporting substance comprises a structure which comprises a conjugate structure comprising 24 or more sp² carbon atoms, wherein
   the conjugate structure comprises a condensed polycyclic structure comprising 12 or more sp² carbon atoms, and
   the reactive functional group comprises one of an acryloyloxy group or a methacryloyloxy group, and wherein the hole transporting substance comprises two or more units of the condensed polycyclic structures.

2. The electrophotographic photosensitive member according to claim 1, wherein the condensed polycyclic structures are connected to each other by a single bond.

3. The electrophotographic photosensitive member according to claim 1, wherein the condensed polycyclic structure is formed of one of a five-membered ring and a six-membered ring.

4. The electrophotographic photosensitive member according to claim 1, wherein the structure other than the reactive functional group of the hole transporting substance comprises a conjugate structure comprising 28 or more sp² carbon atoms.

5. The electrophotographic photosensitive member according to claim 1, wherein a compound obtained by substituting the reactive functional group of the hole transporting substance with a hydrogen atom is a compound represented by formula (1):

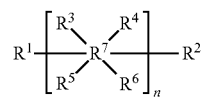

(1)

where $R^1$ to $R^6$ each independently represent a hydrogen atom, a substituted or unsubstituted alkyl group, a substituted or unsubstituted alkoxy group, a substituted or unsubstituted aralkyl group, or a substituted or unsubstituted aryl group,
$R^7$ represents a group derived from a substituted or unsubstituted arene by loss of 6 hydrogen atoms, and
n represents an integer of from 1 to 10, and when n represents from 2 to 10, partial structures each represented by formula (2) in formula (1) may be identical to or different from each other

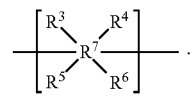

(2)

6. The electrophotographic photosensitive member according to claim 5, wherein the arene in $R^7$ of formula (1) is fluorene, anthracene, phenanthrene, fluoranthene, or pyrene.

7. The electrophotographic photosensitive member according to claim 1, wherein the surface layer comprises a polymerized product of a composition comprising:
   the hole transporting substance; and
   a compound having a reactive functional group and free of a structure having hole transportability.

8. The electrophotographic photosensitive member according to claim 7, wherein:
   the hole transporting substance has one or more reactive functional groups; and
   the compound free of a structure having hole transportability has two or more reactive functional groups.

9. The electrophotographic photosensitive member according to claim 7, wherein the compound having a reactive functional group and free of a structure having hole transportability has a molecular weight of 100 to 1,000.

10. The electrophotographic photosensitive member according to claim 1, wherein the surface layer further comprises inorganic fine particles whose surfaces have been treated with a compound having a chain polymerizable functional group.

11. The electrophotographic photosensitive member according to claim 10, wherein the inorganic fine particles are particles each comprising at least one oxide selected from the group consisting of alumina, silica, tin oxide, and titanium oxide.

12. The electrophotographic photosensitive member according to claim 5, wherein the compound obtained by substituting the reactive functional group of the hole transporting substance with a hydrogen atom has a molecular weight of 300 to 3,000.

13. A process cartridge detachably mountable to a main body of an electrophotographic apparatus, wherein the process cartridge integrally supports: the electrophotographic photosensitive member according to claim 1; and at least one device selected from the group consisting of a charging device, a developing device, a transferring device, and a cleaning device.

14. An electrophotographic apparatus comprising: the electrophotographic photosensitive member according to claim 1; a charging device; an exposing device; a developing device; and a transferring device.

* * * * *